United States Patent [19]

Morgan, Jr. et al.

[11] Patent Number: 6,083,926

[45] Date of Patent: *Jul. 4, 2000

[54] WATER SOLUBLE VITAMIN $B_{12}$ RECEPTOR MODULATING AGENTS AND METHODS RELATED THERETO

[75] Inventors: A. Charles Morgan, Jr., Mill Creek; D. Scott Wilbur, Edmonds; Pradip M. Pathare, Seattle, all of Wash.

[73] Assignees: The University of Washington, Seattle; Receptagen Corporation, Edmonds, both of Wash.

[ * ] Notice: This patent is subject to a terminal disclaimer.

[21] Appl. No.: 09/200,422

[22] Filed: Nov. 23, 1998

Related U.S. Application Data

[60] Division of application No. 08/545,151, Oct. 19, 1995, Pat. No. 5,840,712, which is a continuation-in-part of application No. PCT/US95/04404, Apr. 7, 1995, which is a continuation-in-part of application No. 08/406,191, Mar. 16, 1995, Pat. No. 5,840,880, which is a continuation-in-part of application No. 08/406,192, Mar. 16, 1995, Pat. No. 5,739,287, and a continuation-in-part of application No. 08/406,194, Mar. 16, 1995, Pat. No. 5,869,465, which is a continuation-in-part of application No. 08/224,831, Apr. 8, 1994, abandoned.

[51] Int. Cl.[7] .......................... A61K 31/70; C07H 23/00; G01N 33/567

[52] U.S. Cl. ...................... 514/52; 514/2; 514/8; 514/12; 514/21; 514/387; 536/26.4; 536/26.41; 436/505; 548/303.7; 530/350; 530/367; 530/370; 530/395; 530/409; 530/825

[58] Field of Search ...................... 530/395, 350, 530/367, 370, 409, 825; 548/303.7; 514/387, 52, 2, 8, 12, 21; 436/505; 536/26.4, 26.41

[56] References Cited

U.S. PATENT DOCUMENTS

| | | | |
|---|---|---|---|
| 4,167,556 | 9/1979 | Selhub et al. | 436/505 |
| 5,428,023 | 6/1995 | Russell-Jones et al. | 514/21 |
| 5,538,901 | 7/1996 | Law et al. | 436/501 |
| 5,574,018 | 11/1996 | Habberfield et al. | 514/21 |
| 5,589,463 | 12/1996 | Russell-Jones et al. | 514/21 |
| 5,739,287 | 4/1998 | Wilbur et al. | 530/367 |

FOREIGN PATENT DOCUMENTS

| | | |
|---|---|---|
| 0 069 450 A1 | 1/1983 | European Pat. Off. . |
| 0 361 817 A2 | 4/1990 | European Pat. Off. . |
| 0 378 203 A2 | 7/1990 | European Pat. Off. . |
| 0 425 680 A1 | 5/1991 | European Pat. Off. . |
| 0 599 325 A1 | 6/1994 | European Pat. Off. . |
| WO 93/23557 | 11/1993 | WIPO . |
| WO 94/27613 | 12/1994 | WIPO . |

*Primary Examiner*—Kathleen K. Fonda
*Attorney, Agent, or Firm*—Seed Intellectual Property Law Group PLLC

[57] ABSTRACT

Vitamin $B_{12}$ receptor modulating agents capable of modulating cell surface receptors by affecting the cell surface receptor trafficking pathway are disclosed. The vitamin $B_{12}$ receptor modulating agents are comprised of a covalently bound rerouting moiety and targeting moiety linked by a water-solublizing linker.

16 Claims, 18 Drawing Sheets

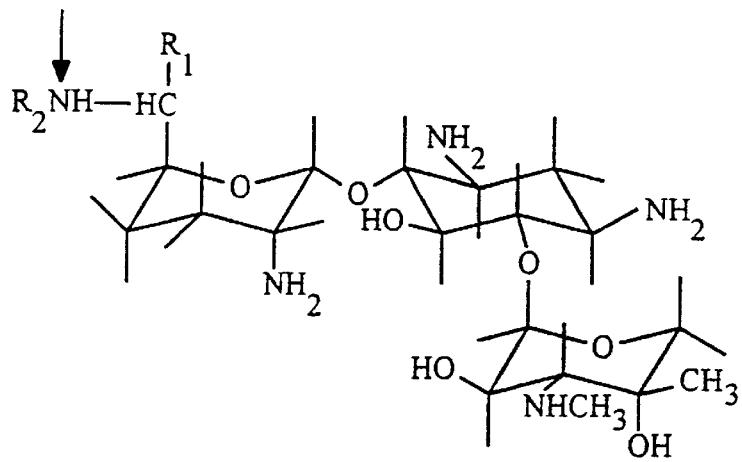
Gentamicin C$_1$ :   R$_1$ = R$_2$ = CH$_3$
Gentamicin C$_2$ :   R$_1$ = CH$_3$; R$_2$ = H
Gentamicin C$_{1a}$:  R$_1$ = R$_2$ = H
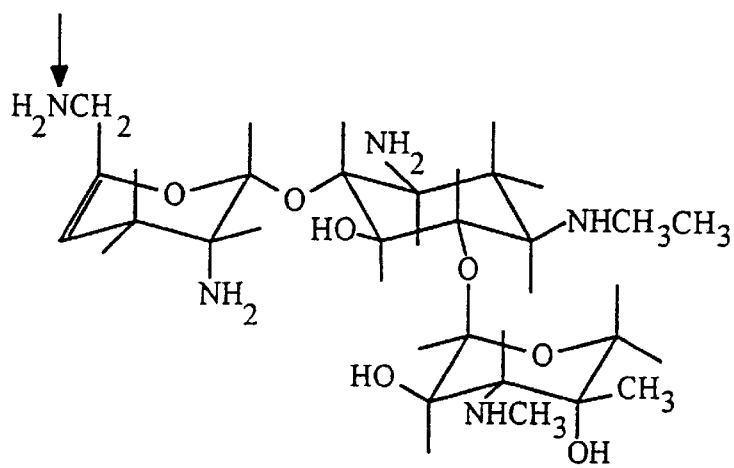
Netilmicin
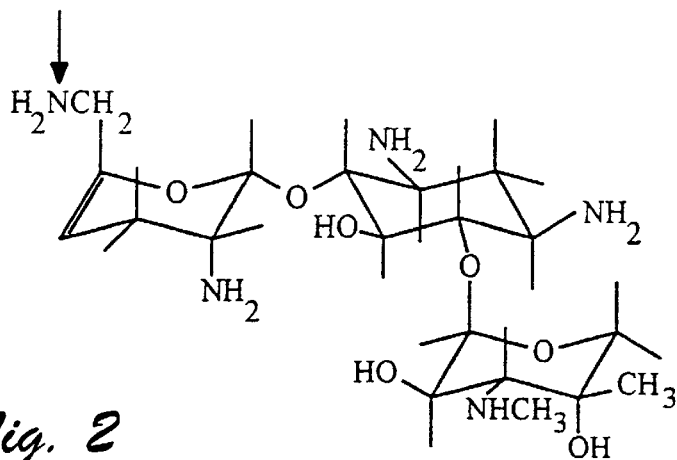
Fig. 2
Sisomicin

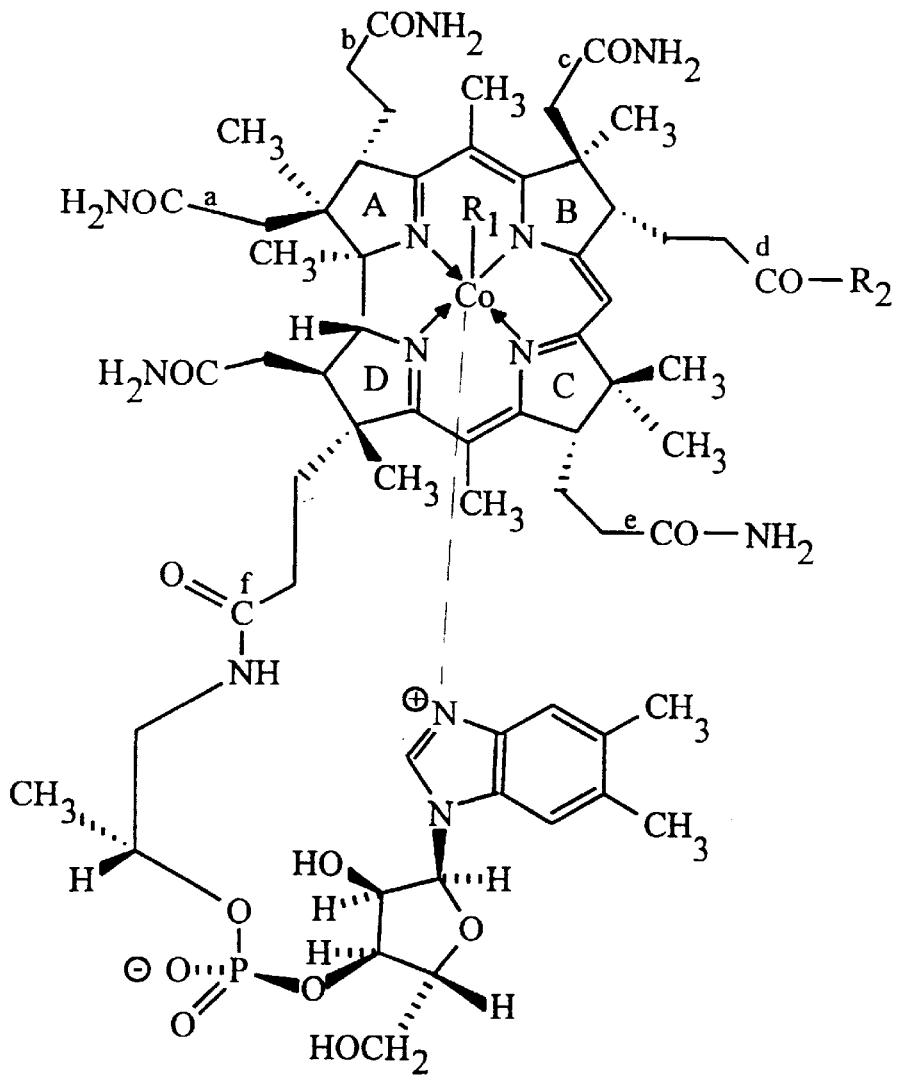

$R_1 = CN$ ; $R_2 = NH_2$ (Cyanocobalamin)
$R_1 = CN$ ; $R_2 = OH$ (Cyanocobalamin -(3)-free acid)
$R_1 = CN$ ; $R_2 = HN\text{-}CH_2\text{-}CH_2\text{-}CH_2\text{-}CO_2H$ (GABA adduct)
$R_1 = CN$ ; $R_2 = $ GABA - Peptide (where GABA = linker)
$R_1 = CN$ ; $R_2 = $ Peptide
$R_1 = CN$ ; $R_2 = $ HN-(linker)-tyramine-$^{125}$I
$R_1 = CN$ ; $R_2 = $ HN-(linker)-lysosomotropic agent
$R_1 = CN$ ; $R_2 = $ HN-(linker)-X-linking agent
$R_1 = CN$ ; $R_2 = $ HN-(linker)-biotin
$R_1 = CN$ ; $R_2 = $ NH-$(CH_2)_{12}NH_2$

Fig. 8

WATER SOLUBLE VITAMIN B$_{12}$ RECEPTOR MODULATING AGENTS AND METHODS RELATED THERETO

CROSS-REFERENCE TO RELATED APPLICATION

This application is a divisional of U.S. Pat. application Ser. No. 08/545,151, filed Oct. 19, 1995, now U.S. Pat. No. 5,840,712; which is a continuation-in-part of PCT/US95/04404, filed Apr. 7, 1995; which is a continuation-in-part of U.S. Pat. applications Ser. No. 08/406,191, now U.S. Pat. No. 5,840,880, Ser. No. 08/406,192, now U.S. Pat. No. 5,739,287, and Ser. No. 08/406,194, now U.S. Pat. No. 5,869,465, all filed Mar. 16, 1995; which are continuations-in-part of U.S. patent application Ser. No. 08/224,831, filed Apr. 8, 1994, now abandoned, the benefit of the priority of the filing dates of which is hereby claimed under 35 U.S.C. § 120.

FIELD OF THE INVENTION

The present invention is generally directed to receptor modulating agents which modulate cell surface receptors and, more specifically, to water soluble vitamin B$_{12}$ receptor modulating agents which bind TcII cell surface receptors and affect the receptor trafficking pathway and methods related thereto.

BACKGROUND OF THE INVENTION

Cell surface receptors constitute a class of proteins which are responsible for receptor-mediated endocytosis of specific ligands. Basically, the receptors serve as escorts for ligand delivery to intracellular destinations.

Ligand delivery is generally achieved through coated regions on the plasma membrane called "coated pits." These pits continually invaginate and pinch off, forming "coated vesicles" in the cytoplasm. Coated pits and vesicles provide a pathway for receptor mediated endocytosis of specific ligands. The ligands that bind to specific cell surface receptors are internalized via coated pits, enabling cells to ingest large numbers of specific ligands without taking in correspondingly large volume of extracellular fluid. The internalized coated vesicles may or may not lose their coats and bind with other vesicles to form larger vesicles called "endosomes." In the endosome the ligand and the receptor are separated or "sorted." Endosomes which sort ligands and receptors are known as "compartment of uncoupling of receptor and ligand" or "CURL."

Endosomes may fuse with primary lysosomes, where their contents are digested, or they may be delivered to other intracellular destinations. The receptor proteins are generally not digested, but are rather recycled to the cell membrane surface through a process called "exocytosis," or transferred to early or late endosomes via multivesicular bodies. The entire pathway is referred to as the "receptor trafficking pathway."

Some receptors deliver their ligand directly to the cytoplasm or other specific intracellular locations. Perhaps one of the most studied receptor trafficking pathways is that of iron transport. In this pathway, a serum carrier protein, transferrin, binds iron and transports it to transferrin receptors on the plasma membrane surface. After binding and internalization, via coated pits, the resulting vesicle combines first with early endosomes and then with late endosomes. This process results in the gradual drop in pH in the vesicle. The drop in pH causes the transferrin carrier protein to lose its affinity to iron. When this occurs, the iron translocates through the membrane of the vesicle and joins the intracellular pool of enzymes. The transferrin receptor may then recycle to the cell surface where it may repeat the process.

Other receptors may deliver their ligand directly to the lysosomes for digestion. For example, the epidermal growth factor ("EGF") receptor delivers its ligand directly to a lysosome for degradation (*Prog. Histochem. Cytochem.* 26:39–48,1992). The EGF receptor may recycle to the cell surface depending on its state of phosphorylation (*Cancer Treat. Rep.* 61:139–160, 1992; *J. Cell. Biol.* 116:321–330, 1992).

A single receptor may utilize more than one receptor trafficking pathway within the same cell. For example in polarized cells, such as specialized transport epithelia cells, membrane trafficking is distinct between apical and basal sides of the cell (*Sem. Cell. Biol.* 2:387–396, 1991). Moreover, non-polarized epithelia cells may simultaneously follow two separate sorting pathways.

The control or regulation of cell surface receptors may be achieved by a variety of techniques. Regulation of cell surface receptors may be accomplished, at a very basic level, by the binding of naturally occurring ligands. As discussed above, receptor binding of a ligand will generally trigger the internalization of the ligand-receptor complex. Such internalization may desensitize the cell to further ligand binding. (*J. Immunol.* 150:3161–9, 1993; *Mol. Endocrinol.* 6:2090–102, 1992; *J. Cell. Physiol.* 154:281–8, 1993; *Receptor* 1:13–32, 1990–91; *Biochem. J.* 288:55–61, 1992; *J. Immunol.* 148:2709–11, 1992; *J. Cell. Physiol.* 148:24–34, 1991). This type of regulation, however, is transient in nature and does not result in diminution of biologic response.

Regulation of cell surface receptors may also be accomplished by administration of receptor antagonists or agonists. Receptor antagonists are organic protein or peptide ligands generally derived through empirical structure-function studies, or through the use of detailed knowledge of ligand and receptor interaction. Essentially, an antagonist may constitute any molecule with similar binding activity to a natural ligand, but incapable of producing the biological response normally induced by the natural ligand. Thus, the antagonist competitively blocks receptor activity. With a competitive antagonist, the regulation of receptor activity is dependent upon both the antagonist's affinity for the receptor, as well as its extracellular concentration over time. Receptor agonists are protein or peptide ligands derived in a similar manner as antagonists. Essentially, an agonist may constitute any molecule which binds to the receptor in a manner superior to that of the natural ligand.

One receptor of particular interest is the vitamin B$_{12}$ receptor. As has been demonstrated in experimental in vitro data, pre-clinical animal models, and patient studies, vitamin B$_{12}$ is a co-enzyme necessary in cell division, as well as cellular metabolism, in proliferating normal and neoplastic cells. Insufficient vitamin B$_{12}$ causes cellular division to be held in abeyance and ultimately may result in apoptosis. The nutrient is generally derived from dietary intake and is transported throughout the body complexed to transport proteins. The complex of transport protein and vitamin B$_{12}$ is recognized by a cellular receptor which internalizes the complex and releases the vitamin intracellularly. The overall process has been reviewed in *GUT* 31:59, 1991. Vitamin B$_{12}$ is taken in through the diet. Binding proteins in the saliva (R-binder) and gut (intrinsic factor-(IF)) complex vitamin $B_{12}$ after release from endogenous binding proteins by action of enzymes and low pH in the stomach. Vitamin $B_{12}$ is transferred across the intestinal epithelium in a receptor specific fashion to transcobalamin II (TcII). The vitamin $B_{12}$/transcobalamin II complex is then transported throughout the body and recognized by receptors present on dividing cells, internalized and released within the cell where it is utilized by certain enzymes as a co-factor.

The high affinity receptor in dividing tissues or cells responsible for internalization of vitamin $B_{12}$ recognizes transcobalamin II complexed with vitamin $B_{12}$. The vitamin $B_{12}$/TcII receptor recognizes only the vitamin $B_{12}$/TcII complex and not the serum transport protein or the vitamin alone. The receptor is undetectable on non-dividing cells; the mechanism for supplying non-dividing cells with vitamin $B_{12}$ is poorly understood. However, it is known that more vitamin $B_{12}$ is required during cell division than during metabolism, and that the vitamin $B_{12}$/TcII receptor is the only high affinity means for cellular uptake of vitamin $B_{12}$ during cell division. When stimulated to divide, cells demonstrate transient expression of this receptor leading to vitamin $B_{12}$ uptake which precedes actual DNA synthesis (*J. Lab. Clin. Med.* 103:70, 1984). Vitamin $B_{12}$ receptor levels may be measured by binding of $^{57}Co$-vitamin $B_{12}$ complexed to transcobalamin II (present in serum) on replicate cultures grown in chemically defined medium without serum. No receptor mediated uptake occurs in the absence of carrier protein.

Dividing cells, induced to differentiate, lose receptor expression and no longer take up vitamin $B_{12}$. More importantly, leukemic cells, deprived of vitamin $B_{12}$, will stop dividing and die (*Acta Haemat.* 81:61, 1989). In a typical experiment, leukemic cell cultures were deprived of serum for 3 days, and then supplemented either with serum (a source of vitamin $B_{12}$) or a non-metabolizable analogue of vitamin $B_{12}$ and cultured up to five days. Cell cultures supplemented with vitamin $B_{12}$ continued to grow, whereas those deprived of the active nutrient stopped growing and die.

Based on these observations, it has been suggested that whole body deprivation of vitamin $B_{12}$ may be useful in the treatment of cancer or other disorders characterized by uncontrolled growth of cells. Moreover, because of the critical role played by vitamin $B_{12}$-containing enzymes in cell division, it is believed that vitamin $B_{12}$ deprivation may be used in combination with chemotherapeutic drugs which inhibit cellular replication. For example, when vitamin $B_{12}$ depletion was combined with methotrexate, the two modalities together were more efficient in depleting folate levels in leukemic cells than either alone (*FASEB J.* 4:1450, 1990; *Arch. Biochem. Biophys.* 270:729, 1989; *Leukemia Research* 15:165, 1991). Folates are precursors in the production of DNA and proteins. In typical experiments, cultures of leukemic cells were exposed to nitrous oxide for several hours to convert the active form of endogenous vitamin $B_{12}$ to an inactive form. Replicate cultures were then left without further treatment, or additionally treated with methotrexate. Cellular folate levels were measured three days later. Cells treated with the combination (i.e., both methotrexate and inactive vitamin $B_{12}$) showed a more striking decrease in cellular folate levels than with either of the two approaches alone. This combination also results in a higher cell kill in vitro. When this approach was applied to the treatment of highly aggressive leukemia/lymphoma in animal models (*Am. J. Haematol.* 34:128,1990; *Anticancer Res.* 6:737, 1986; *Cancer Chemother. Pharmacol.* 17:114, 1986; *Br. J. Cancer* 50:793, 1984), additive or synergy of anti-tumor action was observed, resulting in prolonged remissions and cures.

A key finding in the experiments described above was that short-term (hours to days), whole body depletion of vitamin $B_{12}$ can act synergistically with chemotherapeutic drugs (such as methotrexate and 5-FU) to inhibit tumor growth and treat animals with leukemia/lymphoma. Despite synergistic anti-tumor activity, there was no toxicity attributable to the short-term vitamin $B_{12}$ depletion for proliferating normal cells. This combination therapy was demonstrated in multiple animal models. Observations in patients have indicated that long-term (months to years) vitamin $B_{12}$ depletion is required to produce significant normal tissue toxicity. Even in those cases, subsequent infusion of vitamin $B_{12}$ can readily reverse symptomology (*Br. J. Cancer* 5:810, 1989).

Because of the promise of this therapeutic approach, various methods have been sought to efficiently and controllably perform a temporary depletion of vitamin $B_{12}$. Such methods, however, affect all of the body's stores of vitamin $B_{12}$. They include dietary restriction, high doses of vitamin $B_{12}$ analogues (non-metabolizable-competitive antagonists which act as enzyme inhibitors), and nitrous oxide (transformation of vitamin $B_{12}$ to inactivate form). These different methods have been used in culture systems and in animals to deplete vitamin $B_{12}$. The most efficient and the most utilized method has been the inhalation of nitrous oxide (laughing gas). Animals are maintained typically under an atmosphere of 50% to 70% of nitrous oxide for periods from a few hours to a few days, causing the conversion of endogenous vitamin $B_{12}$ into an inactive form. This methodology has been utilized in combination with drugs for therapy of leukemia/lymphoma. A further method for vitamin $B_{12}$ depletion involves infusion of a non-metabolizable analogue of vitamin $B_{12}$ which essentially dilutes out the active form. This form of therapy is not specific for dividing cells but affects liver dependent metabolic processes. Another approach includes restricting the dietary intake of vitamin $B_{12}$. This method, however, requires very long periods of dietary restriction and is offset by hepatic storage of vitamin $B_{12}$. All of these methods suffer from problems of specificity, since they affect both vitamin $B_{12}$-dependent growth as well as basal metabolism, and therefore are not particularly suited to the development of anti-proliferative pharmaceutical products.

In view of the biological importance of cell surface receptors, receptor-controlling agents have emerged as a class of pharmaceutical drugs. Moreover, with the advent of genetic engineering for the isolation and amplification of genes for cell surface receptors, as well as computer programs to model the interactions between ligands and receptors (i.e., "rational" drug design), the production of receptor-controlling drugs has been significantly enhanced.

To date, many months or even years of scientific research, as well as significant financial resources, are required to produce new receptor antagonists or agonists. To speed up this process, new screening technologies have been developed which utilize peptide or antibody recombinant libraries (see, e.g., *Gene* 73:305, 1988; *Proc. Nat. Acad. Sci. (USA)* 87:6378, 1990; *Biochromatography* 5:22, 1990; *Protein Engineering* 3:641, 1989). While library screening does not require the same degree of knowledge of a specific receptor/ligand system, it does involve an intensive screening effort utilizing functional receptor-specific assays. Moreover, the initial compounds identified by such screening programs are generally only precursors to the development of therapeutic products through more typical structure-functional assessments.

While antagonists and agonists are generally capable of regulating a biological response, the surface receptors which bind such ligands are continually being re-expressed on the cell surface. Thus, effective regulation by antagonists or agonists must rely on a relatively high and sustained serum concentration in order to bind the new surface receptors continually being expressed on the cell surface.

Accordingly, there is a need in the art for agents which bind cell surface receptors and thus regulate biological responses associated therewith, and which further effect normal cellular trafficking of the bound receptor. There is also a need in the art for agents which, when bound by a cell surface receptor and internalized, promote retention of the receptor within the cell. Moreover, there exists a need for methods relating to the administration of such agents to regulate a biological response. The present invention fulfills these needs and provides further related advantages.

SUMMARY OF THE INVENTION

Briefly stated, the present invention provides receptor modulating agents which are capable of affecting a receptor trafficking pathway of the cell. Receptor modulating agents of the present invention are comprised of a rerouting moiety coupled to a targeting moiety.

Suitable targeting moieties include, by way of example, a vitamin $B_{12}$ molecule or any one of several proteins and peptides described in detail below.

Suitable rerouting moieties include, by way of example, lysosomotropic moieties, such as gentamycin, kanamycin, neomycin, and streptomycin; intracellular polymerizing moieties, such as dipeptide esters and leucine zippers; peptide sorting sequences, such as endoplasmic reticulum retention peptides, golgi retention peptides, lysosomal retention peptides, organism specific retention peptides and clathrin-binding peptides; conditional membrane binding peptides, such as charged glutamate, aspartate, and histidine; and bi- or multi-valent receptor cross-inking moieties.

In a preferred embodiment of the present invention, a receptor modulating agent is comprised of a vitamin $B_{12}$ molecule coupled to a rerouting moiety by a linker. The length of the linker is dependent upon a number of empirical factors based on the nature of the receptor modulating agent and its component targeting and rerouting moieties. Suitable linkers include linkers which include an amino group, such as diaminoalkyl, diaminoalkylaryl, diaminoheteroalkyl, diaminoheteroalkylaryl and diaminoalkanes. In a preferred embodiment, the linker is —NH(CH$_2$)$_x$NH— wherein x=2–20 or —NH(CH$_2$)$_y$CO—, wherein y=3–12.

In one aspect of this embodiment, the linker is a water-solublizing linker, such as a linker containing ether and/or hydroxy groups. In yet another embodiment, the linker is a trifunctional linker.

In another aspect of this embodiment, a vitamin $B_{12}$ molecule is coupled to a rerouting moiety at a b-, d- or e-coupling site. In a particularly preferred embodiment of the present invention, a vitamin $B_{12}$ molecule is coupled to a rerouting moiety at a b- or e-coupling site. In another embodiment, the $B_{12}$ molecule is coupled to a rerouting moiety at a ribose coupling site. In yet another embodiment, the receptor modulating agent is bound to transcobalamin.

Receptor modulating agents of the present invention act by affecting a receptor trafficking pathway in any one of several ways, including, by redirecting an agent/receptor complex; by cross-linking one or more cell surface receptors; by anchoring a cell surface receptor in the membrane; and by retaining a receptor in an endosome.

Another aspect of the present invention includes a vitamin $B_{12}$ dimer comprising a first and a second vitamin $B_{12}$ molecule coupled through a coupling site independently selected from the group consisting of coupling sites a–g, coupling sites h, and coupling sites i. In a preferred embodiment, the $B_{12}$ molecule is coupled through an e- or b-coupling site. The vitamin $B_{12}$ molecules may be covalently coupled by the linkers of the present invention or through specific binding interactions such as avidin-biotin binding.

In another embodiment, the vitamin $B_{12}$ molecules are coupled by a linker. In a preferred embodiment, the linker is a trifunctional linker. Suitable linkers include linkers which include an amino group, such as diaminoalkyl, diaminoalkylaryl, diaminoheteroalkyl, diaminoheteroalkylaryl and diaminoalkanes. In another preferred embodiment, the linker is —NH(CH$_2$)$_x$NH— wherein x=2–20 or —NH(CH$_2$)$_y$CO—, wherein y=3–12. In yet another preferred embodiment, the linker is a water-solublizing linker, such as a linker containing ether and/or hydroxy groups.

In another aspect of this embodiment, a vitamin $B_{12}$ dimer is coupled to at least one transcobalamin II molecule. In yet another aspect of this embodiment, at least one of said first and said second vitamin $B_{12}$ molecules of the dimer is a vitamin $B_{12}$ derivative.

These and other aspects of the present invention will become evident upon reference to the following detailed description and attached drawings. In addition, various references set forth below which describe certain procedures or compositions in more detail are incorporated by reference in their entirety.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIGS. 2–5 are formulae representing families of antibiotics which act as rerouting moieties. The preferred reactive groups for coupling with a targeting moiety are indicated. These rerouting moieties facilitate retention of the receptor/receptor modulating agent complex through protonation of the complex, eventually delivering it to lysosomes for degradation.

FIG. 2 illustrates formulae representing the gentamycin, sisomicin, and netilmicin families of antibiotics.

FIG. 3 illustrates formulae representing the kanomycin, tobramycin, and amikacin families of antibiotics.

FIG. 4 illustrates formulae representing the neomycin, paromomycin, ribostamycin, and butirosin families of antibiotics.

FIG. 5 illustrates formulae representing the streptomycin family of antibiotics.

FIG. 8 illustrates a formula representing a vitamin $B_{12}$ (cyanocobalamin) molecule and identifies a preferred coupling site suitable for use in the present invention for derivatization and conjugation.

DETAILED DESCRIPTION

Figure 1:
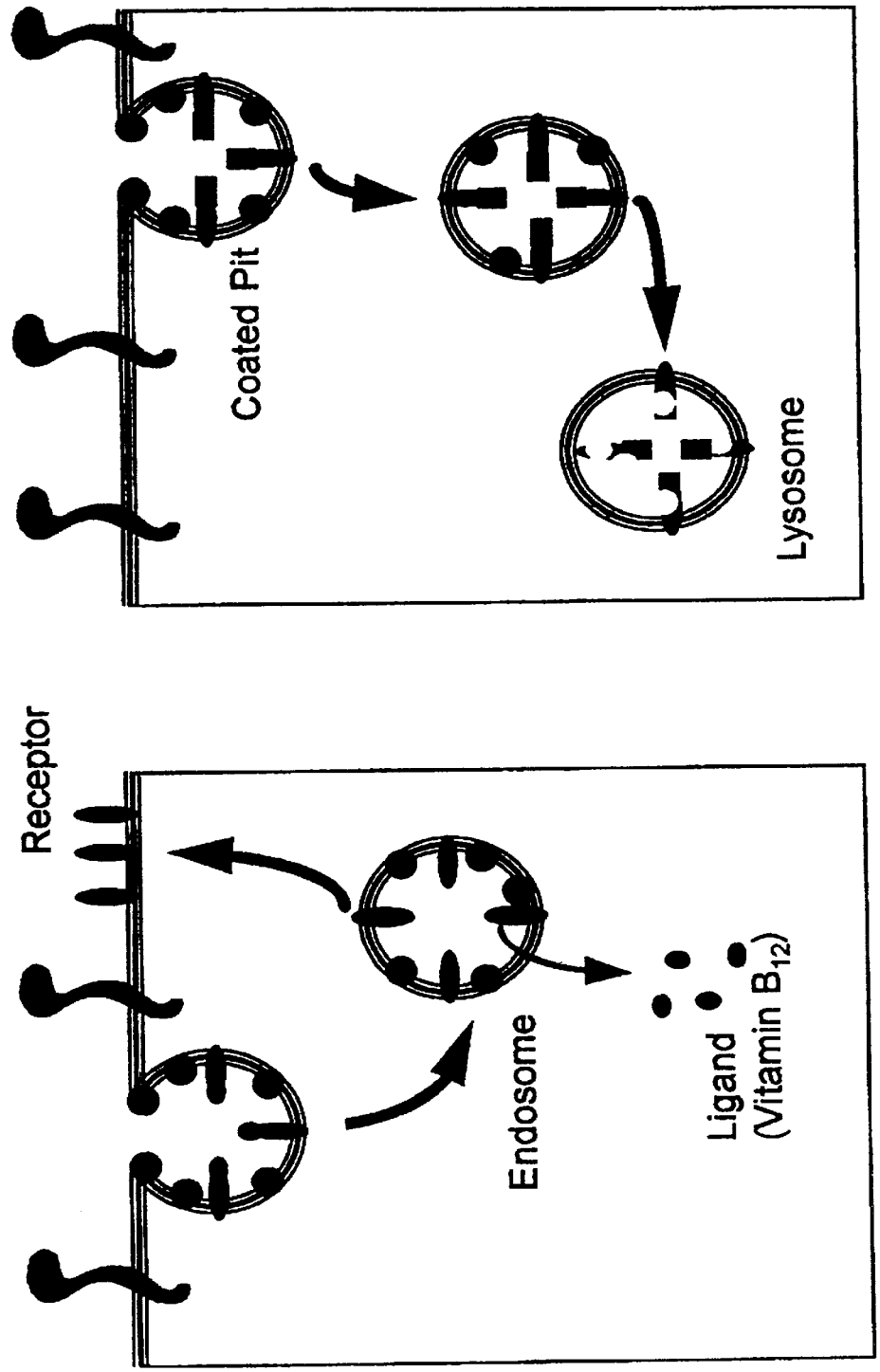
FIG. 1 is a schematic illustrating a mechanism of action of a receptor modulating agent of the present invention. A healthy receptor will internalize when bound by the appropriate ligand, release the ligand within the cell and then recycle to the cell surface. Receptor modulating agents of the present invention impede the receptor trafficking pathway by inhibiting the recycling of receptors to the cell surface. Essentially, the targeting moiety on receptor modulating agents bind the receptor and the rerouting moiety redirects the receptor/receptor modulating agent complex to other points within the cell, where it may be retained or degraded. (Not shown in this schematic are receptors synthesized de novo).

The present invention is generally directed to a receptor modulating agent which is capable of binding to a cell surface receptor to form a receptor modulating agent/receptor complex ("agent/receptor complex"). The binding of a suitable receptor modulating agent to a cell surface receptor generally results in invagination of the agent/receptor complex into the cell into the vesicular system in the same manner as the natural ligand. However, once internalized, or as part of the internalization process, a receptor modulating agent of the present invention affects the receptor trafficking pathway by effectively impeding, preventing, or delaying the receptor from recycling to the surface, thus depriving the cell of receptors able to engage in binding its natural ligand and triggering related biological responses.

Within the context of the present invention, "affecting the receptor trafficking pathway" refers to impeding the receptor trafficking pathway in such a manner so as to affect biological response. This would include trapping, delaying, retaining, re-directing, or degrading the cell surface receptor. A "receptor modulating agent" is comprised of at least one targeting moiety covalently attached to at least one rerouting moiety. A "targeting moiety," as described in detail below, is a moiety capable of specifically binding to a cell surface receptor to yield an agent/receptor comliex and, in a preferred embodiment, has an affinity for the cell surface receptor of within 100-fold, and more preferably, within 10-fold, of the affinity of the natural ligand for the receptor. A preferred targeting moiety is a vitamin $B_{12}$ molecule. In contrast, a "rerouting moiety" is a moiety which redirects an agent/receptor complex, resulting in prolonged retention, degradation, and/or modulation of the receptor within the interior of a cell or on the cell surface, including, by way of example, retaining the receptor in the cell membrane or directing the receptor to a lysosome within the cell. Suitable rerouting moieties are described in detail below.

A targeting moiety is coupled to a rerouting moiety to yield the receptor modulating agent by any suitable means known in the art, including direct covalent linkage of an appropriate chemical linker or through a very tight association in non-covalent attachment. By way of example for the latter, in one embodiment, coupling is accomplished through the combination of an avidin or streptavidin conjugate with a vitamin $B_{12}$/biotin conjugate. Coupling of the targeting moiety and the rerouting moiety should be of a nature which resists cleavage by the enzymatic and low pH conditions normally encountered within the internal portion of the cell, including endosomes and lysosomes. Suitable linkers are noted below. The ability to resist cleavage may be detected by any means known in the art, including exposing the receptor modulating agent to enzymes at low pH and measuring release of the targeting or rerouting moiety using techniques known in the art.

Coupling of a targeting moiety and a rerouting moiety should not significantly hinder the ability of the targeting moiety to specifically bind the cell surface receptor. The receptor modulating agent may also include additional moieties, so long as they do not interfere with either the targeting or the rerouting moieties. For example, such moieties may be coupled to the receptor modulating agent through the use of a trifunctional linker or they may be coupled to a rerouting or targeting moiety. Optimal attachment of the two moieties may be determined by comparing the affinity of binding of the receptor modulating agent with free targeting moiety in assays of inhibition of binding.

These, and other suitable techniques, are described in detail in Sambrook et al., *Molecular Cloning: A Laboratory Manual*, Cold Spring Harbor, 1989.

Coupling of a targeting moiety and a rerouting moiety should also not significantly affect the ability of the rerouting moiety to retain or delay the agent/receptor complex within the cell. This may be empirically determined by any one of several methods known in the art, including using labeling techniques to compare intracellular retention of the targeting moiety versus that of the receptor modulating agent as exemplified below.

As noted above, targeting moieties of a receptor modulating agent include any moiety which specifically binds to a cell surface receptor. Suitable targeting moieties include proteins and peptides. Representative examples of suitable targeting moieties include peptides such as bombesin, gastrin-releasing peptide, cell adhesion peptides, substance P, neuromedin-B, neuromedin-C and metenkephalin; hormones, including EGF, alpha- and beta-TGF, estradiol, neurotensin, melanocyte stimulating hormone, follicle stimulating hormone, luteinizing hormone, and human growth hormone; proteins corresponding to ligands for known cell surface receptors, including low density lipoproteins, transferrin and insulin; fibrinolytic enzymes; and biological response modifiers, including interleukin, interferon, erythropoietin and colony stimulating factor also constitute targeting moieties of this invention. Moreover, analogs of the above targeting moieties that retain the ability to specifically bind to a cell surface receptor are suitable targeting moieties. Essentially, any analog having about the same affinity as a targeting moiety, herein specified, could be used in synthesis of receptor modulating agents.

In a preferred embodiment, a targeting moiety is a vitamin $B_{12}$ molecule. Vitamin $B_{12}$ is an essential nutrient for dividing cells. By inhibiting its uptake, the growth of dividing cells can be halted. The cell surface receptor for vitamin $B_{12}$ is the transcobalamin II/vitamin $B_{12}$ ("TcII/$B_{12}$") receptor, which is characterized by a high affinity for the carrier protein, transcobalamin II (TcII), when complexed with vitamin $B_{12}$ ("TcII/$B_{12}$ complex"). The TcII/$B_{12}$ receptor does not recognize vitamin $B_{12}$ alone, but does recognize the carrier protein TcII with reduced affinity when not complexed with vitamin $B_{12}$. In many respects, this receptor system is similar to that for transferrin/iron in that the goal of the receptor system is to deliver vitamin $B_{12}$ into cells such that it can be utilized by enzymes involved in DNA synthesis. Within the context of the present invention, the term "vitamin $B_{12}$" refers to the class of compounds known as cobalamins and derivatives thereof, including, by way of example, cyanocobalamin. The term "vitamin $B_{12}$" is used interchangeably with the term cyanocobalamin.

Suitable vitamin $B_{12}$ molecules includes any vitamin $B_{12}$ capable of coupling to another molecule while maintaining its ability to form a TcII/$B_{12}$ complex. A preferred vitamin $B_{12}$ targeting moiety is generally comprised of a vitamin $B_{12}$ molecule, such as a cyanocobalamin, and a linker, described in detail below. The linker may be coupled to any one of several sites on a vitamin $B_{12}$ molecule, including potential carboxyl coupling sites a- through g-, an alcohol (ribose) coupling site ("coupling site h") or a benzimidazole coupling site ("coupling site i.") (See structure I below.) Preferably, a linker is coupled to coupling sites h-, d- or e- on a vitamin $B_{12}$ molecule. Even more preferably, a linker is coupled to coupling site d- or e-. This embodiment of the present invention includes compounds represented by the following formula:

STRUCTURE I 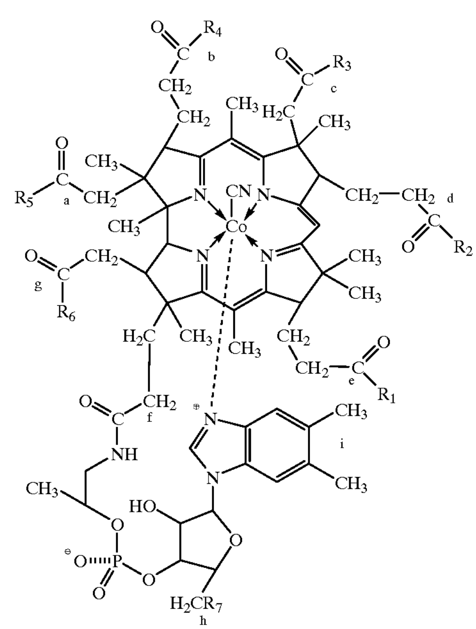 wherein at least one of $R_1$, $R_2$, $R_3$, $R_4$, $R_5$, $R_6$, and $R_7$ is a linker. One of ordinary skill in the art will appreciate that a number of other coupling sites on the vitamin $B_{12}$ molecule may be chemically altered without affecting coupling of the molecule with a linker or TcII. Coupling sites which are not occupied by a linker may have a variety of chemical moieties attached thereto, including an amino, secondary amino, tertiary amino, hydroxy, lower alkyl, lower alkoxy, alkoxyalkyl, alkoxyalkoxy, cycloalkylalkoxy, and thioalkyl groups.

In a preferred embodiment, $R_1$, $R_2$ or $R_4$ is a linker and the remaining R groups are $-NH_2$, with the exception of $R_7$, which is preferably $-OH$. In an especially preferred embodiment, $R_2$ is a linker, $R_1$, $R_3-R_6$ are $-NH_2$ and $R_7$ is $-OH$.

In another preferred embodiment, $R_7$ is a linker and $R_1-R_6$ are $-NH_2$.

TABLE 1

HOMOBIFUNCTIONAL LINKERS

| Structure | Name |
|---|---|
| | disuccinimidyl suberate (DSS)* |
| | bis(sulfosuccinimidyl) suberate (BS³)* |
| | disuccinimidyl suberate (DSS)* |
| | bis(sulfosuccinimidyl) suberate (BS³)* |
| | disuccinimidyl tartarate (DST)* |
| | disulfosuccinimidyl tartarate (Sulfo-DST)* |
| | bis[2-(succinimidooxycarbonyloxy)ethyl] sulfone BSOCOES)* |

TABLE 1-continued

HOMOBIFUNCTIONAL LINKERS

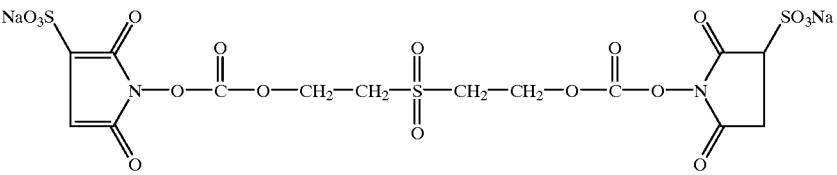

bis[2-(sulfosuccinimidooxycarbonyloxy)ethyl]sulfone (Sulfo-BSOCOES)*

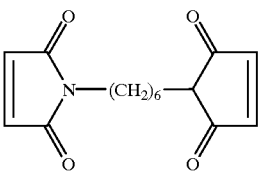

bismaleimidohexane (BMH)*

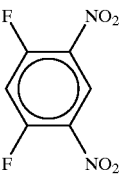

1,5-Difluoro-2,4-dinitrobenzene (DFDNB)*

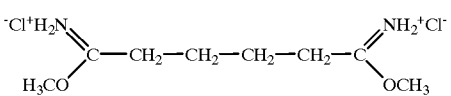

dimethyl adipimidate-2 HCl (DMA)*

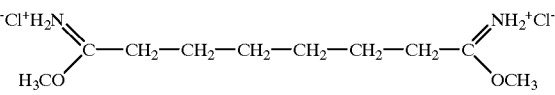

dimethyl pimelimidate-2 HCl (DMP)*

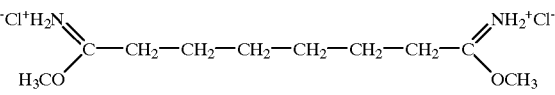

dimethyl subevimidate-2 HCl (DMS)*

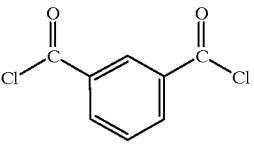

isophthaloyl dichloride**

*Pierce Chemical, Co., Rockford, Illinois
**Aldrich Chemical Co., Milwaukee, Wisconsin

TABLE 2

HETEROBIFUNCTIONAL LINKERS

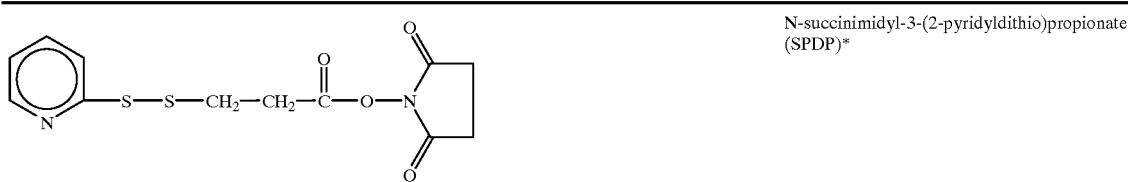

N-succinimidyl-3-(2-pyridyldithio)propionate (SPDP)*

TABLE 2-continued

HETEROBIFUNCTIONAL LINKERS succinimidyl 6[3(2-pyridyldithio)propionamido]hexanoate (LC-SPDP)* sulfosuccinimidyl 6-[3-(2-pyridyldithio)propionamido]hexanoate (Sulfo-LC-SPDP)* succinimidyl 4-(N-maleimidomethyl)cyclohexane-1-carboxylate (SMCC)* sulfosuccinimidyl 4-(N-maleimidomethyl)cyclohexane-1-carboxylate (Sulfo-SMCC)* m-maleimidobenzoyl-N-hydroxysuccinimide ester (MBS)* m-maleimidobenzoyl-N-hydroxysulfosuccinimide ester (Sulfo-MBS)*

N-succinimidyl(4-iodoacetyl)aminobenzoate (SIAB)*

TABLE 2-continued

HETEROBIFUNCTIONAL LINKERS

| Structure | Name |
|---|---|
| (iodoacetyl-aminobenzoate with sulfo-NHS ester) | sulfosuccinimidyl(4-iodoacetyl)aminobenzoate (Sulfo-SIAB)* |
| (NHS-ester-propyl-phenyl-maleimide) | succinimidyl-4-(p-maleimidophenyl)butyrate (SMPB)* |
| (sulfo-NHS-ester-propyl-phenyl-maleimide) | sulfoccinimidyl-4-(p-maleimidophenyl)butyrate (Sulfo-SMPB)* |

*Pierce Chemical, Co., Rockford, Illinois

TABLE 3

TRIFUNCTIONAL LINKERS

| Structure | Description |
|---|---|
| 5-NHBoc-1,3-bis(CO$_2$TFP)benzene | Derived from 5-amino isophthalic* acid- unreported synthesis (D. S. Wilbur, D. K. Hamlin, University of Washington) |
| 3,5-diamino-benzoic acid methyl ester | Derived from 3,5-diaminovbenzoic acid*- unreported synthesis |
| 5-(p-iodobenzoyl)amino-1,3-bis(CO-OTFP)benzene | 5-(p-iodobenzoyl)amino-1,3-isophthaloyl ditetra-fluorophenyl ester - unreported synthesis (D. S. Wilbur, D. K. Hamlin, University of Washington) |

TABLE 3-continued

TRIFUNCTIONAL LINKERS

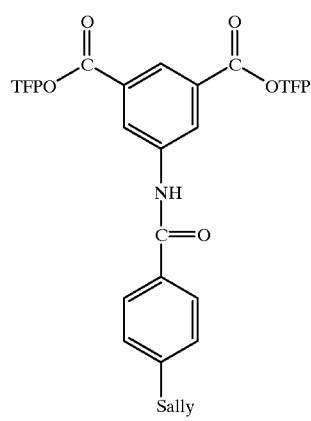

5-(p-tri-N-butylisomylbenzoyl)-amino-1,3-isophthaloyl ditchtrafluorophenyl ester - unreported synthesis (D. S. Wilbur, D. K. Hamlin, University of Washington)

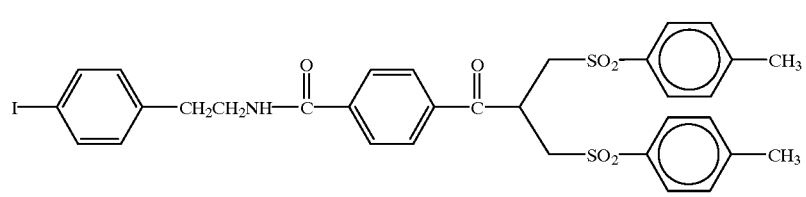

D. S. Wilbur, et al., Bioconjugate Chem. 5(3):220–235, 1994.

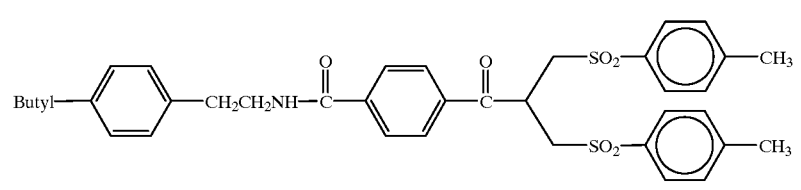

D. S. Wilbur, et al., Bioconjugate Chem. 5(3):220–235, 1994.

*Aldrich Chemical Co., Milwaukee, Wisconsin

Suitable linkers include any of several linkers, preferably containing at least two coupling or reactive groups, allowing the linker to bind to both vitamin $B_{12}$ and a rerouting moiety. In the context of the present invention, the terms "coupling group" and "reactive group" are used interchangeably. By way of example, a linker may be homobifunctional, heterobifunctional, homotrifunctional, or heterotrifunctional. Homobifunctional agents may facilitate cross-inking, or dimerization of vitamin $B_{12}$ molecules in a single step, hence a coupling reaction using these agents should be performed with an excess of homobifunctional agents, unless dimerization is the desired result, as in the synthesis of dimers described in detail below.

Suitable homobifunctional agents include those listed in Table 1, as well as those described in detail below. Heterobifunctional agents facilitate cross-linking in a stepwise method, allowing more than one linker to be incorporated and a variety of targeting agents such as vitamin $B_{12}$ molecules to be linked. Suitable heterobifunctional agents include those listed in Table 2 as well as those described in detail below. Homo- and hetero-trifunctional linkers are coupled to a rerouting moiety and a vitamin $B_{12}$ molecule as described above, with the additional advantage of a third coupling site on the linker. One of ordinary skill in the art will appreciate that this allows for any number of different molecules to couple with the rerouting moiety, including, by way of example, markers, such as radiolabeled and fluorescent molecules; proteins and peptides, such as antibodies; and conjugating molecules, such as biotin. Suitable trifunctional linkers are listed in Table 3. Homobifunctional, heterobifunctional, homotrifunctional, and heterotrifunctional linkers are commercially available.

The preferred length of a linker is dependent upon a number of empirical factors based upon the nature of the receptor modulating agent including its component targeting and rerouting moieties. In general, a linker should have a length sufficient such that the targeting moiety and the rerouting moiety of the receptor modulating agent may perform their designed functions free from steric inhibition. There are three primary areas of function which must be taken into consideration: (1) binding of the rerouting moiety to the targeting moiety, (2) binding of other molecules, such as TcII on the targeted receptor, to the receptor modulating agent and (3) ability to interfere with the receptor trafficking. By way of example, a linker should have a length sufficient to facilitate the specific binding of a targeting moiety to a cell surface receptor to yield an agent/receptor complex. Additionally, a linker should also have a length sufficient to permit a rerouting moiety to redirect an agent/receptor complex so as to interfere with the receptor trafficking pathway. Thus, empirical factors such as the size (e.g., molecular weight and molecular conformation) and the nature (e.g., charge and constituency) of receptor modulating agents, linkers, targeting moieties, cell surface receptors, rerouting moieties, and the receptor trafficking pathway will all affect the length of the Linker.

By way of specific examples, linkers for vitamin $B_{12}$ receptor modulating agents should have a length sufficient to allow for binding of a vitamin $B_{12}$ derivative to transcobalamin II to form a TcII/$B_{12}$ complex, and subsequently, to permit the binding of a TcII/$B_{12}$ complex to a TcII/$B_{12}$ cell surface receptor. Linkers for receptor modulating agents including a biotin moiety should be of a length sufficient to facilitate binding of the receptor modulating agent to avidin (or streptavidin).

Suitable linkers are generally relatively linear molecules greater than 4 atoms in length typically between 6 and 50 atoms in length, and preferably are 8 to 35 atoms in length. In one preferred embodiment, the linker is a linear molecule of 12–15 atoms in length. In the context of the present invention, the term "atom" refers to a chemical element such as, by way of example, C, N, O, or S. The ranges provided above are based on the relatively linear accounting of the linker. One of ordinary skill in the art will appreciate that a linker may be linear, branched, and even contain cyclical elements.

In another aspect of the present invention, the linker is a water-solubilizing linker. The term "water-solubilizing linker" refers to any linker that, when covalently coupled to a rerouting and/or targeting moiety, increases the water solubility of either the components or the receptor modulating agent. The term "water solubility" refers to solubility in water or any other aqueous medium. In general, the solubility of a compound may be determined as described in "Handbook of Solubility Parameters and Other Cohesion Parameters" by A. F. M. Benton, CRC Press, 1983. The water-solubilizing linkers may also enhance the water solubility of the receptor modulating agents.

The water-solubilizing linkers are composed of hydrophilic moieties (e.g., polar functional groups) including electronically neutral and charged (i.e., ionic) moieties. Suitable hydrophilic moieties include electronically neutral moieties containing polar functional groups (ie., groups which contain atoms of differing electronegativities such as organic compounds containing nitrogen, oxygen, and sulfur) which increase their hydrophilicity. Typically, these neutral hydrophilic moieties contain functional groups which hydrogen bond with water. Such hydrogen bonding groups include ether (—O—), hydroxy (—OH), amino (—$NR_2$, —NHR, —$NH_2$), and to a lesser extent thioether (—S—), and thiol (—SH) groups.

Other polar functional groups which may serve as hydrophilic moieties include ethers and carbonyl containing groups such as acids, esters, amides, ketones, and aldehydes. Moieties which contain multiple polar functional groups are more hydrophilic than those moieties which contain a single polar functional group. Suitable moieties that contain multiple polar groups include, by way of example, polyhydroxy, polyamino, polyether, polyphosphoric acid, polyalcohol and polyamine moieties. Polyhydroxy moieties include, by way of example, glycols, glycerols, and polysaccharides including glucose, fructose, galactose, idose, inositol, mannose, tagatose, and N-methylglucamine. Polyalcohol moieties include, by way of example, N-methylglucamine and glucose derivatives. Polyether moieties include, by way of example, polyethylene glycol, ethoxy ethanol, and ethoxy ethoxy ethanol. Polyamine moieties include, by way of example, spermine or spermidine.

Suitable charged hydrophilic moieties include those moieties which become either formally negatively or positively charged in water. Suitable negatively charged moieties include acid anions resulting from the dissociation of acids in water. For example, carboxylic acids (—$CO_2H$) dissociate to form negatively charged carboxylate ions (—$CO_2$—) at pH greater than about 5. Other stronger acids such as phosphoric (—$PO_3H_2$) and sulfonic (—$SO_3H$) acids ionize to form phosphonate (—$PO_{32}$—) and sulfonate (—$SO_3$—) anions, respectively at pH greater than about 2. Other more weakly acidic moieties such as phenols and thiols may also dissociate to form their corresponding anionic derivatives which are also water solubilizing. Depending upon the pH of the aqueous solution, basic moieties may become formally positively charged moieties in water. These moieties become highly water soluble through protonation in aqueous solution. For example, at pH about 5, amines (—$NR_2$, —NHR, —$NH_2$) become ammonium ions (—$NHR_2^+$, —$NH_2R^+$, —$NH_3^+$), all of which are highly water solubilizing moieties. Quaternary ammonium moieties (—$NR_3^+$) are extremely water solubilizing at all pHs. Suitable charged solubilizing moieties also include polylysine groups.

The water solubility of a vitamin $B_{12}$ derivative may be evaluated by any one of several means, including, by way of example, simply combining the derivative with an aqueous medium and observing the solubility at various temperatures. Alternatively, solubility may be ascertained by dissolving the derivative in water stirring the solution and allowing the solution to stand at room temperature for about 24 hours. The solution is then centrifuged and the resultant aqueous layer analyzed using high pressure liquid chromatography ("HPLC"). The HPLC analysis was conducted isocratically using acetonitrile as the solvent on a LiChrospher 100, C-18 column (5 $\mu$M, 125×4 mm) using a flow rate of 2 ml/min.

The quantitation of a vitamin $B_{12}$ containing solution may be accomplished by BPLC using UV detection. In the quantitation, an aqueous solution of a vitamin $B_{12}$ derivative is prepared and analyzed by HPLC as described above. A series of vitamin $B_{12}$ aqueous solutions of known concentration are prepared and analyzed by HPLC. The results of these HPLC analyses are then used to construct a standard curve where the concentration of the vitamin $B_{12}$ standard is plotted against the HPLC signal for the standard. Once a such standard curve has been constructed, aqueous solutions of various vitamin $B_{12}$ derivatives may be similarly analyzed and the concentration of the derivative in the solution determined.

Alternatively, the water solubility of a vitamin $B_{12}$ derivative (i.e., the concentration of a vitamin $B_{12}$ derivative) may be determined directly by absorbance spectroscopy. Briefly, a known amount of vitamin $B_{12}$ is dissolved in a known amount of water to provide an aqueous solution of known concentration (e.g., 10 mg derivative/10 mL water). The absorbance of this solution (or dilutions of the solution) is then measured by a UV absorbance spectrophotometer. The absorbance of the solution of known concentration provides the vitamin $B_{12}$ is derivative's absorptivity. Once the vitamin $B_{12}$ derivative's absorptivity has been determined in this manner, the concentration (or the amount of the vitamin $B_{12}$ derivative in the solution) of subsequent aqueous solutions of the vitamin $B_{12}$ derivative may be determined by measuring the absorbance of the solution.

In a preferred embodiment, the water-solubilizing linker is a polyether or a polyhydroxy linker. In a particularly preferred embodiment, the water-solubilizing linker is the polyether linker such as a 4,7,10-trioxa-1,13-tridecanediamine linker or a 3,6-dioxa- 1,8-octanediamine linker. The synthesis of a representative vitamin $B_{12}$ derivative having water-solubilizing linker is described in Example 23. The synthesis of a representative vitamin $B_{12}$-biotin conjugate having a water-solubilizing linker is described in Example 24. The syntheses of representative vitamin $B_{12}$ dimers having water-solubilizing linkers is described in Example 25. Coupling or reactive groups include any functional group capable of coupling a linker to a vitamin $B_{12}$ molecule. Suitable coupling groups include, nucleophilic and electrophilic functional groups. Suitable nucleophilic groups include hydroxy groups, amino groups, and thio groups. Suitable electrophilic groups include carboxylic acid groups and carboxylic acid derivatives including acid halides, acid anhydrides, and active esters such as NHS esters.

Suitable homobifunctional linkers include, by way of example, diaminoalkanes, such as those represented by the formula $NH_2(CH_2)_xNH_2$, wherein x=2–20. A preferred linker is a diaminododecane. Suitable heterobifunctional linkers include those represented by the formula $NH_2(CH_2)_yCOOH$, wherein y=3–12. Those of ordinary skill in the art will appreciate that a protecting group may be necessary when utilizing a heterobifunctional group.

A linker may be coupled to the preferred b-, d- or e-coupling sites (see Structure I above) by any one of several suitable means, including, by way of example, activating a vitamin $B_{12}$ molecule by hydrolyzing its propionamide groups to produce monocarboxylates, purifying the resulting monocarboxylates, and coupling a linker to a selected coupling site. Hydrolysis of the coupling sites may be accomplished by exposing vitamin $B_{12}$ to aqueous acid for a period of time and under suitable conditions to hydrolyze the desired propionamide groups. Preferably, hydrolysis is performed by exposure of the amide to dilute aqueous acid for a period of about 6 to 12 days, typically about 9 to 11 days, and most preferably about 10 days at room temperature. Suitable aqueous acids include, by way of example, 0.1N hydrochloric acid, 0.5N phosphoric acid or 0.5N sulfuric acid.

Purification of b-, d- and e-monocarboxylates can be accomplished by any one of several means, including column chromatography, such as gel permeation chromatography, adsorption chromatography, partition chromatography, ion exchange chromatography, and reverse phase chromatography. Preferably, column chromatography is preparative reverse phase liquid chromatography. These techniques are described in detail in Lim, *BPLC of Small Molecules*, IRL Press, Washington, D.C., 1986. Purification of monocarboxylates by preparative liquid chromatography (LC) should be accomplished at a very slow flow rate. For example, LC purification may be conducted at a flow rate of 0.15 mL/min. on a 5 $\mu$m, 4.6×250 mm propylamine column (RAININ microsorb-MV amino column) eluting with 58 $\mu$M pyridine acetate, pH 4.4 in $H_2O$ THF (96:4) solution. Even more preferably, the coupling reaction is monitored using analytical high pressure liquid chromatography (HPLC). Reverse-phase HPLC chromatography is preferably carried out using an analytical version of above-noted propylamine column using a gradient solvent system at a flow rate of 1 mL/min. Within the context of the present invention, the d-isomer is identified as the longest retained peak (third), the e-isomer is identified as the second retained peak, and the b-isomer is identified as the shortest retained peak (first) eluted from the LC column. The e-isomer may also be identified as that vitamin $B_{12}$ derivative demonstrating the greatest biological activity as noted below.

A ribose coupling site (coupling site h, see structure I) may be activated by any one of several suitable means including, activating a hydroxyl group at coupling site h by reaction with a suitable reagent (e.g., succinic anhydride), to yield a ribose derivative which bears a reactive group (e.g., a carboxylate group). The term "ribose coupling site" and "coupling site h" are used interchangeably. This technique is described in detail in Toraya, *Bioinorg. Chem.* 4:245–255, 1975. Separation and purification of the activated molecule may be accomplished on a C18 column as noted below. Once coupling site h has been activated, a linker may be coupled to this site in the same manner as described below.

Preferably, a 5'-OH ribose coupling site is activated using any one of several suitable reagents including esterifying agents and ether forming reagents. These suitable reagents provide a cyanocobalamin derivative having a reactive group for further coupling reactions.

Esterification of the ribose 5'-OH may be accomplished with esterifying agents including, by way of example, carboxylic acid derivatives such as anhydrides, acid halides, and reactive esters including TFP and NHS esters. For example, treatment with succinic anhydride provides a 5'-O-ribose ester derivative having a carboxylic acid group as a reactive group for subsequent coupling reactions. Similarly, treatment with a suitable N-protected reactive ester of 4-aminobutyric acid (GABA) yields a 5'-O-ribose ester derivative having, after N-deprotection, an amino group as a reactive group for subsequent coupling reactions.

Suitable 5'-O-ribose ether derivatives may be prepared by any one of several methods including by activation of the 5'-OH followed by nucleophilic displacement. In one representative method, the 5'-OH group may be first converted to a good leaving group (e.g., a p-toluenesulfonic acid group) followed by displacement with a suitable nucleophile. Suitable nucleophiles include alcohol, amine, and sulfhydryl derivatives which produce 5'-O-ribose ether, amine, and thioether derivatives, respectively. Suitable alcohol, amine, and sulfhydryl derivatives include those derivatives having a reactive group such as a carboxylic acid or amine group, protected as necessary, for subsequent coupling reactions. By way of example, suitable ether forming reagents include N-protected alcohols, monoprotected diamines, and N-protected thioamines. Accordingly, depending upon the selection of the ether forming reagent, ether linkages including alkyl ether, and benzyl ether linkages may be formed.

Suitable 5'-O-ribose ether derivatives may also be prepared by 5'-OH alkylation with suitable alkylating agents. Suitable alkylating agents include alkylating agents having a reactive group such as a carboxylic acid or amine group, protected as necessary, for subsequent coupling reactions. Preferred alkylating agents include active halide compounds such as haloacetates, benzyl halides, and silyl halides. Alkylation with a haloacetate such as methyl bromoacetate or trimethylsilyl bromoacetate, or a benzyl halide such as methyl 4-(bromomethyl)benzoate provide 5'-O-ribose ethers (i.e., alkyl and ether linkages) having, after ester hydrolysis, a carboxylic acid group for subsequent coupling reactions. Alkylation with a silyl halide such as methyl 11-(chlorodimethylsilyl)undecanoate provides a 5'-O-ribose silyl ether (i.e., a silyl ether linkage) having, after hydrolysis, a carboxylic acid group for subsequent coupling reactions. The synthesis of a representative 5'-O-ribose ether derivative by alkylation with methyl bromoacetate is described in Example 26.

After activating the vitamin $B_{12}$ molecule at a selected coupling site, linkers may be coupled to a vitamin $B_{12}$ molecule to form a vitamin $B_{12}$ linker adduct using any one of several means, including, by way of example, an amide forming reaction, employing an amine group on the linker and a carboxylate coupling site on a vitamin $B_{12}$ molecule. Alternatively, a linker may be coupled to a vitamin $B_{12}$ molecule through an amide forming reaction, employing a carboxylate group on the linker and an amino group on a $B_{12}$ molecule. The amide forming reaction may include the use of a coupling agent. Suitable coupling agents include carbodiimide coupling agents, such as, by way of example, 1-ethyl-3-(3-dimethylamninopropyl) carbodiimide hydrochloride (EDC), 1-benzyl-3-(3-dimethylaminopropyl) carbodiimide (BDC), 1-cyclohexyl-3-(2-morpholinyl-4-ethyl) carbodiimide (CMC), and 1,3-dicyclohexylcarbodiimide (DCC). Preferably, the coupling agent is water soluble. Even more preferably, the coupling agent is EDC.

Alternatively, the amide forming reaction coupling the linker to a $B_{12}$ molecule may employ a reactive carboxylic acid group and an amine. Suitable reactive carboxylic acid groups include carboxylic acid derivatives which yield an amide upon reaction with an amine. Such reactive groups include, by way of example, any reactive carboxylic acid derivative, including, by way of example, carboxylic acid halides, such as acid chlorides and bromides; carboxylic acid anhydrides, such as acetic anhydrides and trifluoroacetic anhydrides; esters, such as p-nitrophenyl esters and N-hydroxysuccinimide esters. Such techniques are described in detail in Bodanszky, *Principles of Peptide Synthesis*, Springer Verlag, Berlin, 1984.

Although coupling of a linker through a cyano coupling site is possible it is not preferred, due to the instability of linkers coupled to this site. Dolphin, D., [205] *Methods Enzmol.* 18C:34–52, 1971. Additionally, a linker may be coupled to a benzimidazole (coupling site i, see Structure I) using techniques described in detail in Jacobsen, *Anal. Biochem.* 113:164–171, 1981.

Vitamin $B_{12}$ linker adducts may be separated and purified using any suitable means, including column chromatography, such as gel permeation chromatography, adsorption chromatography, partition chromatography, ion exchange chromatography, and reverse phase chromatography. Preferably, column chromatography is preparative LC. These techniques are described in detail in Lim, *HPLC of Small Molecules*, IRL Press, Washington, D.C., 1986.

As noted above, the vitamin $B_{12}$ receptor modulating agents of the present invention must be capable of binding transcobalamin II. The ability of a receptor modulating agent to bind TcII may be ascertained using any one of several means known in the art, including competitive binding assays with the receptor modulating agent competing with native vitamin $B_{12}$.

Rerouting moieties of the present invention include any moiety which is capable of affecting the receptor trafficking pathway. This characteristic can be assessed by employing a receptor modulating agent having a radiolabeled targeting moiety and following its path through the cell. This is accomplished using techniques known in the art, including using radiolabeled, biotinylated, or FITC labeled targeting moiety followed by binding assays, ELISA, or flow cytometry. A preferred receptor modulating agent is one which results in the removal of the highest percent of receptor for the longest period of time.

Suitable rerouting moieties of this invention do not significantly detract from the selectivity of the targeting moiety. Whether a rerouting moiety detracts from the selectivity of a targeting moiety may be determined by any one of several methods known in the art, including comparing binding of the receptor modulating agent on receptor positive and receptor negative cells, as assessed by ELISA, flow cytometry, or other binding assays.

Figure 5:
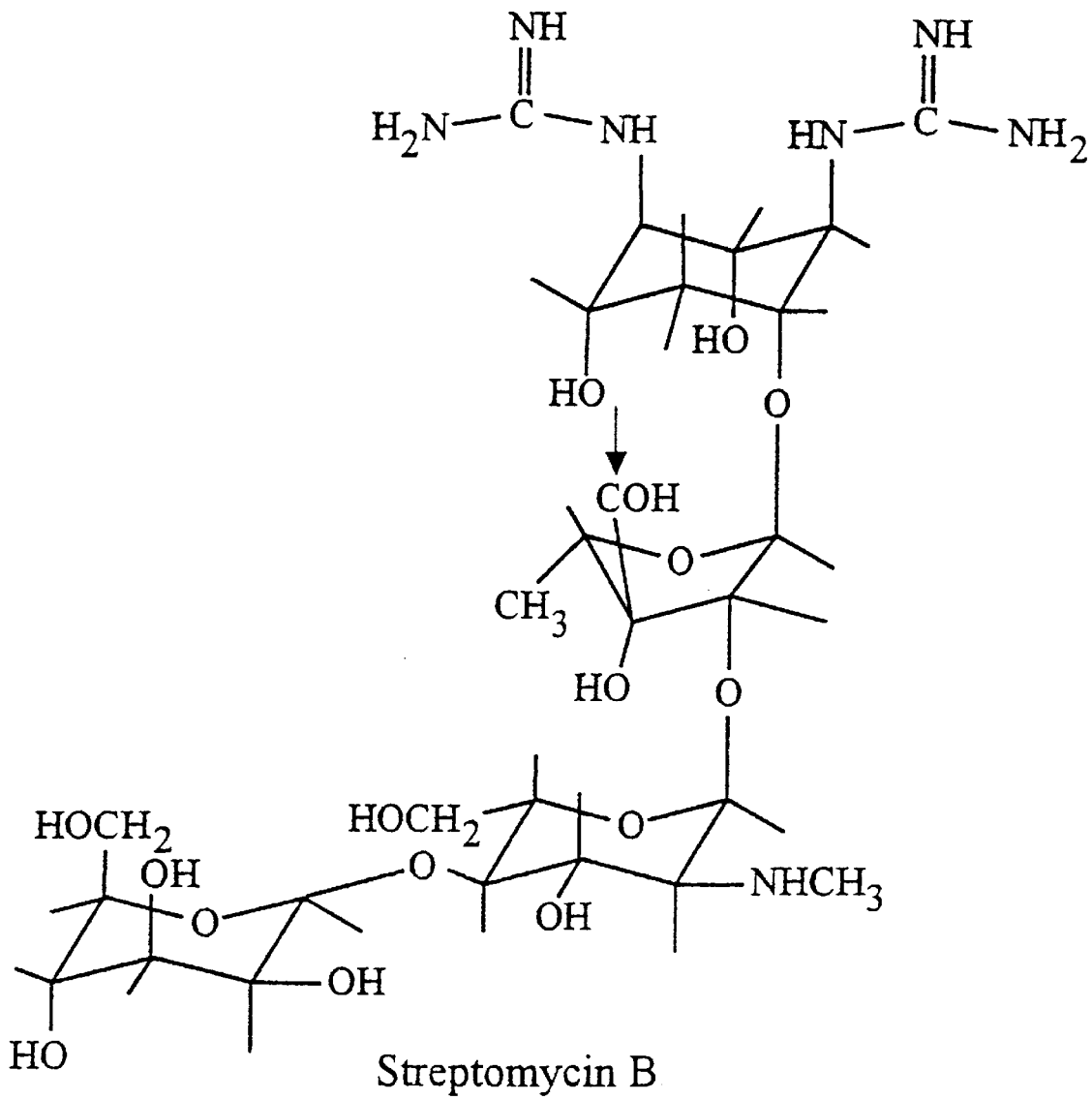

Rerouting moieties cause the retention/degradation of an agent/receptor complex within at least one cell type, but not necessarily in all cells. In like fashion, a rerouting moiety causes retention of an agent/receptor complex in some cells, but not necessarily other agent/receptor complexes in other cells. Different rerouting moieties may also distinguish between receptor species, for example, as in polarized epithelium where the same receptor may independently traffic on the apical, basal, or basolateral sides of the cell. To determine if a particular rerouting moiety is suitable, a rerouting moiety is covalently attached to the targeting moiety, and the resulting receptor modulating agent is compared for receptor modulation on different receptor-bearing cells using binding or functional assays known in the art.

Suitable rerouting moieties of this invention may be categorized into five different functional classes: (1) lysosomotropic moieties; (2) intracellular polymerizing moieties; (3) protein sorting signals or sequences; (4) conditional membrane binding peptides; and (5) bi- or multivalent receptor cross linking moieties. While such rerouting moieties may have different functional mechanisms of action, all promote retention of the agent/receptor complex within the intracellular vesicular system. All of these classes of rerouting moieties will impart the ability to affect the receptor trafficking pathway.

In one aspect of the present invention, a first functional class of rerouting moieties, lysosomotropic moieties, are disclosed. Within the context of the present invention, the term "lysosomotropic moieties" refers to moieties which route the agent/receptor complex to the lysosomes. Numerous suitable lysosomotropic moieties are known, and are reviewed in *Biochem. Pharmacol.* 23:2495–2531, 1974.

A preferred lysosomotropic moiety includes an aminoglycoside antibiotic marked by the characteristic ability to accumulate in lysosomes after intracellular protonation. Intracellular protonation occurs in the increasingly acidic conditions which occur during the transfer from early to late endosomes and, finally, to the lysosome. Strong positive charges prohibit the lysosomotropic moiety from leaving the membrane-enclosed vesicles, thus trapping the agent/receptor complex in the vessel.

Aminoglycoside antibiotics are similar in structure, but are divided into structurally related families of compounds based upon the sugar units. Each of the families of aminoglycoside antibiotics, as well as representative members thereon are set forth in FIGS. 2–5. These families include gentamycin, kanamycin, neomycin and streptomycin. The gentamycin family includes gentamycin $C_1$, gentamycin $C_2$, gentamycin $C_{1a}$, sisomicin and netilmicin; the kanamycin family includes kanamycin A, tobramycin and amikacin; the neomycin family includes neomycin B, paromomycin, ribostamycin and bytirosin B; and the streptomycin family includes streptomycin A and streptomycin B.

In a particularly preferred embodiment of the present invention, the rerouting moiety is gentamycin, which accumulates in lysosomes in concentration as much as 300 fold that of the extracellular concentration (*J. Pharmacol. Exp. Ther.* 255:867–74, 1990; *Ren. Fail.* 14:351–7, 1992).

Suitable aminoglycosides have reactive amine groups capable of being coupled through peptide or other chemical linkers. Thus, a targeting moiety may be readily attached via covalent linkage to these rerouting moieties using any one of several techniques known in the art to form covalent bonds, for example, using thioether, disulfide, ether, ester and peptide bonds. Since many of the aminoglycoside antibiotics have several amines which could be derivatized in a conjugation procedure, a primary amine contained in these compounds can be selectively reacted to favor covalently attachment to the targeting moiety through this amine (see amine indicated with arrow in FIGS. 2–4). With regard to streptomycin, covalent attachment to the targeting moiety may be accomplished by converting the aldehyde moiety indicated in FIG. 5 to an amine, and attaching to the targeting moiety using carbodiimide or other suitable activated carboxylic acid. Amninoglycosides are water soluble and do not readily bind to other proteins, and thus do not impart non-specific binding to a receptor modulating agent.

Figure 3:
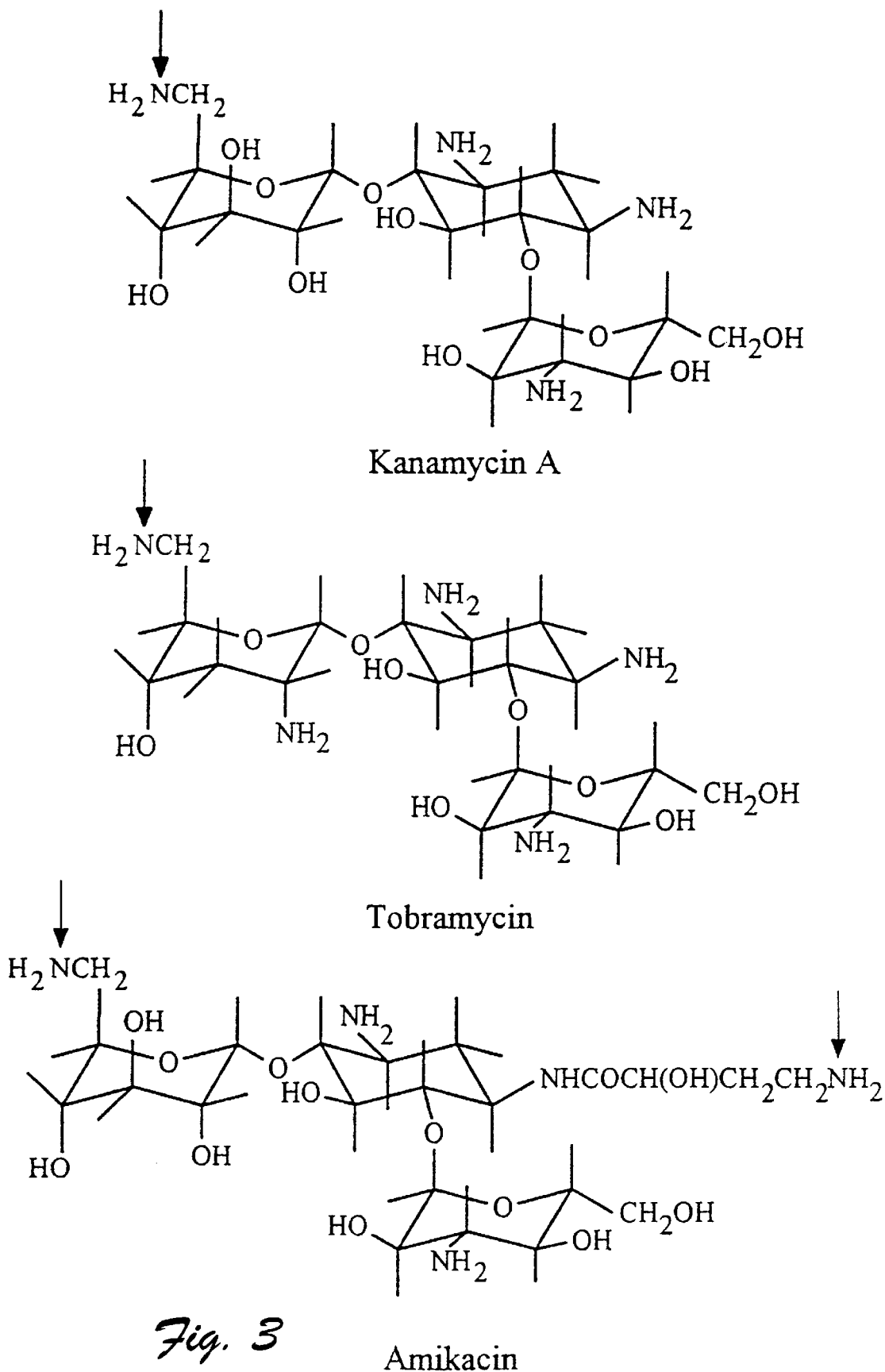
Figure 4:
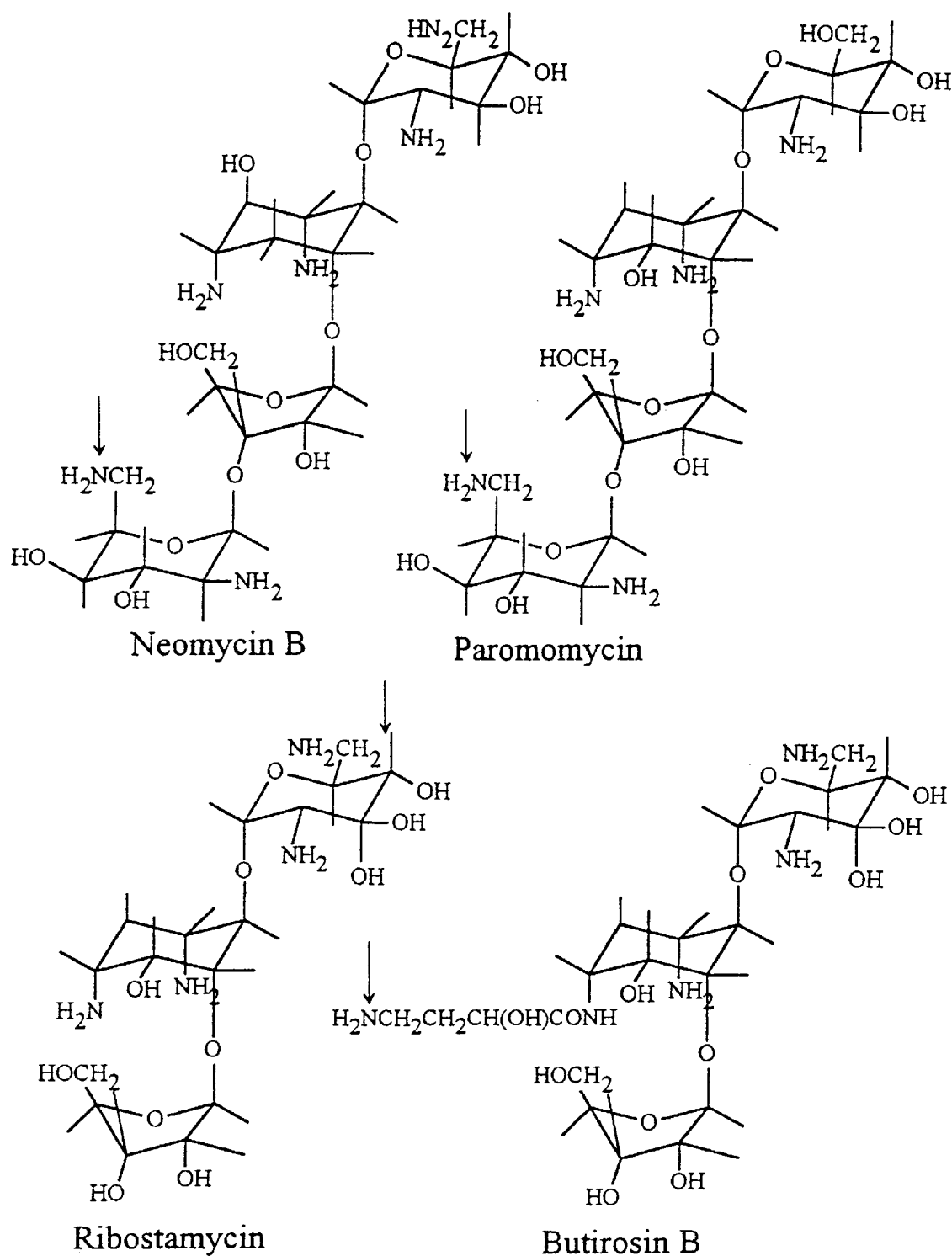

Particularly preferred aminoglycosides include those which allow for preferential derivation of a selected amine. Specifically, preferred aminoglycosides include those compounds to which protective groups can be added to various nitrogen atoms thereof and, subsequently, selectively deprotected to yield a single free amine. The free amine can be further derivatized, for example, by addition of a peptide linker or covalently attached directly to the targeting moiety. These rerouting moieties include ribostamycin (see FIG. 4), kanamycin (see FIG. 3), amikacin, and streptomycin. Ribostamycin is particularly preferred, due to its relative low toxicity and its derivatization chemistry, allowing an acyl migration reaction to be effected on a hydroxyl protected ribostamycin to yield a single amine adduct. Kanamycin may also be used in a selective protection/acylation reaction; Amikacin is commercially available in a form which allows attachment without deprotecting its amines or alcohol groups; and streptomycin can also be readily derivatized by protonating guanidinium groups under physiologic conditions to provide the polycations necessary for cellular or lysosomal retention.

Figure 6:
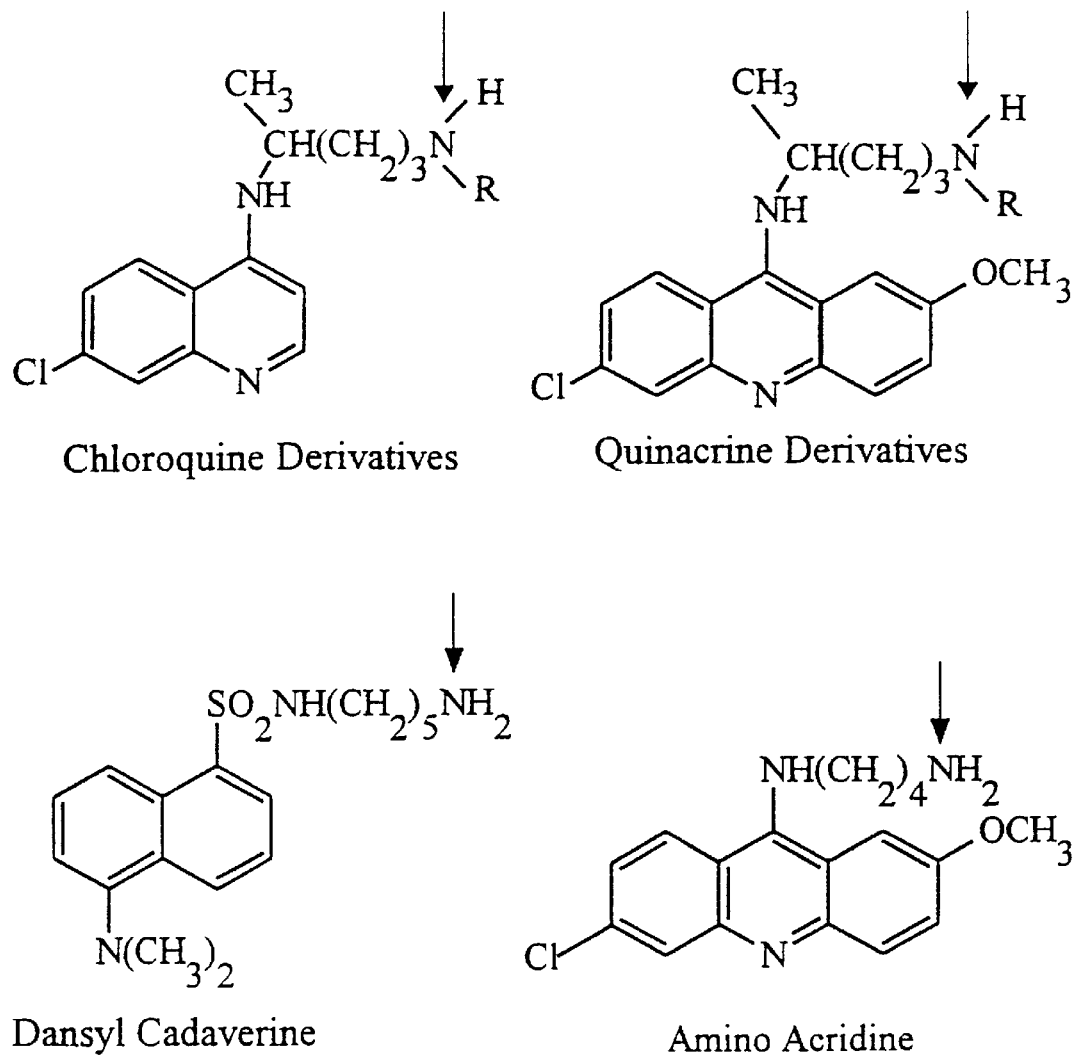
FIG. 6 illustrates formulae representing substituted aminoquinolines (e.g., chloroquine) substituted aminoacridines (e.g., quinacrine), and substituted aminonapthalenes (e.g., dansyl cadaverine), all of which are representative rerouting moieties of the present invention. These rerouting moieties impede the receptor trafficking pathway through protonation and intracellular retention.

In another aspect of the present invention, non-aminoglycoside lysosomotropic compounds which may accumulate after intracellular protonation are also suitable rerouting moieties (see FIG. 6). Suitable non-aminoglycoside compounds exhibiting this characteristic are known in the art, a series of aminoacridine and amino quinoline dyes, typified by cholquinine and quinacrine; a group of amino naphthalenes, typified by dansyl cadaverine; and derivatives thereof. Such dyes are characterized by cellular retention and low toxicity. All of these compounds have characteristic sites for covalent attachment to a targeting moiety via the nitrogen indicated in FIG. 6 and may be attached thereto as described above.

Another aspect of the present invention utilizes a lysosomotropic peptide subject to charge modification under intracellular conditions is employed as a rerouting moiety. Once charge-modified, the rerouting peptide acts to retain an agent/receptor complex in the intracellular vesicular system until membrane flow delivers it to the lysosome for degradation. Preferably, these peptides are capable of being phosphorylated by intracellular protein kinases. When phosphorylated by the intracellular enzymes, such peptides would be highly anionic.

Charge-based retention can be an inherent property of the rerouting peptide or can be imparted by intracellular modification. Intracellular modification may be accomplished by any of several means known in the art, including phosphorylation of certain residues of some receptors (e.g., the EGF receptor) may cause intracellular rerouting (Cancer Treat. Res. 61:139–160, 1992; J. Cell. Biol. 116:321–30, 1992).

The rerouting peptides may be covalently attached to a targeting moiety by any means, including, for example, covalently linking the peptide directly to the targeting moiety, or by use of an appropriate linker moiety, such as G-G-G, which may be derivatized and covalently attached to the targeting moiety.

Preferred rerouting peptides include protein kinase-substrate peptides that incorporate serine. These peptides are particularly preferred for enhancement of receptor rerouting in tumor target cells, which have increased levels of protein kinase activity for serines or tyrosines. Increased levels of kinase activity within tumor cells may be attributed to the presence of oncogene products, such as H-ras, on the cytoplasmic side of tumor cell plasma membranes (C.I.B.A. Found. Symp. 164:208–18, 1992).

Suitable rerouting peptides also include protein kinase substrates and peptides that possess a single positive charge. The latter type of rerouting peptide may form an ion pair with a "glutamate-like" residue of an attached or closely associated residue(s) of the receptor. Particularly preferred rerouting peptides may be derived, using technologies known in the art, from the proteins and the amino acid sequences identified in Table 4.

TABLE 4

REROUTING PEPTIDES

| PEPTIDE SOURCE | AMINO ACID SEQUENCE |
| --- | --- |
| EGF receptor | DVVDADEYLIPQ |
| EGF fragment | CMHIESLDSYTC |
| Phosphorylase kinase | RTKRSGSVYEPLKI |
| Protein kinase C pseudosubstrate | RFARK-GALRQKNV |
| Myelin basic protein | S/T-XAA-K/R (where XAA is an uncharged residue) |
| Kemptide | RGYALG or RGYSLG |
| Glycogen synthetase | PLSRTLSVAA |
| Transferrin receptor | FSLAR |
| III histone | ASGSFKL |
| Casein kinase II substrate | AAAAAASEEE or AAAAAASDDD |
| Insulin receptor auto-phosphorylation substrate | DIYETDYYR |
| calmodulin-dependent protein kinase II | Waxman and Arenowski Biochem. 32(11):2923–30, 1993 |
| Neurogranin | Chen et al., Biochem. 32(4): 1032–9, 1993 |
| MARCKS | Heemskerk et al. Biochem. Biophys. Resp. Commun. 190(1):236–41, 1993 |
| Glycogen synthase | Marais et al., FEBS Letters 277:151–5, 1990 |
| Ribosomal protein S6 | Munro et al., Biochem. Biophys. Acta 1054:225–30, 1990 |
| Co-polymers which serve as substrates for protein kinase A, C, P | Abdel-Ghony et al., Proc. Nat'l. Acad. Sci. 86:1761–5, 1989; Abdel-Ghony et al., Proc. Nat'l. Acad. Sci. 85:1408–11, 1988 |
| Serine-threonine kinases | Abdel-Ghony et al., Proc. Natl. Acad. Sci. 86:1761–5, 1989; Abdel-Ghony et al., Proc. Nat'l. Acad. Sci. 85:1408–11, 1988 |

In another aspect of the present invention, the rerouting moiety is a lysosomotropic amino acid ester which, in high concentration, can cause the lysis of granule containing cells, such as NK cells, cytolytic T cells and monocytes. The concentration must generally be maintained below 100 mM to avoid lysis. Suitable lysosomotropic amino acid esters and their sources are presented in Table 5.

TABLE 5

LYSOSOMOTROPIC AMINO ACID ESTERS

| | |
| --- | --- |
| Leu-O-Me | Res Immunol. 143:893–901, 1992 |
| | Eur. J. Immunol. 23:562–5, 1993 |
| | Intl. Arch. Aller. & Immunol. 100:56–59, 1993 |
| | Cell. Immunol. 139:281–91, 1992 |
| | Ex. Pathol. 42:$_{1,2}$1–7, 1991 |
| Iso-leu-O-Me | Res. Immunol. 143:893–901, 1992 |
| L-Val-O-Me | J. Immunol. 134:786–93, 1985 |
| Phe-O-Me | J. Immunol. 148:3950–7, 1992 |
| | Blood 79:964–71, 1992 |
| Phe-, Ala-, Met-, Trp-, Cys-, Try-, Asp-, & Glu-O-Me | Int. J. Immunopharmacol. 13:401–9, 1991 |

The lysosomotropic amino acid esters identified in Table 5 can be used to retain the agent/receptor complex in lysosomes after intracellular cleavage of the ester. In one embodiment, such amino acid esters may be utilized as the C-terminal portion of a larger peptide containing a linker sequence and/or a phosphorylation substrate sequence, and with suitable residues, such as cysteine, for covalent attachment to a targeting moiety, such as a sequence encoding a peptide or protein ligand for a given cell surface receptor.

In another embodiment of the present invention, a second functional class of rerouting moieties is disclosed. This class includes peptides which undergo polymerization within endosomes or lysosomes, inhibiting their passage through intracellular membranes.

Intracellular polymerizing compounds can be incorporated into a larger peptide containing the targeting moiety and a linker. Suitable peptides include the dipeptide ester referenced in Table 5 (i.e., L-Leucyl-L-Leucine-O-Me). When transported into cells, these dipeptide esters preferentially accumulate in lysosomes and secondary granules of cytotoxic cells. These dipeptides also undergo self-association and polymerization, which results in trapping at low concentrations, and membrane rupture at higher concentrations.

TABLE 6

POLYMERIZING DI-PEPTIDE ESTER:
L-LEUCYL-L-LEUCINE-O-ME

J. Invest. Dermat. 99:805–825, 1992
J. Clin. Invest. 84:1947–56, 1989
Transpl. 53:1334–40, 1992
J. Immunol. 138:51–7, 1987
J. Immunol. 148:3950–7, 1992
J. Immunol. 136:1038–48, 1986
Cryobiology 29:165–74, 1992
Acta. Biochem Biophys. Hung 24:299–311, 1989
Blood 79:964–71, 1992
Blood 78:2131–8, 1991
J. Immunol. 139:2137–42, 1987
T. Exp. Med. 172:183–194, 1990
J. Clin. Invest. 78:1415–20, 1986
PNAS 87:83–7, 1990
J. Immunol. 137:1399–406, 1986
PNAS 82:2468–72, 1985

Suitable intracellular polymerizing compounds also include peptides that can self-associate into alpha-helical structures termed "leucine zippers". In the context of this invention, such structures may be used to form intracellular polymers that are incapable of exiting intracellular vesicles. Such sequences can be selected by observing self association of the compounds in solution, and the formation of polymers capable of binding to DNA. Suitable peptide sequences that can self-associate into alpha helical structures are presented in Table 7.

TABLE 7

LEUCINE ZIPPERS

Boc(t-butoxycarbonyl)-Aib(alpha-aminoisobutyryl)
Glu(OB$_n$1)-(benzoyl ester)-Leu-Aib-Ala-Leu-Aib-Ala-
Boc-Aib-Leu-Aib-Aib-Leu-Leu-Aib-Leu-Aib-O-Me
Proteins 12:324–30, 1992
Lys(Z)(benzyloxy-carbonyl)-Aib-O-Me
PNAS 87:7921–5, 1990
GELEELLKHLKELLKGER
Biochem. 31:1579–84, 1992

In another embodiment of the present invention, a third functional class of rerouting moieties is disclosed. This class includes moieties that can be recognized by intracellular receptors. Such sequences are identified by their ability to stop movement of endogenously synthesized proteins to the cell surface. Suitable peptides include certain peptide sequences (such as sorting or signal sequences) associated with the trafficking of endogenously synthesized proteins (Cur. Opin. Cell. Biol. 3:634–41, 1991). Such peptide sequences, when covalently attached to the C-terminus of an exogenously added targeting moiety, result in the retention of the agent/receptor complexes in the endoplasmic reticulum ("ER"), Golgi apparatus, or lysosomes.

Such peptide sequences are recognized by intracellular receptors, examples of which include both mammalian and bacterial versions of ER receptors described in detail in J. Cell. Biol. 120:325–8, 1993; Embo. J. 11:4187–95, 1992; Nature 348:162–3, 1990. Further exemplary peptide sequences and variants thereof (shown in parentheses) that can be recognized by intracellular receptors are set forth in Table 8, Sections A and B.

Certain signal sequences may be preferred for retention by one type of organism versus another type. For example, REDLK is a preferred sequence recognized by prokaryotic cells and to a lesser degree by eukaryotic cells (see Table 8, section C). Thus, employing this sequence as the rerouting moiety, receptor modulating agents can be constructed to selectively inhibit a receptor-mediated process in bacteria, while having little effect on mammalian cells.

TABLE 8

PEPTIDE SEQUENCES WHICH BIND
INTRACELLULAR RECEPTORS

A. Endoplasmic Reticulum or Golgi Retention Peptides

| | | |
|---|---|---|
| 1. | KDEL (DKEL, RDEL, KNEL, SDEL, KEEL, QDEL, KEDL, KDEL) | J. Biol. Chem. 265:5952–5, 1990<br>Biochem. Biophys. Res. Commun. 172:1384–91, 1990<br>J. Virol. 65:3938–42, 1991<br>Exp. Cell Res. 197:119–24, 1991<br>Growth Factors 5:243–53, 1991<br>J. Biol. Chem. 267(10):7022–6, 1992<br>J. Biol. Chem. 267:10631–7, 1992<br>J. Cell. Biol. 118:795–811, 1992<br>J. Cell. Biol. 119:85–97, 1992<br>Exp. Cell. Res. 203:1–4, 1992<br>P.N.A.S. 90:2695–9, 1993<br>Mol. Biochem. Parasitol 48:47–58, 1991<br>Embo J. 4:2345–55, 1992<br>J. Biol. Chem. 266:14277–82, 1991<br>Mol. Cell Biol. 11:4036–44, 1991 |
| 2. | HDEL (HVEL, HNEL, HTEL, TEHT, DDEL, HIEL) | J. Biol. Chem. 268:7728–32, 1993<br>Mol. Biochem Parasitol 57:193–202, 1993<br>J. Cell SCI 102:261–71, 1992<br>Eur J. Biochem. 206:801–6, 1992<br>J. Biol. Chem. 266:20498–503, 1991 |
| 3. | ADEL | Embo J. 11:1583–91, 1992 |
| 4. | REDLK | J. Biol. Chem. 266:17376–81, 1991 |
| 5. | SEKDEL | Growth Factors 5:243–53, 1991 |
| 6. | KTEL | J. Virol. 66:4951–6, 1992 |

B. LYSOSOMAL RETENTION PEPTIDES

| | | |
|---|---|---|
| 1. | KFERQ | Trends Biochem SCI 15:305–9, 1990 |
| 2. | Tyrosine-containing polypeptides | J. Cell Biol. 111:955–66, 1990 |

C. ORGANISM-SPECIFIC RETENTION PEPTIDES

| | | |
|---|---|---|
| 1. | REDLK | J. Biol. Chem. 266:17376–17381, 1991 |

D. CLATHRIN-BINDING PEPTIDES
(INTERNALIZATION SIGNALS)

| | | |
|---|---|---|
| 1. | LLAV | J. Cell. Biol. 199:249–57, 1992 |
| 2. | YKYSKV | J. Cell. Biol. 199:249–57, 1992<br>Embo. J. 7:3331–6, 1988 |
| 3. | PPGYE | Cell 67:1203–9, 1991<br>Curr. Opin. Cell Biol. 3:1062, 1991 |

A further class of peptide sequences of this invention, termed "internalization signals," function by binding to clathrin, both in the coated pits, as well as those intracellular vesicles which maintain a clathrin coat. Representative examples of such clathrin-binding peptides (CBP) are disclosed in Table 8, section D. The CBP binds clathrin in the coated pits initially located on the cell surface causing retention of the targeting moiety to which it is conjugated.

A further class of moieties capable of recognizing intracellular receptors includes carbohydrates. Suitable carbohydrates include any carbohydrate which is capable of binding to intracellular carbohydrate (CHO) receptors but not cell surface CHO receptors. Such carbohydrates include: mannose-6-phosphate and glucose-6-phosphate. Suitable carbohydrate moieties include those which bind to the insulin-like growth factor II/mannose-6-phosphate (IGF II/M6P) receptor, include analogs of mannose-6-phosphate, as well as other phosphorylated saccharides (*Carbohydrate Res.* 213:3746, 1991; *FEBS Lett.* 262:142–4, 1990).

The affinity of the rerouting moiety can be varied by changes in the chemical nature of the phosphorylated saccharides (*J. Biol. Chem.* 264:7970–5, 1989; *J Biol. Chem.* 264:7962–9, 1989) (monosaccharides bind with the lowest affinity, while di- or tri-saccharides bind with increasingly higher affinity). Clustering of phosphorylated saccharides on protein carriers can dramatically increase affinity to the intracellular receptor.

Synthesis of various oligosaccharides are reviewed in *Sem. Cell. Biol.* 2:319–326, 1991. Although, mannose-6-phosphate receptor expression is primarily intracellular, expression also occurs on cell surfaces. Thus, in the context of the present invention, covalent attachment of a targeting moiety with a carbohydrate which binds the mannose-6-phosphate receptor should be constructed so as to give at least 100-fold difference in binding affinity between the targeting moiety and the rerouting moiety. For example, a vitamin $B_{12}$/transcobalamin II receptor targeting moiety, in this case vitamin $B_{12}$, would have a binding affinity for the carrier protein, transcobalamin II (TcII), of $\geq 10^{-10}$ M and an affinity for the IGF II/M-6-P receptor of $10^{-8}$ M or less. This will maintain the specificity of the vitamin $B_{12}$ binding (via TcII), while allowing transfer of the receptor modulating agent from serum M-6-P soluble receptor to cell surface receptor.

Figure 7:
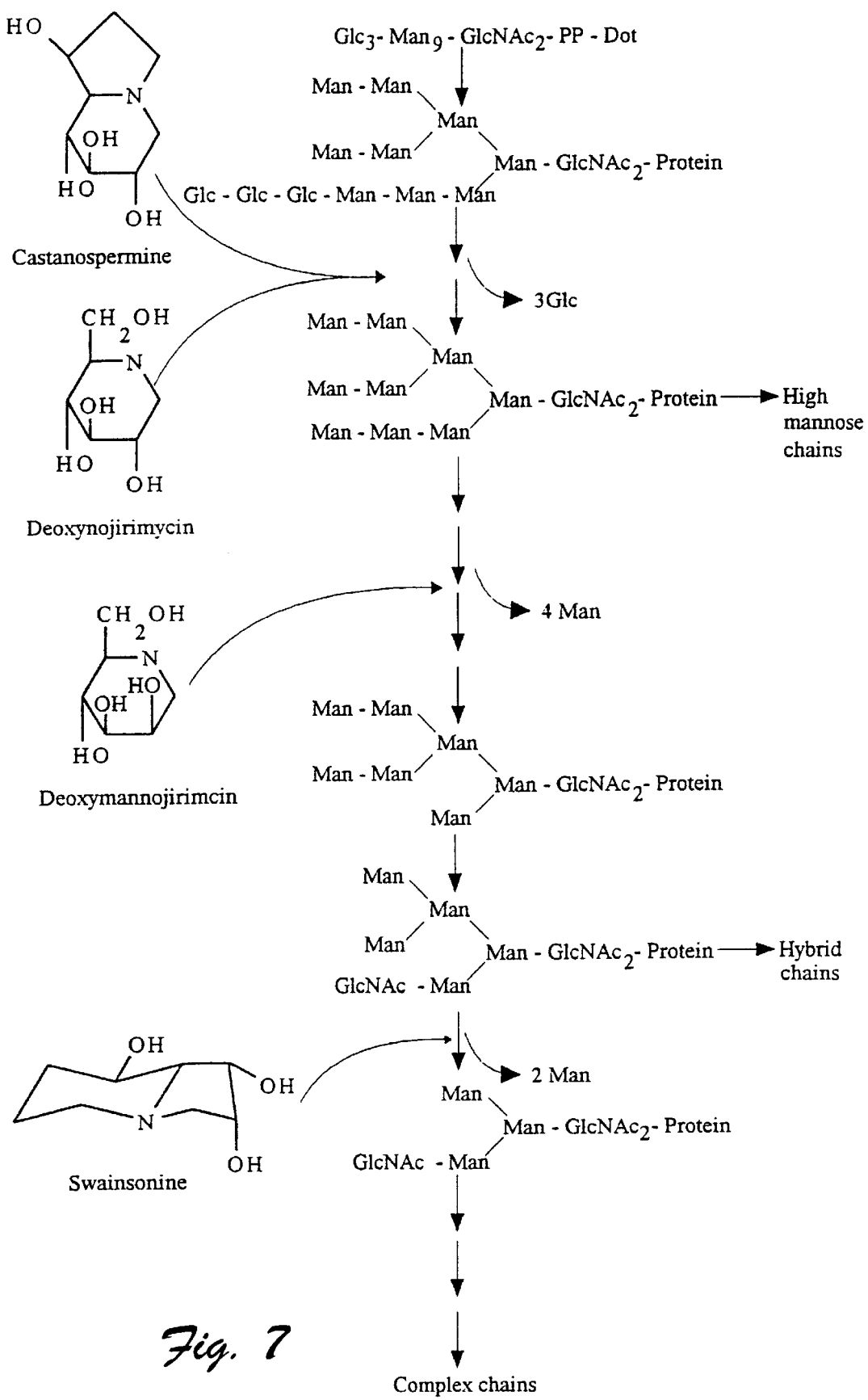
FIG. 7 illustrates formulae representing glycosylation inhibitors, all of which are representative rerouting moieties of the present invention. These sugars may be conjugated to targeting moieties using linkages typical of oligomeric carbohydrate chains. The resulting receptor modulating agent is recognized by internal glycosyl transferases, subject to intracellular retention, and, ultimately, degradation in the lysosomes.

In addition to IGF II/M-6-P receptor moieties, other carbohydrate-based rerouting moieties also promote retention of the modulating agent/receptor complex in the ER or Golgi complex. Such moieties are based on the recognition by various glycosyl transferases of carbohydrate moieties, either as a natural substrate or as an inhibitor. Such moieties are reviewed in *Sem. Cell. Biol.* 2:289–308, 1991. For example, saccharide recognition moieties include penultimate sugars, such as glucose and N-acetyl glucosamine (which are natural substrates). More preferred, however, are glycosylation inhibitors which are recognized by glycosyl transferases, but cannot serve to append further carbohydrate residues on growing chains (*Sem. Cell. Biol.* 2:309–318, 1991) (see FIG. 7).

In yet another embodiment of the present invention, a fourth functional class of rerouting moieties is disclosed. This class is generally comprised of rerouting moieties which anchor the receptor to the cell membrane. By way of example, this class includes membrane-binding peptides that exhibit conditional pH-dependent membrane binding. Such peptides exhibit a-helical character in acid but not neutral pH solutions. When a conditional membrane-binding peptide assumes a helical conformation at an acidic pH, it acquires the property of amphiphilicity, (e.g., it has both hydrophobic and hydrophilic interfaces). More specifically, within a pH range of approximately 5.0–5.5, such a peptide forms an alpha-helical, amphiphilic structure that facilitates insertion of the peptide into a target membrane. An alpha helix-induced acidic pH environment may be found, for example, in the low pH environment present within cellular endosomes or lysosomes. In aqueous solution at physiological pH, a conditional, membrane-binding peptide is unfolded (due to strong charge repulsion among charged amino acid side chains) and is unable to interact with membranes.

Suitable conditional membrane-binding peptide sequences include the charged amino acids glutamate, aspartate, and histidine. A preferred conditional membrane-binding peptide includes those with a high percentage of helix-forming residues, such as glutamate, methionine, alanine, and leucine. Further, conditional membrane-binding peptide sequences include ionizable residues having pKas within the range of pH 5–7, so that a sufficiently uncharged membrane-binding domain will be present within the peptide at pH 5 to allow insertion into the target cell membrane. Conditional membrane-binding peptides can be incorporated through covalent bonds to a chemical or peptide targeting moiety or synthesized as an entire peptide sequence including a linker and peptide targeting moiety.

A particularly preferred conditional membrane-binding peptide is aa1-aa2-aa3-EAALA(EALA)$_4$-EALEALAA-amide, which represents a modification of a published peptide sequence (*Biochemistry* 26:2964, 1987). Within this peptide sequence, the first amino acid residue (aa1) is preferably a unique residue such as cysteine or lysine, that facilitates chemical conjugation of the conditional membrane-binding peptide to a targeting protein. The peptide can also be incorporated into a fusion protein with a protein or peptide targeting moiety (see Example 7). Amino acid residues 2–3 (i.e., aa2–aa3) may be selected to modulate the affinity of the translocating peptide for different membranes. For instance, if both residues 2 and 3 are lysine or arginine, the peptide will have the capacity to bind to membranes or patches of lipids having a negative surface charge. If residues 2–3 are neutral amino acids, the peptide will insert into neutral membranes.

Yet another preferred conditional membrane-binding peptide can be derived from sequences of apo-lipoprotein A-1 and B; peptide toxins such as melittin, bombolittin, delta hemolysin and the pardaxins; antibiotic peptides, such as alamethicin; peptide hormones, such as calcitonin, corticotrophin releasing factor, beta endorphin, glucagon, parathyroid hormone, and pancreatic polypeptide. Such peptides normally bind membranes at physiologic pH but through attachment of substituents the peptides can be enhanced in their ability to form alpha-helices at acidic pH and reduced in their membrane-binding at physiologic pH. An example of such a modified peptide having pH-dependent membrane binding at acidic pH is fully succinylated melittin. In this example, a peptide (melittin) that normally binds to membranes at physiological pH is converted to a pH-dependent peptide through succinylation of lysines. Upon succinylation, the peptide displays an anphipathic character only at acidic pHs.

Insertion of a conditional membrane-binding peptide into a target cell membrane is enhanced through stabilization of the amphiphilic alpha helix. Helix stabilization may be achieved: (1) by adding repeating "EALA" units to form a longer peptide; (2) by placing an amide at the C-terminus of the peptide, in order to counteract the helical dipole; (3) by polymerizing the peptide; (4) by substituting a natural helix-former for one or more of the stacked glutamates; or (5) by attaching the peptide to a targeting moiety through use of a longer linker, in order to provide sufficient distance between the membrane binding peptide and the targeting moiety for the peptide to contact and interact with the target cell intracellular membranes.

In yet another embodiment of the present invention, a fifth functional class of rerouting moieties is disclosed. In this context, the rerouting moiety merely functions as a modulating agent in that the moiety disables the receptors by crosslinking the same. This class includes bi- or multi-valent receptor crosslinking moieties formed from monovalent binding targeting moieties. Cross-linking of receptors in some receptor systems is sufficient to cause a rerouting of cell surface receptors to lysosomes for degradation, rather than their normal pathway of receptor recycling. The synthesis of a bivalent receptor modulating agent is exemplified in greater detail in the examples below.

A preferred cross-linking receptor modulating agent is a vitamin $B_{12}$ dimer. In this embodiment, each vitamin $B_{12}$ molecule acts as a targeting agent and a rerouting agent; cross-linking the $B_{12}$ dimer will cross-link the vitamin $B_{12}$ receptors, thus impeding the receptor trafficking pathway. A preferred vitamin $B_{12}$ dimer is generally comprised of two vitamin $B_{12}$ molecules, such as cyanocobalamin, coupled by one or more linkers through coupling sites independently selected from a–g, h (ribose), and i (benzimidazole). Preferably, cross-linking occurs between b- or e-coupling sites on both molecules. The dimer must be capable of forming a $B_{12}$/TcII complex. As noted above, this characteristic may be assayed using any one of several techniques known in the art, including competitive binding assays.

A vitamin $B_{12}$ may be coupled to a second vitamin $B_{12}$ molecule in the same manner as described in detail for conjugation of rerouting moieties to vitamin $B_{12}$ targeting moieties. As noted above, dimers may be synthesized using one or more linkers of various lengths, solubilities, and any combination of homobifunctional, heterobifunctional, homotrifunctional, or heterotrifunctional linkers. As noted above, the use of a trifunctional linker allows for coupling with any number of additional moieties.

In selecting a linker for dimer synthesis, it should be noted that the total number of atoms comprising the linker between the vitamin $B_{12}$ molecules should generally be greater than 10 atoms, typically be in the range of 30 to 55 atoms and, preferably be about 45. As noted above, one of ordinary skill in the art will appreciate that although the number of atoms is calculated relative to a linear chain of atoms, linear chain, branched chain, and cyclical chain linkers or combinations thereof would be suitable. Hence, the structure of the atom chain in a linker would include, by way of example, alkyl, heteroalky, alkylaryl, and heteroalkyl aryl.

By way of example, a dimer may be synthesized by combining two different vitamin $B_{12}$ linker adducts in the presence of a coupling agent. The linkers couple and dimers may then be separated and purified using the same methods outlined above. The synthesis of a representative vitamin $B_{12}$ linker adduct is described in Example 23.

Alternatively, activated vitamin $B_{12}$ may simply be combined with a homobifunctional or homotrifunctional linker (Tables 1 and 3). Preferably, in this embodiment, the ratio of vitamin $B_{12}$ to linker should be in the range of 2:1. Preferably, a 1:1 ratio is used in preparation of mixed dimers (e.g., b- and e-acid derivatives) or mixed ligands (e.g., $B_{12}$ and hormone). Dimers may be separated and purified as noted above.

In still another alternative, vitamin $B_{12}$ linker adducts, synthesized as described, above may be coupled by a third linker. The third linker, a "cross-linker," serves to bridge the linkers on the vitamin $B_{12}$ linker adducts. Suitable cross-linkers include those noted in Tables 1, 2, and 3. The synthesis of representative vitamin $B_{12}$ dimers having bridging cross-linkers are described in Example 25.

In still another alternative, vitamin $B_{12}$ dimers may also be prepared utilizing a cross-linker which functions through high affinity specific binding interactions. The high specific binding affinity of biotin for avidin ($Ka=10^{15}$) provides such a high affinity binding. Accordingly, the receptor modulating agents of the present invention include vitamin $B_{12}$ dimers and vitamin $B_{12}$ tetramers bound through the avidin-biotin interaction. An vitamin $B_{12}$/avidin conjugate may be readily prepared by the addition of a suitable vitamin $B_{12}$/biotin conjugate to avidin (or streptavidin).

Avidin and streptavidin are tetrameric proteins having four biotin binding sites situated in pairs on either side of the protein. Thus, a range of vitamin $B_{12}$/avidin conjugates may be prepared in which the number of vitamin $B_{12}$ molecules or derivatives per avidin may be varied from one to four. In one preferred embodiment, the vitamin $B_{12}$/avidin conjugate has four vitamin $B_{12}$ molecules or derivatives per conjugate. As noted above, these tetrameric vitamin $B_{12}$ conjugates may be prepared by binding a suitable vitamin $B_{12}$/biotin conjugate (i.e., a vitamin $B_{12}$/biotin conjugate composed of one biotin and one vitamin $B_{12}$ molecule or derivative) to avidin under conditions in which all four avidin binding sites are utilized. Suitable vitamin $B_{12}$/biotin conjugates include those conjugates in which the biotin is covalently linked to a vitamin $B_{12}$ coupling site with a linker of length sufficient to permit binding of the vitamin $B_{12}$ conjugate to avidin. Subject to the considerations noted above, suitable linkers are in the range of about 12 to 50 atoms in length, and preferrably about 25 to 45.

In another preferred embodiment, the vitamin $B_{12}$/avidin conjugate is a vitamin $B_{12}$ dimer having two vitamin $B_{12}$ molecules or derivatives per conjugate. These vitamin $B_{12}$/avidin conjugates may be prepared using a suitable vitamin $B_{12}$/biotin conjugate having two biotins linked to a single vitamin $B_{12}$ molecule or derivative. In this embodiment, suitable vitamin $B_{12}$/biotin conjugates include conjugates in which the biotins of the conjugate may both bind to each of one pair of avidin binding sites. The length of the linker between the vitamin $B_{12}$ and the biotins in the vitamin $B_{12}$/biotin conjugate may be of sufficient length to permit binding to a pair of avidin binding sites, but not so lengthy as to be capable of binding to one binding site on one side of the avidin, and another binding site on the opposite side of the avidin. In a preferred embodiment, the vitamin $B_{12}$/avidin conjugate prepared from avidin and two vitamin $B_{12}$/biotin conjugates (having two biotins per vitamin $B_{12}$) has each pair of biotin binding sites occupied by a vitamin $B_{12}$/biotin conjugate.

Polymerization of peptides for use in the present invention may be accomplished by placing a cysteine residue at each end of a peptide, followed by oxidation using dissolved oxygen or other mild oxidizing agent, such as oxidized glutathione. The average length of a polymerized peptide may be controlled by varying the polymerization reaction conditions.

The amino acid sequence of any of the peptides of this invention may be selected to include all L-amino acids or all D-amino acids having a side chain $pK_a$ from 5.0 to 9.0. D-amino acids may be advantageously used to form non-proteolyzable peptides, since the D-amino acids are not metabolized within the cell. Further, the peptides of the present invention may include a combination of L- and D-amino acids, wherein D-amino acids are substituted for L-amino acids on either side of a proteolytic cleavage site. Yet another preferred noncleavable peptide incorporates peptide bond analogs that are not susceptible to proteolytic cleavage by cellular enzymes.

As discussed above, the receptor modulating agents of this invention comprise a targeting moiety coupled to the rerouting moiety. The rerouting moieties identified above may be covalently attached to the targeting moiety by any one of several techniques known in the art, including (a) by chemical modifications such as a disulfide formation, thio-ether formation, amide formation or a reduced or non-reduced Schiff's base, (b) by direct peptide bond formation as in a fusion protein, or (c) by use of a chemical and peptide linker. Suitable peptide linkers in this regard correspond to two or more amino acid residues that allow the rerouting peptide to assume its active conformation independent of its interaction with the targeting moiety, and which allows sufficient distance for rerouting moiety access to, for example, intracellular membranes from the peptide attachment site on the targeting moiety.

In one embodiment, a rerouting moiety may be conjugated to a vitamin $B_{12}$ targeting moiety by any one of several means, including, by way of example, coupling a rerouting moiety to a reactive group on a vitamin $B_{12}$ linker adduct; coupling a vitamin $B_{12}$ to a reactive group on a rerouting moiety linker adduct or an appropriate side chain thereof; coupling a vitamin $B_{12}$ linker adduct to a rerouting moiety linker adduct or an appropriate side chain thereof; coupling a rerouting moiety/biotin binding protein conjugate to a vitamin $B_{12}$/biotin conjugate; or coupling a rerouting moiety biotin conjugate to a vitamin $B_{12}$/biotin binding protein conjugate.

Coupling of a rerouting moiety to a vitamin $B_{12}$ linker adduct, or a vitamin $B_{12}$ to a rerouting moiety linker adduct, may be accomplished using the same techniques noted above for coupling a vitamin $B_{12}$ molecule with a linker. The only critical consideration of this aspect of the invention is that the total linker length must be sufficient to avoid steric hindrance. Preferably, the total linker length is at least 6 atoms.

Coupling of a rerouting moiety/biotin binding protein conjugate to a vitamin $B_{12}$/biotin conjugate may be accomplished using any one of several means described in detail in *Avidin-Biotin Chemistry: A Handbook*, ed. D. Savage, Pierce Chemical Co., 1992. Briefly, a biotin binding protein conjugate is prepared using a rerouting moiety or, as in a second embodiment, a vitamin $B_{12}$ molecule. Suitable biotin binding proteins include avidin or streptavidin. In some circumstances, a linker may be utilized to distance the molecules. For example, when coupling a vitamin $B_{12}$ to an avidin, a linker of at least 6 atoms is preferred.

A biotin conjugate is prepared using a vitamin $B_{12}$ molecule or, as in a second embodiment, a rerouting moiety. By way of example, a vitamin $B_{12}$ molecule is combined with an NHS ester of biotin. Preferably, the vitamin $B_{12}$ molecule is a vitamin $B_{12}$ linker adduct as described above. Even more preferably, the vitamin $B_{12}$ molecule is a vitamin $B_{12}$ linker adduct characterized by a 14 atom linear linker coupled to the b- or e-coupling site. The synthesis of a representative vitamin $B_{12}$/biotin conjugate is described in Example 24.

Once formulated, coupling between the biotin conjugates and biotin binding protein conjugates is easily accomplished by combining the complementing conjugates, i.e., a vitamin $B_{12}$/biotin conjugate with a rerouting moiety/avidin conjugate.

In another aspect of the present invention, a $B_{12}$/biotin conjugate is utilized to couple a vitamin $B_{12}$ to any number of compounds through biotin binding protein conjugates. Using a vitamin $B_{12}$/biotin conjugate, any compound which is capable of coupling a biotin binding protein may be coupled to a vitamin $B_{12}$ and thereby internalized into cells expressing the vitamin $B_{12}$ receptor. Such compounds include, in addition to the rerouting moieties described in detail below, hormones, enzymes, antibodies or fragments thereof markers, or therapeutics. Coupling any of these compounds to a biotin binding protein, such as avidin or streptavidin, may be accomplished using techniques described in detail in *Avidin-Biotin Chemistry: A Handbook*, ed. D. Savage, Pierce Chemical Co., 1992.

In one aspect of this embodiment, a vitamin $B_{12}$/biotin conjugate is coupled to a therapeutic/avidin conjugate directed at neoplastic disorders. Neoplastic disorder therapeutics which may be coupled to a vitamin $B_{12}$/biotin conjugate through avidin include doxorubicin, daunorubicin, etoposide, teniposide, vinblastine, vincristin, cyclophophamide, cisplatin and nucleoside antimetabolites such as arabinosylcytosine, arabinosyladenine and fludarabine.

In another aspect of this embodiment, a vitamin $B_{12}$/biotin conjugate is coupled to a marker conjugated with a biotin binding protein. Suitable markers include, by way of example, fluorescent molecules or radiolabeled molecules. This combination may be utilized as a detection system incorporated into a screening device to identify patients with low receptor bearing cells or in the evaluation of receptor up-regulation, for example, following treatment of patients for any one of a wide variety of receptor modulation disorders.

In another aspect of this embodiment, a vitamin $B_{12}$/biotin conjugate is coupled to a radioisotope conjugated to a biotin binding protein. Suitable radioisotopes include, any high energy emitting radioisotopes capable of conjugating a biotin binding protein. This combination may be utilized as a targeted radiodiagnostic or radiotherapeutic.

In yet another aspect of this embodiment, a vitamin $B_{12}$/biotin conjugate is used to immobilize vitamin $B_{12}$ to a solid matrix or avidin-coated substrate. By way of example, this would enable one to isolate TcII, TcII receptors, and evaluate coupling sites on the Vitamin $B_{12}$.

The receptor modulating agents of this invention regulate receptor-dependent biological responses through alterations in the receptor trafficking pathway. As illustrated in FIG. 1, with specific reference to the receptor for vitamin $B_{12}$, cell surface receptors are often associated with clathrin-coated pits. When bound by the receptor modulating agent of the present invention, the coated pits invaginate to form vesicles. The vesicles are then directed by the rerouting agent to lysosomes for receptor degradation or delivered to endosomes where the rerouting agent securely binds or delays the agent/receptor complex. Thus, the receptor modulating agents can incapacitate the receptors normally undergoing recycling.

Newly synthesized receptors will eventually replace the internalized receptor on the cell surface. However, this process is far more time consuming than recycling-many cells require hours or days to achieve maximal receptor re-expression. Continued exposure of the cell to the receptor modulating agents will exhaust the intracellular receptor pools. Thus, by modulating a plasma membrane receptor, re-expression of the receptor can be substantially delayed, thereby regulating a biological response associated with that receptor for a prolonged period of time.

Biological activity of receptor modulating agents of the present invention may be ascertained in vitro by any one of several means known in the art including, competition binding assays or cell proliferation studies. These techniques are described in detail in *Laboratory Techniques in Biochemistry and Molecular Biology: An Introduction to Radioimmunoassay and Related Techniques*, 3rd Edition, ed. Burdon and van Knippenberg, Elsevier, 1987. By way of example, a receptor modulating agent may be cultured with a suitable cell line, such as K562 cells (ATCC CCL 243), under conditions representing in vivo conditions. Such conditions would include the provision of a human source of TcII (such as human serum), vitamin $B_{12}$, and, preferably by careful removal by chromatography, of all TcII from other medium supplements such that proliferation is solely dependent on a known amount of exogenous TcII. Cell cultures deprived of vitamin $B_{12}$ gradually lose their proliferative capacity, eventually resulting in cell death Biological activity may be evaluated in vivo using techniques described in detail in Shieh et al., *J. Immunol.* 152(2):859–866, 1994 in which human tumor cell lines are injected into nude mice, followed by therapy with receptor modulating agents. Next, tumor cells are removed, single cell suspensions prepared and TcII cell surface receptor density may be evaluated by flow cytometry and biotinylated vitamin $B_{12}$ and avidin FITC.

The receptor modulating agent of the present invention may be administered in a therapeutically effective amount to treat a variety of disorders characterized in which control of the disease process or symptoms can be achieved by modulation of one or more receptor systems and the associated biological responses. Such disorders include neoplastic disorders, autoimmune diseases, rheumatic arthritis, cardiovascular disease, and neurodegenerative diseases.

Common to many non-neoplastic disease processes is a stage in which the disease process itself, or its symptoms, can be halted or ameliorated by the use of an anti-proliferative agent such as vitamin $B_{12}$/TcII receptor modulating agents. These commonly recognized stages include a sensitization or elicitation phase in which immune cells responsible for the disease become turned on by antigen specific or non-specific means, followed by a proliferative phase in which the immune cells expand in number, and finally a symptomatic phase in which the expanded immune cells create tissue damage directly or indirectly. Neoplastic disorders include, by way of example, leukemia, sarcoma, myeloma, carcinoma, neuroma, melanoma, cancers of the breast, lung, liver, brain, colon, cervix, prostrate, Hodgkin's disease, and non-Hodgkin's lymphoma Because of this, anti-proliferative chemotherapeutic drugs are commonly utilized in the treatment of many diseases other than cancer, but are limited in use to life threatening situations due to their associated toxicity. Anti-proliferative agents, such as the ones of the present invention (with little of the direct toxicity of chemotherapeutic drugs), may be used more widely. More specifically, the vitamin $B_{12}$ receptor modulating agents of the present invention are not destructive to plasma membrane processes (e.g., ion transport). In addition, the anti-proliferative activity is reversible by administration of vitamin $B_{12}$. Furthermore, the agents of this invention may not be mutagenic, teratogenic, or carcinogenic since they act at the level of the plasma membrane, and not at the level of the nucleus, and DNA by intercalation or cross-linking (as many chemotherapeutic drugs act).

An understanding of the pharmaceutical applications for $B_{12}$/TcII receptor modulating agents requires a knowledge of the cell types targeted by such therapy. To this end, various pharmaceutical applications are disclosed in Table 9 below.

TABLE 9

TARGET CELLS FOR VITAMIN $B_{12}$ RECEPTOR MODULATING AGENTS

| TARGET CELL | OTHER PROLIFERATION ASSOCIATED MARKERS | POTENTIAL PHARMACEUTICAL APPLICATIONS |
|---|---|---|
| Activated T-Cell | IL-2 receptor Transferrin Receptor Insulin Receptor Class II Histo-compatibility Antigens | Graft versus Host Disease Organ Transplants Auto-Immune Diseases Asthma Crohn's Disease |
| Tumor Cells | Tumor Assoc. Ags. Ki67 Transferrin Receptor | Tumor Therapy (alone and in combination with chemotherapeutic drugs) |
| Bone Marrow Stem Cells | CD-34 Transferrin Receptor Class II Histo-compatibility Antigens IL-1, IL-3 Receptors | Allogeneic Bone Marrow Transplants Reduction in Toxicity of Chemotherapy |
| Proliferating Fibroblasts | Thy 1.1 Transferrin Receptor Insulin & Insulin-like Growth-Factor Receptors Fibroblast Growth-Factor Receptor | Inhibition of adhesions, Scarring Scleroderma |
| Proliferating Epithelium or Epidermal (Keratinocytes) | EGF Receptor Proto-Oncogenes | Psoriasis |

Proliferating and activated T-cells can cause a wide variety of diseases ranging from the chronic inflammation of Crohn's disease to more acute organ graft rejection. In all of these diseases, the T-cell may serve a central pathogenic role or a more accessory role. Anti-proliferative chemotherapeutic drugs serve to reduce symptomotology and in some cases lead to long-term remission. Similarly, proliferating fibroblasts and epithelial cells may give rise to diseases characterized by cell overgrowth. Vitamin $B_{12}$ receptor modulating agents may be used to replace or used in combination with existing chemotherapeutic regimens in these diseases. An important aspect of the use of anti-proliferative vitamin $B_{12}$ receptor modulating agents in these diseases is not to apply it so aggressively or with improper timing such that normal healing (adhesions, scarring) or cell renewal (psoriasis) processes are also inhibited. As such, low doses of receptor modulating agents may be used during healing and higher doses once healing is completed. Alternatively, receptor modulating agents may not be administered at all until after healing is completed.

As previously mentioned, $B_{12}$/TcII receptor modulating agents can be used to deprive neoplastic cells of vitamin $B_{12}$. It has already been shown that sufficient deprivation leads to the death of rapidly proliferating lymphoid neoplasms such as leukemia and lymphoma. Moreover, short term treatment to reduce cellular availability of this nutrient, combined with existing chemotherapeutic agents, markedly improves therapeutic efficacy.

For solid tumors, vitamin $B_{12}$ depletion may induce cytostasis and differentiation as well as cell death. Thus, $B_{12}$/TcII receptor modulating agents may be used to induce differentiation in hormonally responsive solid tumors. An increase in the number of cells expressing a differentiated phenotype should translate into an increase in expression of hormone receptors. The hormone receptor status of tumors, such as breast and prostrate cancer, are directly correlated with their response to hormonal therapy. Accordingly, $B_{12}$/TcII receptor modulating agents can be used to increase the number of receptor positive tumor cells or increase receptor density in order to enhance efficacy of subsequent hormonal therapy.

Vitamin $B_{12}$ receptor modulating agents may affect both replicating neoplastic and normal cells. However, bone marrow progenitors demonstrate differential sensitivity or response. Thus, $B_{12}$ receptor modulating agents can be used to modulate sensitivity of bone marrow progenitors so as to enhance their resistance to the toxic effects of chemotherapeutic agents. Such chemotherapeutic drugs act primarily on replicating cells, with non-replicating cells being much less sensitive. Decreasing the sensitivity of progenitors to toxic drugs would increase the bone marrow reserves and enhance subsequent response to colony stimulating factors, and enable higher doses of chemotherapy or reduce the interval to reconstitution. It should also be recognized that such positive effects on bone marrow progenitors, as a natural consequence of $B_{12}$ receptor therapy for cancer, is an additional mechanism by which the therapeutic index of chemotherapeutic drugs other than 5-FU and methotrexate can be improved.

In a variety of autoimmune diseases, graft versus host disease, ectopic allergy, and organ transplantation, an initial 'induction' phase, in which the patient becomes sensitized to self or allo-antigens, is followed by a "proliferative" phase in which forbidden or unregulated clones of B- or T-cells are expanded. It has long been known that treatment with anti-proliferative, chemotherapeutic drugs following induction can inhibit expansion of forbidden clones, inhibit progression of disease, and restore a stable state of tolerance.

Inflammation is an application for which antibodies are already being utilized in clinical trials. The primary emphasis has been on inhibiting the early manifestations of inflammation by inhibiting recruitment or binding of inflammatory cells to vascular endothelium of injured tissue. It also well recognized that proliferation of cells at the site of inflammation contributes to the pathology and tissue destruction of both acute as well as chronic inflammation. To this end, anti-proliferative, chemotherapeutic drugs have been widely used to inhibit sequelae of inflammation.

Methotrexate is one such drug commonly used to treat symptoms associated with rheumatoid arthritis. The drug acts to reduce both localized (e.g., synovium) and generalized inflammation associated with disease progression. Methotrexate acts synergistically with vitamin $B_{12}$ depletion in therapy of leukemia. $B_{12}$ receptor modulating agents can therefore be combined with methotrexate to enhance efficacy in rheumatoid arthritis. Other methotrexate applications include treating destructive inflammation associated with chronic heart disease and colitis.

Surgery, radiation or chemotherapy to the abdomen is often complicated by the development of tissue adhesions. These represent a considerable clinical problem because they lead to bowel blockage and require surgical intervention. Peritoneal adhesions arise as a result of proliferation of the cells of the peritoneal membrane lining the abdomen. A non-toxic means of interfering with such proliferation could lead to restoration of these normal cells to homeostatic control mechanisms and thereby inhibition of adhesion formation. A similar process of benign proliferation and subsequent scarring is a complication of retinal surgery. Direct instillation of a small molecule analog of an antibody receptor antagonist could prevent such disabling complications.

The term "treatment" as used within the context of the present invention, refers to reducing or alleviating symptoms in a subject, preventing symptoms from worsening or progressing, inhibition or elimination of the causative agent, or prevention of the infection or disorder in a subject who is free therefrom. Thus, for example, treatment of infection includes destruction of the infecting agent, inhibition of or interference with its growth or maturation, neutralization of its pathological effects and the like. A disorder is "treated" by partially or wholly remedying the deficiency which causes the deficiency or which makes it more severe.

The receptor modulating agents of the present invention are administered in a therapeutically effective dose. A therapeutically effective dose may be determined by in vitro experiment followed by in vivo studies.

Pharmaceutical compositions containing the receptor modulating agents in an admixture with a pharmaceutical carrier or diluent can be prepared according to conventional pharmaceutical compounding techniques. The carrier may take a wide variety of forms depending on the form of preparation desired for administration (e.g., intravenous, oral topical, aerosol, suppository, parenteral or spinal injection). Preferably, administration is via stereotactical injection.

The following examples are offered by way of illustration, not limitation.

EXAMPLES

In summary, the examples which follow disclose the synthesis of several receptor modulating agents of this invention utilizing different functional classes of rerouting moieties. More specifically, a series of examples are presented which employ vitamin $B_{12}$ as a targeting moiety in a receptor modulating agent.

All chemicals purchased from commercial sources were analytical grade or better and were used without further purification unless noted. Isophthaloyl dichloride was purchased from Lancaster Synthesis Inc. (Windham, N.H.). All other reagents were obtained from Aldrich Chemical Co. (Milwaukee, Wis.). Solvents for HPLC analysis were obtained as HPLC grade and were filtered (0.2 $\mu$m) prior to use. Ion exchange chromatography was conducted with 200–400 mesh strongly basic anion 2% cross-linking Dowex-1-chloride (Aldrich Chemical Co). Amberlite XAD-2 nonionic polymeric adsorbent and octadecyl functionalized silica gel for column chromatography were obtained from Aldrich Chemical Co.

$^1$H NMR were obtained on Bruker AC-500 (500 MHz) instrument. The chemical shifts are expressed as ppm ($\delta$) using tetramethylsilane as internal reference. IR data were obtained on a Perkin-Elmer 1420 infrared spectrophotometer. UV data were obtained on a Perkin-Elmer Lambda 2 U/V is spectrophotometer. Mass spectral data were obtained on a VG 7070H mass spectrometer using fast atom bombardment (FAB).

HPLC separations of compounds were obtained on Hewlett-Packard quaternary 1050 gradient pumping system with a UV detector. Analysis of the HPLC data were obtained on a Hewlett-Packard HPLC Chemstation software.

HPLC for Monomers: HPLC separations were conducted at a flow rate of 1 mL/min. on a 5 mm, 4.6 250 mm $NH_2$ column (RAININ microsorb-MV amino column) eluting with 58 mM pyridine acetate, pH 4.4 in $H_2O$: THF (96:4) solution. Retention times were: 1=4.3 min; 2=6.5 min; 3=8.0 min; 4=8.8 min; 5=109 min; 6=2.3 min; 7=2.3 min; 8=3.0 min; 9=2.9 min; 10=2.9 min; 13=3.4 min. Reverse-phase HPLC chromatography was carried out using a Hewlett-Packard Lichrospher 100 RP-18 (5 mm, $_{12}$5×4 mm) C-18 column using a gradient solvent system at a flow rate of 1 mL/min. Solvent A in the gradient was methanol. Solvent B was $H_2O$. Starting from an 40% A, the gradient was increased to 100% A over 10 min. The gradient was then brought back to 40% A over a 5 min period. Retention times under these conditions for biotin conjugates were: 17=7.1 min; 18=7.2 min; 19=6.9 min; 20=6.4 min.

Preparative LC was conducted to separate the mixture of monocarboxylic acids using RAININ Rabbit-plus peristaltic pumping system with a DYNAMAX (model UV-1) UV-visible absorbance detector at a flow rate of 0.15 mL/min. D column (Alltech, 150 psi), (1000 mm×25 mm) packed with aminopropyl silica (40–63 mm) was used.

HPLC for Dimers: For dimers 36, 37, and 38 solvent A in the gradient was methanol. Solvent B was $H_2O$. The gradient was held at the starting mixture of 70% A for 2 min, then the percentage of A was linearly increased to 100% over the next 10 min. The gradient was held at 100% A for 20 min. Retention times under these conditions for dimers were: 36=8.7 min; 37=9.0 min; 38=8.9 min. For dimers 58–60 and 64–46 Solvent A in the gradient was methanol. Solvent B was aqueous 1% acetic acid. The gradient was begun at 40% A and was held at that composition for 2 min, then the percentage of A was linearly increased to 100% over the next 10 min. Retention times for the compounds examined under these conditions were: 58=14.0 min; 59=14.1 min; 60=13.9 min; 64=8.7 min; 65=8.6 min; 66=9.0 min.

Example 1

Preparation and Purification of Cyanocobalamin Monocarboxylates: Modification on the Corrin Ring This example serves to demonstrate the hydrolysis of b-, d- and e-propionamide sites on a vitamin $B_{12}$ molecule using dilute acid in preparation for coupling of a linker to the sites. Importantly, the hydrolysis of the b-, d- and e-propionamides is selective over the hydrolysis of a-, c- and g-acetamides, or the f-amide in the heterocyclic chain connecting the benzimidazole. An optimal yield of monocarboxylate to di- and tri-carboxylate derivatives was obtained at room temperature in 0.1 N HCl over a 10 day period. The non-hydrolyzed vitamin $B_{12}$ and the di- and tri-carboxylates produced were readily isolated from the desired monocarboxylates by preparative liquid chromatography.

Specifically, cyanocobalamin (1) (3.7 mmol, 5 g) was dissolved in 500 mL of 0.1 N HCl and stirred at room temperature for 10 days under argon atmosphere. The solution was then neutralized with 6 N NaOH and the cobamides were desalted by extraction into phenol and applied to a 200 g (60×4 cm, 200–400 mesh) Dowex $Cl^-$×2 column (acetate form; prepared by washing with saturated sodium acetate until it was free from $Cl^-$, then washing with 200 mL water). The column was eluted with water to remove unreacted cyanocobalamin and then eluted with 0.04 M sodium acetate (pH 4.67).

The first fraction of the elution contained three monocarboxylic acids. These were desalted by extraction into 100 mL of 90% (w/w) phenol, twice with 25 mL and once with 10 mL of phenol. Three volumes of ethyl ether (3×160 mL) and 1 volume of acetone (160 mL) were added to the combined phenol extracts. Monocarboxylic acids were removed from the organic phase by extraction with water (2×100 mL). The combined aqueous phases were extracted twice with 20 mL of ether to remove residual phenol. The aqueous solution of monocarboxylic acids was evaporated to dryness.

Yield: 2.5 g (50%).

The mixture of three acids (0.350 g) was then applied to a 200 g (1000 mm×25 mm) column of aminopropyl coated silica (40–63 mm) and was eluted with 58 mM pyridine acetate pH 4.4 in $H_2O$: THF (96:4); the elute was collected with an automatic fraction collector. The first eluted acid was found to be b-monocarboxylic acid (2), the second eluted acid was e-monocarboxylic acid (3) and the third eluted acid was d-monocarboxylic acid (4). The acid fractions were desalted by phenol extraction. The solids obtained were crystallized from aqueous acetone.

b-acid (2): yield 0.122 g (35%), mp 267–270° C. with decomposition, $^1H$ NMR (MeOH-$d_4$, δ) 0.43 (s, 3H, C-20 $CH_3$); 1.00 (m, 2H); 1.18 (s, 3H, C-46 $CH_3$); 1.24 (d, 3H, $Pr_3$ $CH_3$); 1.36 (br s, 9H, C-47 $CH_3$, C-54 $CH_3$); 1.4 (s, 3H, C-25 $CH_3$); 1.9 (d, 7H, C-36 $CH_3$, C-30 $CH_2$, C-48 $CH_2$); 2.26 (d, 6H, B10 & B11, $CH_3$); 2.36 (d, 2H, C-26 $CH_2$); 2.57 (s, 10H, C-35 $CH_3$, C-31 $CH_2$, C-37 $CH_2$, C-53 $CH_3$); 2.8 (m, 2H, C-60 $CH_2$); 3.3 (m, 3H, C-8H, C-13H); 3.6 (m, 2H, Pr, $CH_2$); 3.7 (d, 1H, $R_5$); 3.9 (d, 1H, $R_5$); 4.0 (m, 1H, $R_4$); 4.12 (d, 1H, C-19); 4.17 (s, 1H, C-3); 4.3 (m, 1H, $R_2$); 4.5 (m, 1H); 4.7 (m, 1H, $R_3$); 6.0 (s, 1H, C-10); 6.2 (s, 1H, $R_1$); 6.5 (s, 1H, B4); 7.1 (s, 1H, B2); 7.2 (s, 1H, B7). MS ($FAB^+$): m/e 1357 ($M^+$+1). IR (KBr): 3400, 3200, 2950, 2060, 1660, 1570, 1490, 1060 $cm^{-1}$. UV (MeOH):δ360 (ε23441)

e-acid (3): yield 0.168 g (48%), mp 245–250° C. with decomposition, $^1H$ NMR (MeOH-$d_4$, δ) 0.43 (s, 3H, C-20 $CH_3$); 1.01 (m, 2H); 1.15 (s, 3H, C-46 $CH_3$); 1.23 (d, 3H, $Pr_3$ $CH_3$); 1.36 (br s, 9H, C-47 $CH_3$, C-54 $CH_3$); 1.4 (s, 3H, C-25 $CH_3$); 1.83 (s, 4H, C-55 $CH_2$); 1.93 (m, 6H, C-36 $CH_3$, C-30 $CH_2$, C-48 $CH_2$); 2.22 (d, 6H, B10 & B11 $CH_3$); 2:35 (s, 3H, C-26 $CH_2$); 2.5 (d, 13H, C-35 $CH_3$, C-31 $CH_2$, C-37 $CH_2$, C-53 $CH_3$); 2.9 (m, 1H, C-60 H); 3.2 (m, 1H, C-13H); 3.4 (m, 1H, C-8 H); 3.6 (d, 1H, Pr1 CH); 3.7 (d, 1H); 3.9 (d, 1H); 4.0 (m, 2H); 4.1 (d, 1H); 4.2 (m, 2H); 4.6 (m, 1H); 6.0 (s, 1H, C-10); 6.3 (d, 1H, R1); 6.5 (s, 1H, B4); 7.0 (s, 1H, B2); 7.2 (s, 1H, B7). MS ($FAB^+$): m/e 1357 ($M^+$+1). IR((KBr): 3400, 3200, 2950, 2060, 1660, 1570, 1490, 1060 $cm^{-1}$. UV (MeOH): δ360 (ε21 842)]

d-acid (4): yield 0.060 g (17%), mp>300° C., 1H NMR (MeOH-$d_4$, δ) 0.43 (s, 3H, C-20 $CH_3$); 1.04 (m, 2H); 1.15 (s, 3H, C-46 $CH_3$); 1.25 (d, 3H, $Pr_3$ $CH_3$); 1.36 (br s, 9H, C-47 $CH_3$, C-54 $CH_3$); 1.4 (s, 3H, C-25 $CH_3$); 1.85 (s, 4H); 2.01 (s, 6H); 2.23 (d, 8H, B10 & B11 $CH_3$); 2.38 (d, 3H, C-26 $CH_2$); 2.53 (d, 13H, C-36 $CH_3$, C-30 $CH_2$, C-48 $CH_2$); 2.6 (m, 5H); 2.9 (m, 1H, C-60 H); 3.3 (d, 1H, C-13H); 3.4 (m, 1H, C-8 H); 3.6 (d, 1H, Pr, CH); 3.7 (d, 1H); 3.9 (d, 1H); 4.0 (m, 2H); 4.1 (d, 1H); 4.3 (m, 2H); 6.0 (s, 1H, C-10); 6.3 (d, 1H, R1); 6.5 (s, 1H, B4); 7.1 (s, 1H, B2); 7.2 (s, 1H, B7); UV (MeOH): δ360 (ε22 127). MS ($FAB^+$): m/e 1357 ($M^+$+ 1). IR (KBr): 3400, 3200, 2950, 2060, 1660, 1570, 1490, 1060 $cm^{-1}$.

Example 2

Cyanocobalamin Modified on Ribose: Succinate Conjugate (5)

This example serves to demonstrate the activation of the ribose coupling site coupling site h (see structure I) with succinic anhydide. Cyanocobalamin (1) (0.15 mmoL, 200 mg) was dissolved in 40 mL of dimethylsulfoxide (DMSO) containing 8 g (80 mmoL) of succinic anhydride and 6.4 mL of pyridine. After 14–16 h at room temperature, the excess of succinic anhydride was destroyed by adding 500 mL of water and keeping the pH of the reaction mixture at 6 with 10% KOH. KCN was then added at a final concentration of 0.01 M and the pH of the solution was readjusted to 6 with 3 N HCl. After 1 h the cyanocobalamin components were desalted by phenol extraction and applied to a 100 g of Dowex Cl⁻ (60×2.5 cm) column (acetate form, 200–400 mesh). The cyanocobalamin was eluted with water. Succinate conjugate (5) was eluted with NaOAc (0.04 M, pH 4.67) which yielded 180 mg (85%) after isolation. The O2',O5'-disuccinyl derivative remained absorbed on the column under these conditions. mp 208–210° C. with decomposition.

$^1$H NMR (D$_2$O-d$_4$, δ): 0.43 (s, 3H, C-20 CH$_3$); 0.95 (m, 2H); 1.15 (s, 3H); 1.2 (d, 3H); 1.35 (d, 7H); 1.4 (s, 3H); 1.8 (s, 3H); 1.9 (s, 12H); 2.2 (d, 6H); 2.36 (d, 2H); 2.5 (d, 10H); 2.6–2.7 (m, 7H); 3.0 (m, 1H); 3.3 (d, 1H); 3.37 (m, 1H); 3.5 (d, 1H); 4.0 (d. 1H); 4.18 (m, 2H); 4.25 (m. 3H); 4.54 (d, 1H); 6.0 (s, 1H); 6.3 (d, 1H); 6.4 (s, 1H); 7.0 (s, 1H); 7.2 (s, 1H). MS (FAB$^+$): m/e 1455 (M$^+$+1). IR (KBr): 3400, 3200, 2950, 2060, 1660, 1570, 1490, 1060 cm$^{-1}$; UV (MeOH): δ360 (ε26041).

Example 3

Coupling of Cyanocobalamin Monocarboxylic Acids With 1,$_{12}$-Diaminododecane: Reaction Without Sodium Cyanide This example serves to demonstrate the coupling of a linker to a cyanocobalamin monocarboxylate. Coupling of the monocarboxylates (2, 3, 4) with diaminododecane was first attempted using N-ethyl-N'-dimethylamino-propyl-carbodiimide hydrochloride (EDC) in H$_2$O according to Yamada and Hogenkamp, J. Biol. Chem 247 6266–6270, 1972. However, the products obtained did not have a reactive amino group. Alteration of the reaction conditions by changing the reaction mixture to DMF/H$_2$O and adding NaCN/N-hydroxysuccinimide (see Example 4) to the reaction mixture gave the desired diaminododecane adducts.

A mixture of cyanocobalamin monocarboxylic acid (0.370 mmoL, 500 mg) and 1,12-diaminododecane (3.6 g) in 100 mL H$_2$O was adjusted to pH 6 with 1 N HCl. The solution was then treated with N-ethyl-N'-dimethylamino-propyl-carbodiimide-hydrochloride (EDC) (726 mg) and stirred at room temperature for 22 h. In 5 intervals of 6 to 14 h, 650 mg of EDC was added to the reaction mixture. After a total reaction time of 4 days (HPLC monitoring) the solution was evaporated to dryness, the residue was digested with 100 mL of acetone and the solvent was decanted. The solid residue was dissolved in 50 mL of water and applied to an 175 g Amberlite XAD-2 (60×4 cm) column. Contaminates were washed from the column with 1 L water, then the crude product was eluted with 500 mL of methanol. The solution was evaporated to dryness, the residue was dissolved in 25 mL of water and was applied to a 100 g Dowex Cl⁻ (60×2.5 cm) column (acetate form, 200–400 mesh). The final product was eluted using 250 mL of water, thereby leaving non-converted acid bound to the column, which was later eluted with 0.04 mol/L sodium acetate buffer pH 4.67. The fraction containing the final product was evaporated to dryness.

The mass spectral value obtained indicated that HCN was lost from the desired product. Further, $^1$H NMR data suggested that some protons were being affected by the cobalt. Thus, this reaction was conducted with NaCN (Example 4) to drive the equilibrium towards retention of Co—CN. N-hydroxy succinimide was also added to facilitate the coupling reaction.

e-acid adduct (6): Yield: 222 mg (40%). mp 172–174° C. with decomposition. $^1$H NMR (MeOH-d$_4$, δ): 0.43 (m, 3H, C-20 CH$_3$); 1.06 (t, 4H, C-46 CH$_3$); 1.16 (m, 5H); 1.2 (m, 5H); 1.33 (m, 7H); 1.43 (s, 3H); 1.68 (m, 4H); 1.86 (m, 5H); 2.2(m, 8H); 2.3 (m, 6H); 2.4 (m, 10H); 2.55 (m, 10H); 2.8 (m, 4H); 3.1 (m, 6H); 3.3 (m, 5H); 3.6 (m, 2H); 3.7 (m, 2H); 3.8 (m, l); 4.0 (m, 1); 4.1 (m, 1H); 4.16 (m, 1H); 4.3 (m, 1H); 4.48 (m, 1H); 4.6 (m, 1H); 6.0 (d 1H, C-10); 6.2 (m, 1H, R1); 6.5 (m, 1H, B4); 7.1 (m, 1H, B2); 7.2 (m, 1H, B7). MS (FAB$^+$): M/e 1512. IR (KBr): 3400, 3200,2950,1660,1570, 1490, 1060 cm$^{-1}$. UV (MeOH): δ360(ε21 877).

d-acid adduct (7): yield: 225 mg (45%), mp 195–198° C. with decomposition. $^1$H NMR (MeOH-d$_4$, δ): 0.43 (m, 3H, C-20 CH$_3$); 1.09 (m, 7H); 1.14 (m, 6H); 1.2 (m, 10H); 1.27 (m, 10H); 1.33 (m, 6H); 1.5 (m, 3H); 1.77 (s, 3H); 2.2 (m, 8); 2.26 (s, 2H); 2.5 (m, 10H); 2.7 (m, 51; 3.0 (m, 2H); 3.1 (m, 2H); 3.2 (m, 3H); 3.5 (m, 2H); 3.6 (m, 1H); 3.8 (m, 1H); 3.9 (m, 1H); 4.0 (m, 1H); 4.1 (m, 1H); 4.2 (m, 1H); 44 (m, 1H); 4.6 (m, 1H); 6.0 (d 1H, C-10); 6.1(m, 1H, R$_1$); 6.4 (m, 1H, B4); 7.0 (m, 1H, B2); 7.1 (m, 1H, B7); MS (FAB$^+$): m/e 1512, IR (KBr): 3400, 3200, 2950, 1660, 1570, 1490, 1060 cm$^{-1}$; UV (MeOH): δ360 (ε22 680).

Example 4

Coupling of Cyanocobalamin Monocarboxylic Acids With 1,$_{12}$-Diaminododecane: Reaction Containing Sodium Cyanide Cyanocobalamin monocarboxylic acid (2, 3, 4) (0.370 mmoL, 500 mg) and N-hydroxysuccinimide (1.48 mmoL, 170 mg) were dissolved in a mixture of DMF: H$_2$O (1:1) (18.4 mL) and 363 mg of NaCN was added. 1,12-Diaminododecane was dissolved in a mixture of DMF: H$_2$O (1:1) (18.4 mL) and the pH was adjusted to 6 with 1 N HCl. The diaminododecane solution was then added in one portion to the cyanocobalamin solution. EDC (285 mg) was added and the pH of the solution was readjusted to 5.5. The reaction mixture was then stirred overnight in the dark at room temperature. In 5 intervals of 6–14 h, 170 mg of N-hydroxysuccinimide and 285 mg of EDC were added to the solution, readjusting the pH value 5.5 each time. After a total reaction time of 4 days (reaction followed by HPLC), the solution was evaporated to dryness. The residue was digested with 100 mL of acetone and the solvent was decanted. The solid residue was dissolved in 50 mL of H$_2$O and applied to an 200 g Amberlite XAD-2 (60×4 cm) column. The column was eluted with 1 L water to remove undesired materials, then the desired product was eluted with 500 mL methanol. The solution was evaporated to dryness, the residue was dissolved in 25 mL of water and was applied to a 100 g Dowex Cl⁻ (60×2.5 cm) column (acetate form, 200–400 mesh). The desired product was eluted from the column with 250 mL water, leaving any non-reacted acid bound to the column. This was followed by elution with 0.04 mol/L sodium acetate buffer pH 4.7. The fractions containing the final product were evaporated to dryness.

b-isomer (8): yield 410 mg (82%), mp 172–174° C. with decomposition. $^1$H NMR (MeOH-d$_4$, δ) 0.43 (s, 3H, C-20 CH$_3$); 1.18 (s, 4H); 1.3 (m, 13H); 1.39 (m, 13H); 1.45 (s, 5H); 1.6 (m, 4H); 1.72 (m, 2H); 1.9 (s, 6H); 2.25 (d, 6H, B10 & B11 CH$_3$); 2.35 (m, 5H); 2.56 (m, 5H); 2.8–3.0 (m, 8H); 3.15 (m, 4H); 3.3 (m, 2H); 3.4 (m, 2H); 3.6 (m, if); 3.68 (m, 1H); 3.75 (m, 1H); 3.9 (d, 1H); 4.07 (m, 1H); 4.12 (d, 1H); 4.2 (br s, 1H); 4.3 (m, 1H); 4.47 (m, 1H); 4.7 (m, 1H); 6.0 (s, 1H, C-10); 6.2 (d, 1H, R$_1$); 6.5 (s, 1H, B4); 7.1 (s, 1H, B2); 7.2 (s, 1H, B7); MS (FAB$^+$): m/e 1539 (M$^+$+1). IR (KBr): 3400, 3200, 2950, 2060, 1660, 1570, 1490, 1060 cm$^{-1}$. UV (MeOH): δ360 (ε15409).

e-isomer (9): yield: 430 mg (86%), mp 175–180° C. with decomposition, $^1$H NMR (MeOH-d$_4$, δ) 0.43 (s, 3H, C-20 CH$_3$); 1.17 (s, 4H, C-46 CH$_3$); 1.22 (d, 4H, Pr$_3$ CH$_3$); 1.29 (s, 24H); 1.36 (br s, 6H); 1.4 (s, 6H); 1.6 (m, 3H); 1.87 (s, 8H); 2.05 (m, 2H); 2.25 (s, 6H, B10 & B11 CH$_3$); 2.36 (m, 3H); 2.55 (d, 10H); 2.8 (s, 4H); 3.06 (m, 2H); 3.1 (m, 3H); 3.3 (s, 1H); 3.34 (m, 1H); 3.4 (m, 1H); 3.58 (m, 1H); 3.65 (m, 1H); 3.75 (d, 1H); 3.9 (d, 1H); 4.0 (m, 1H); 4.1 (d, 1H); 4.16 (m, 1H); 4.3 (m, 2H); 4.48 (m, 2H); 4.6 (m, 1H); 6.0 (s, 1H, C-10); 6.3 (d, 1H, R$_1$); 6.5 (s, 1H, B4); 7.0 (s, 1H, B2); 7.2 (s, 1H, B7); MS (FAB$^+$): m/e 1539 (M$^+$+1). IR (KBr): 3400, 3200, 2950, 2060, 1660, 1570, 1490, 1060 cm$^{-1}$. UV (MeOH): δ360 (ε16 720)

d-isomer (10): yield: 400 mg (80%), mp 174–178° C. with decomposition, $^1$H NMR (MeOH-d$_4$, δ) 0.43 (s, 3H, C-20 CH$_3$); 1.07 (m, 3H, C-46 CH$_3$); 1.2 (d, 4H, Pr$_3$ CH$_3$); 1.27 (m, 15H); 1.35 (br s, 9H); 1.42 (s, 3H); 1.53 (m, 2H); 1.6 (m, 4H); 1.86 (s, 4H); 2.25 (d, 6H, B10 & B11 CH$_3$); 2.5 (d, 10H); 2.8 (s, 3H); 2.9 (m, 6H); 3.15 (m, 3H); 3.2 (m, 4H); 3.4 (m, 3H); 3.6 (d, 1H); 3.75 (d, 1H); 3.96 (d, 1H); 4.08 (m, 2H); 4.19 (m, 1H); 4.3 (m, 2H); 4.65 (m, 1H); 6.0 (s, 1H, C-10); 6.3 (d, 1H, R$_1$); 6.5 (s, 1H, B4); 7.1 (s, 1H, B2); 7.2 (s, 1H, B7); UV (MeOH): δ360 (ε17 665). MS (FAB$^+$): m/e 1539 (M$^+$+1). IR (KBr): 3400, 3200, 2950, 2060, 1660, 1570, 1490, 1060 cm$^{-1}$.

Example 5

Coupling of Cyanocobalamin Monocarboxylic Acids With Gamma-Aminobutyric Acid (GABA)

Figure 9:
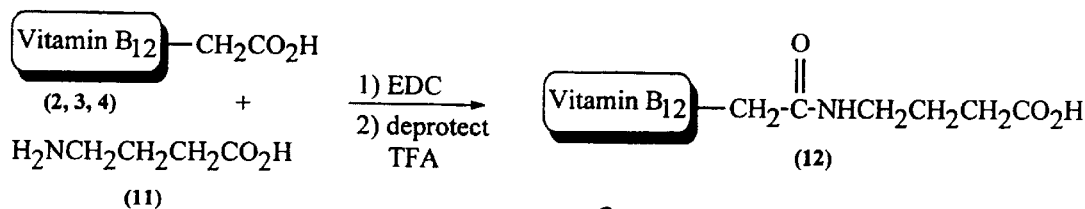
FIG. 9 is a schematic depicting a representative reaction scheme for the synthesis of a vitamin $B_{12}$-GABA adduct.
Figure 10A:
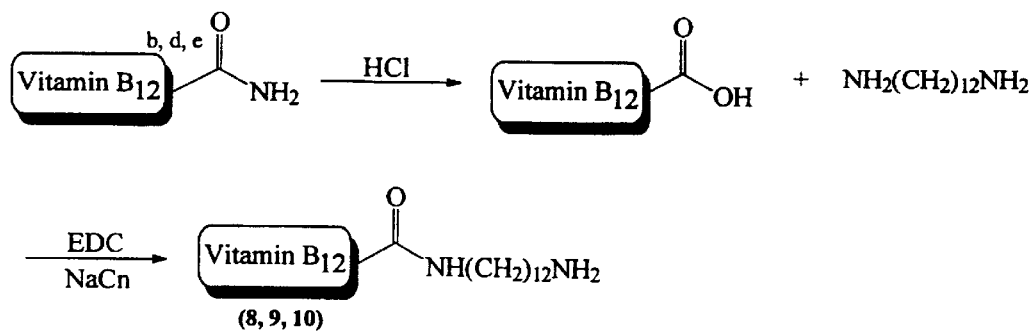
FIG. 10A is a schematic depicting a representative reaction scheme for the synthesis of a vitamin $B_{12}$ derivative comprising a vitamin $B_{12}$ molecule with a diaminododecane linker arm coupled to any one of coupling sites d-, e-, or b-.
Figure 10B:
FIG. 10B is a schematic depicting a representative reaction scheme for coupling a succinic anhydride to a vitamin $B_{12}$ diaminododecane adduct in preparation for coupling the adduct to a rerouting moiety, or other molecule, with an amino reaction site.

This example serves to demonstrate the coupling of a gamma-aminobutyric acid (GABA) linker to a vitamin B$_{12}$ molecule. This reaction scheme is represented in FIG. 9.

Gamma-aminobutyric acid (GABA) tert-butyl ester (11) (1 mmol) and cyanocobalamin monocarboxylates (2, 3, 4) (0.1 mmol.) are mixed in 20 mL H$_2$O and sufficient 0.1 N HCl is added to adjust to pH to 6.0. N-ethyl-N$^1$-dimethylaminopropylcarbodiimide hydrochloride (EDC) (0.5 mmol) is added to the solution. The reaction mixture is stirred at room temperature for 24 hours and then the mixture is dried under vacuum. This reaction mixture is treated with TFA to remove the tert-butyl ester. A cyanocobalamin-GABA adduct (12) was purified. Reverse-phase BPLC chromatography is carried out as described above. A cyanocobalamin-GABA adduct (12) can be further activated with a carbodiimide and coupled to a moiety as described below.

Example 6

Cyanocobalamin Modified on Ribose: Succinate-diaminododecane Conjugate (13)

Figure 11:
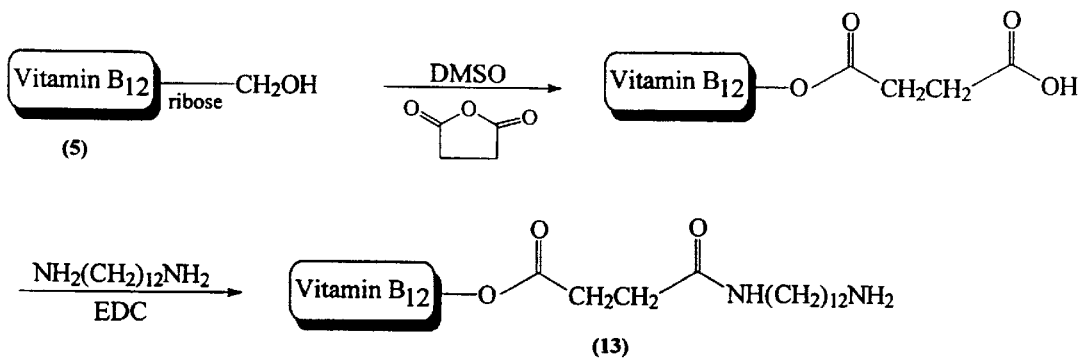
FIG. 11 is a schematic depicting a representative reaction scheme for the synthesis of a vitamin $B_{12}$ derivative comprising a vitamin $B_{12}$ molecule and a diaminododecane linker arm coupled to a ribose coupling site.

Cyanocobalamin-Ribose-Succinate (5) (0.370 mmoL, 538 mg) and N-hydroxylsuccinimide (1.48 mmoL, 170 mg) were dissolved in a mixture of DMF: H$_2$O (1:1) (18.4 mL) and 363 mg of NaCN was added. This reaction scheme is represented in FIG. 11. 1,$_{12}$-Diaminododecane was taken in a mixture of DMF: H$_2$O (1:1) (18.4 mL), pH was adjusted to 6 with IN HCl. The diaminododecane solution was then added in a portion to the cyanocobalamin solution. EDC (285 mg) was added, the pH of the solution was readjusted to 5.5 and the reaction mix. was stirred overnight in the dark at room temperature. In 5 intervals of 6 to 14 h 170 mg of N-hydroxysuccinimide and 285 mg of EDC was added to the solution, readjusting the pH 5.5 each time. After a total reaction time of 4 days (HPLC monitored) the solution was evaporated to dryness, the residue was digested with 100 mL of acetone and the solvent was decanted. The solid residue was dissolved in 50 mL of H$_2$O and applied to an 200 g Amberlite XAD-2 (60×4 cm) column. Contaminates were washed from the column with 1 L water and then the crude product was eluted with 500 mL methanol. The solution was evaporated to dryness, the residue was dissolved in 25 mL of water and was applied to a 100 g Dowex Cl$^-$ (60×2.5 cm) column (acetate form, 200–400 mesh). The final product was eluted using 250 mL water, thereby leaving non-converted acid bound to the column, which was later eluted with 0.04 mol/L sodium acetate buffer pH 4.7. The fraction containing the final product (13) was evaporated to dryness. Yield 425 mg (70%), mp 185–187° C. with decomposition.

$^1$H NMR (MeOH-d$_4$, δ): 0.43 (s, 3H, C-20 CH$_3$); 1.15 (s, 3H); 1.2 (d, 3H); 1.3 (s, 27H); 1.4 (m, 3H); 1–55 (m, 6H); 1.85 (m, 12H); 2.2 (d, 6H); 2.3 (d, 6H); 2.5 (d, 10H); 2.8 (m, 10H); 3.0 (t, 3H); 3.1 (t, 3H); 3.2 (s, 6H); 3.3 (m, 4H); 3.58 (m, 2H); 3.6 (d, 1H); 4.1 (d. 1H); 4.2 (m, 2H); 4.3 (m, 1H); 4.4 (d, 1H); 6.0 (s, 1H); 6.2 (d, 1H); 6.5 (s, 1H); 7.1 (s, 1H); 7.2 (s, 1H). MS (FAB$^+$): m/e 1638 (M$^+$). IR (KBr): 3400, 3200, 2950, 2060, 1660, 1570, 1490, 1060 cm$^{-1}$; UV (MeOH): δ360.

Example 7

Modification of Cyanocobalamin Monocarboxylic Acids Conjugated With 1,$_{12}$-diaminododecane: Reaction With Succinic Anydride This example serves to demonstrate modification of an amino terminus linking moiety to a carboxylate terminus. Such a modification may be necessary for conjugating amino containing rerouting agents (e.g., aminosugars) to cyanocobalamin derivatives containing a linker.

Cyanocobalamin carboxylic acid diaminododecane conjugate (8, 9, 10) (0.138 mmoL, 200 mg) was dissolved in 40 mL of dimethylsulfoxide (DMSO) containing 8 g (80 mmoL) of succinic anhydride and 6.4 mL of pyridine. After 14–16 h at room temperature, the excess of succinic anhydride was destroyed by adding 500 mL of water and keeping the pH of the reaction mixture at 6 with 10% KOH. KCN was then added at a final concentration of 0.01 M and the pH of the solution was readjusted to 6 with 3 N HCl. After 1 h the cyanocobalamin components were desalted by phenol extraction. The residue was digested with 100 mL of acetone and the solvent was decanted. It was dissolved in 40 mL of H$_2$O. IN NaOH (2 mL) was added to it and the reaction was stirred at room temperature for 15–20 min. It was then neutralized with 1N HCl and the cyanocobalamin components (14, 15, 16) were desalted by phenol extraction. Yield: 80 mg (40%); mp 190–198° C. with decomposition.

$^1$H NMR (MeOH-d$_4$, δ): 0.43 (s, 3H, C-20 CH$_3$); 1.17 (s, 4H, C-46 CH$_3$); 1.23 (d, 4H, Pr$_3$ CH$_3$); 1.29 (s, 24H); 1.36 (br s, 6H); 1.4 (s, 6H); 1.87 (s, 4H); 2.05 (m, 2H); 2.25 (s, 6H, B10 & B11 CH$_3$); 2.35 (m, 3H); 2.4 (m, 5H); 2.55 (d, 10H); 2.7 (s, 5H); 2.8 (m, 2H); 3.1 (m, 6H); 3.3 (s, 6H); 3.4 (m, 1H); 3.65 (m, 2H); 3.75 (d, 1H); 3.9 (d, 1H); 4.0 (m, 1H); 4.1 (d, 1H); 4.16 (m, 1H); 4.3 (m, 1H); 4.48 (m, 1H); 4.6 (m, 2H); 6.0 (s, 1H, C-10); 6.3 (d, 1H, R$_1$); 6.5 (s, 1H, B4); 7.1 (s, 1H, B2); 7.2 (s, 1H, B7). MS (FAB$^+$): m/e 1639 (M$^+$). IR (KBr): 3400, 3200, 2950, 2060, 1660, 1570, 1490,1060 cm$^{-1}$. UV (MeOH): δ360 (ε22 564).

Example 8

Cyanocobalamin Modified on Monocarboxylic Acid: Diaminododecane-biotin Conjugates This example serves to demonstrate coupling a vitamin B$_{12}$ derivative and biotin. Biotin conjugates (17, 18, 19)

were obtained by reaction of activated cyanocobalamin monocarboxylic acid diaminododecane (14), (15), and (16) with the NHS ester of biotin (Sigma Chemical Co.).

To a solution of cyanocobalamin monocarboxylic acid diaminododecane conjugate (14, 15, 16) (300 mg, 0.195 mmoL) in DMF (35 mL), was added triethylamine (0.027 mL, 0.195 mmoL). N-Hydroxysuccinimidobiotin (100 mg, 0.295 mmoL) was then added over a period of 10–15 min and evaporated to dryness. The solid residue was dissolved in 20 mL of water and applied to an 75 g of Dowex Cl⁻ (40×2 cm) (acetate form, 200–400 mesh) column. The product was eluted using 250 mL of water. It was then evaporated to dryness, the residue was dissolved in a 10 mL of methanol-water (7:3 v/v) and the solution was applied to a reverse phase C-18 column (500 mm×25 mm, Alltech, 150 psi) which was developed with the same solvent. RAIN Rabbit-plus peristaltic pumping system was used with a DYNAMAX (model UV-1) UV visible absorbance detector. The eluate was collected with an automatic fraction collector. The fractions containing the final product (HPLC monitored) were evaporated to dryness.

b-isomer (17): yield 159 mg (53%), mp 210–212° C. with decomposition, $^1$H NMR (MeOH-d$_4$, δ): 0.43 (s, 3H, C-20 CH$_3$); 1.18 (s, 4H); 1.3 (m, 13H); 1.39 (m, 13H); 1.45 (s, 5H); 1.6 (m, 4H); 1.72 (m, 2H); 1.9 (s, 6H); 2.2 (d, 8H, B10 & B11 CH$_3$); 2.6 (d, 12H); 2.7 (m, 3H); 2.8–3.0 (m, 8H); 3.1 (m, 3H); 3.2 (m, 2H); 3.4 (s, 1H); 3.6 (m, 2H); 3.68 (d, 1H); 3.75 (m, 1H); 3.9 (d, 1H); 4.07 (m, 1H); 4.12 (d, 1H); 4.2 (s, 1H); 4.3 (m, 1H); 4.47 (m, 1H); 4.7 (m, 1H); 6.0 (s, 1H, C-10); 6.2 (d, 1H R1); 6.5 (s, 1H, B4); 7.1 (s, 1H, B2); 7.2 (s, 1H, B7); MS (FAB$^+$): m/e 1764 (M$^+$). IR (KBr): 3400, 3200, 2950, 2060, 1660, 1570, 1490, 1060 cm$^{-1}$. UV (MeOH): λ360 (ε23 746).

Anal. Calcd. for $C_{85}H12_7N_{17}O_{16}CoPS.11H_2O$: C, 51.98; H. 7.59; N, $_{12}$.13. Found: C, 51.91; H 7.81; N, 12.31.

e-isomer (18): yield 174 mg (58%), mp 222–224° C. with decomposition, $^1$H NMR (MeOH-d$_4$, δ): 0.43 (s, 3H, C-20 CH$_3$); 1.17 (s, 4H, C-46 CH$_3$); 1.22 (d, 4H, Pr$_3$ CH$_3$); 1.29 (s, 24H); 1.36 (br s, 6H); 1.4 (s, 6H); 1.6 (m, 4H); 1.72 (m, 2H); 1.87 (s, 4H); 2.17 (m, 3H); 2.25 (s, 6H, B10 & B11 CH$_3$); 2.36 (m, 3H); 2.55 (d, 10H); 2.64 (m, 2H); 2.8 (s, 4H); 2.97 (s, 4H); 3.1 (m, 3H); 3.3 (m, 1H); 3.4 (m, 1H); 3.58 (m, 1H); 3.65 (m, 1H); 3.75 (d, 1H); 3.9 (d, 1H); 4.0 (m, 1H); 4.1 (d, 1H); 4.16 (m, 1H); 4.3 (m, 2H); 4.48 (m, 2H); 4.6 (m, 1H); 6.0 (s, 1H, C-10); 6.3 (d, 1H, R1); 6.5 (s, 1H, B4); 7.0 (s, 1H, B2); 7.2 (s, 1H, B7); MS (FAB$^+$): m/e 1764 (M$^+$). IR (KBr): 3400, 3200, 2950, 2060, 1660, 1570, 1490, 1060 cm$^{-1}$. UV (MeOH): λ360 (ε24 441).

Anal. Calcd. for $C_{85}H12_7N_{17}O_{16}CoPS.9H_2O$ (13): C, 52.96; H. 7.53; N, $_{12}$.35. Found: C, 52.85; H, 7.55; N, $_{12}$.30.

d-isomer (19): yield 165 mg (55%), mp 216–218° C. with decomposition, $^1$H NMR (MeOH-d$_4$, δ): 0.43 (s, 3H, C-20 CH$_3$); 1.16 (s, 3H, C-46 CH$_3$); 1.2 (d, 4H, Pr$_3$ CH$_3$); 1.28 (s, 15H); 1.35 (br s, 9H); 1.42 (s, 3H); 1.53 (m, 2H); 1.6 (m, 4H); 1.72 (m, 2H); 1.86(s, 6H); 2.16(m, 33H); 2.02(m, 4H); 2.25(d, 6H, B10 & B11 CH$_3$); 2.5 (d, 10H); 2.7 (d, 1H); 2.8 (m, 5H); 3.1 (m, 6H); 3.2 (m, 3H); 3.4 (m, 1H); 3.57 (m, 1H); 3.6 (d, 1H); 3.7 (d, 1H); 3.9 (d, 1); 4.0 (m, 1H); 4.11 (d, 1H); 4.17 (m, 1H); 4.3 (m, 2H); 4.4 (m, 2H); 4.6 (m, 1H); 6.0 (s, 1H, C-10); 6.3 (d, 1H, R1); 6.5 (s, 1H, B4); 7.1 (s, 1H, B2); 7.2 (s, 1H, B7); MS (FAB$^+$): m/e 1764 (M$^+$); IR (KBr): 3400, 3200, 2950, 2060, 1660, 1570, 1490, 1060 cm$^{-1}$; UV (MeOH): λ360 (ε29 824).

Anal. Calcd for $C_{85}H_{12_7}N_{17}O_{16}CoPS.10H_2O$: C, 52.46; H. 7.56; N, $_{12}$.24. Found: C, 52.27; H. 7.56; N, $_{12}$.34.

Example 9

Cyanocobalamin Modified On Ribose: Succinate-diaminododecane-biotin Conjugate (20)

This example serves to demonstrate the conjugation of the ribose-linked diaminododecane adduct (13) with biotin to produce a cyanocobalamin biotin conjugate (20).

To a solution of (11) (300 mg, 0.183 mmoL) in DMF (35 mL), triethylamine (0.025 mL, 0.183 mmoL) was added. N-hydroxysuccinimidobiotin (100 mg, 0.295 mmoL) was added over a period of 10–15 min. and then evaporated to dryness. The solid residue was dissolved in 20 mL of water and adjusted to pH 10 with 1N NaOH and applied to an 75 g Dowex Cl⁻ (40×2 cm) (200–400 mesh) column. The water fraction was discarded. The product was then eluted with 0.1N NH$_4$OAc and was desalted by phenol extraction. The residue was dissolved in a 10 mL of methanol-water (7:3 v/v) and the solution was applied to a reverse phase column (octadecyl) which was developed with the same solvent. The fractions containing the final product (20) (HPLC monitored) were evaporated to dryness. Yield 135 mg (45%), mp 198–205° C. with decomposition.

$^1$H NMR (MeOH-d$_4$, δ): 0.43 (s, 3H, C-20 CH$_3$); 1.15 (s, 3H); 1.2 (d, 3H); 1.3 (s, 27H); 1.36 (m, 6H); 1.4 (m, 3H); 1.6 (m, 4H); 1.7 (m, 2H); 1.85 (m, $_{12}$H); 2.0 (d, 3H); 2.17 (m, 3H); 2.2 (d, 6H); 2.3 (d, 6H); 2.5 (d, 10H); 2.64 (m, 2H); 2.8 (m, 10H); 3.1 (m, 6H); 3.25 (m, 6H); 3.58 (m, 2H); 4.0 (m, 1H); 4.1 (m, 1H); 4.16 (m, 1H); 4.4 (m, 1H); 4.6 (s, 2H); 4.7 (m, 1H); 6.0 (s, 1H); 6.2 (d, 1H); 6.5 (s, 1H); 7.1 (s, 1H); 7.2 (s, 1H). MS (FAB$^+$): m/e 1866 (M$^+$). IR (KBr): 3400, 3200, 2950, 2060, 1660, 1570, 1490, 1060 cm$^{-1}$. UV (MeOH): λ360 (ε28 434).

Example 10

Figure 13:
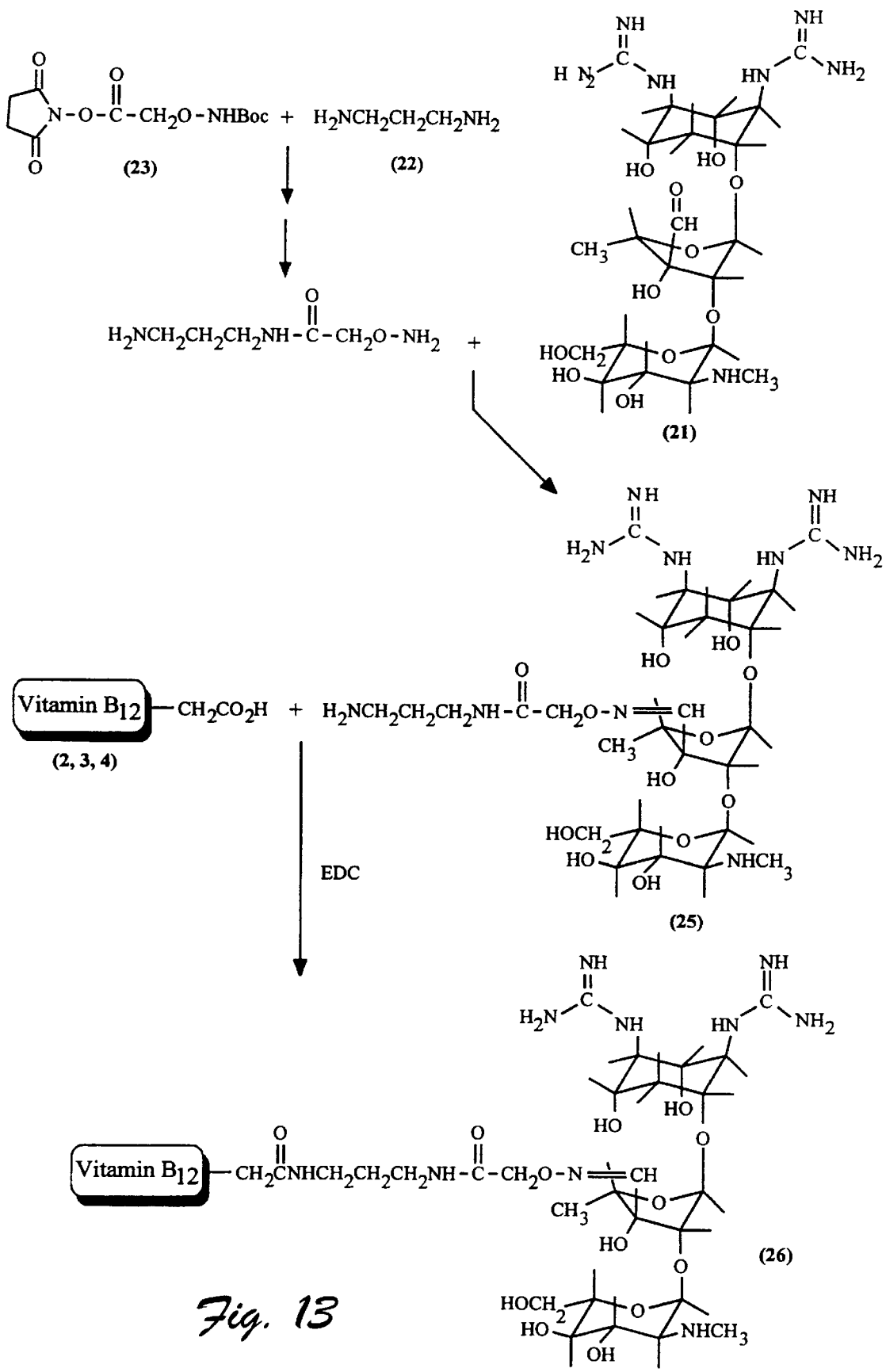
FIG. 13 is a schematic depicting a representative reaction scheme for coupling vitamin $B_{12}$ or a vitamin $B_{12}$-GABA adduct to streptomycin.

Synthesis of a Cyanocobalamin/lysosomotropic Compound (Streptomycin) Receptor Modulating Agent This example demonstrates coupling of streptomycin to a cyanocobalamin or cobalamin derivative. Streptomycin (21) is conjugated with cyanocobalamin monocarboxylate (2, 3, 4) or a diaminoalkylsuccinate derivative (14, 15, 16) through the use of an oxime coupled linking moiety (FIG. 13). The linking group, ((3-aminopropyl)aminoxy)acetamide (22) is prepared by reaction of the N-hydroxysuccinimidyl ester of 1,1-dimethylethoxycarbonyl-aminooxyacetic acid (23) (J. Med. Chem. 36:$_{12}$55–$_{12}$6, 1993) with an excess of diaminopropane in anhydrous THF. The linking group is separated from other compounds in the reaction mixture by preparative chromatography. The linker (1 g) is then mixed with streptomycin (0.5 g) in 10 mL of H$_2$O containing sodium acetate. The aqueous solution is warmed in a H$_2$0 bath for 10 minutes to yield a crude streptomycin-linker adduct (25) which may be purified by chromatography on acid washed alumina (J. Am. Chem. Soc. 68:1460, 1946). The aqueous solution containing the streptomycin linker adduct (0.15 mmol) is mixed with an aqueous solution of activated cyanocobalamin (2, 3, 4) (01. mmol) and EDC (0.5 mmol) is added. The reaction mixture is stirred at room temperature for 24 hours, then run over a reversed-phase preparative chromatography column for purification of the cyanocobalamin-streptomycin receptor modulating agent (26).

Example 11

Figure 14:
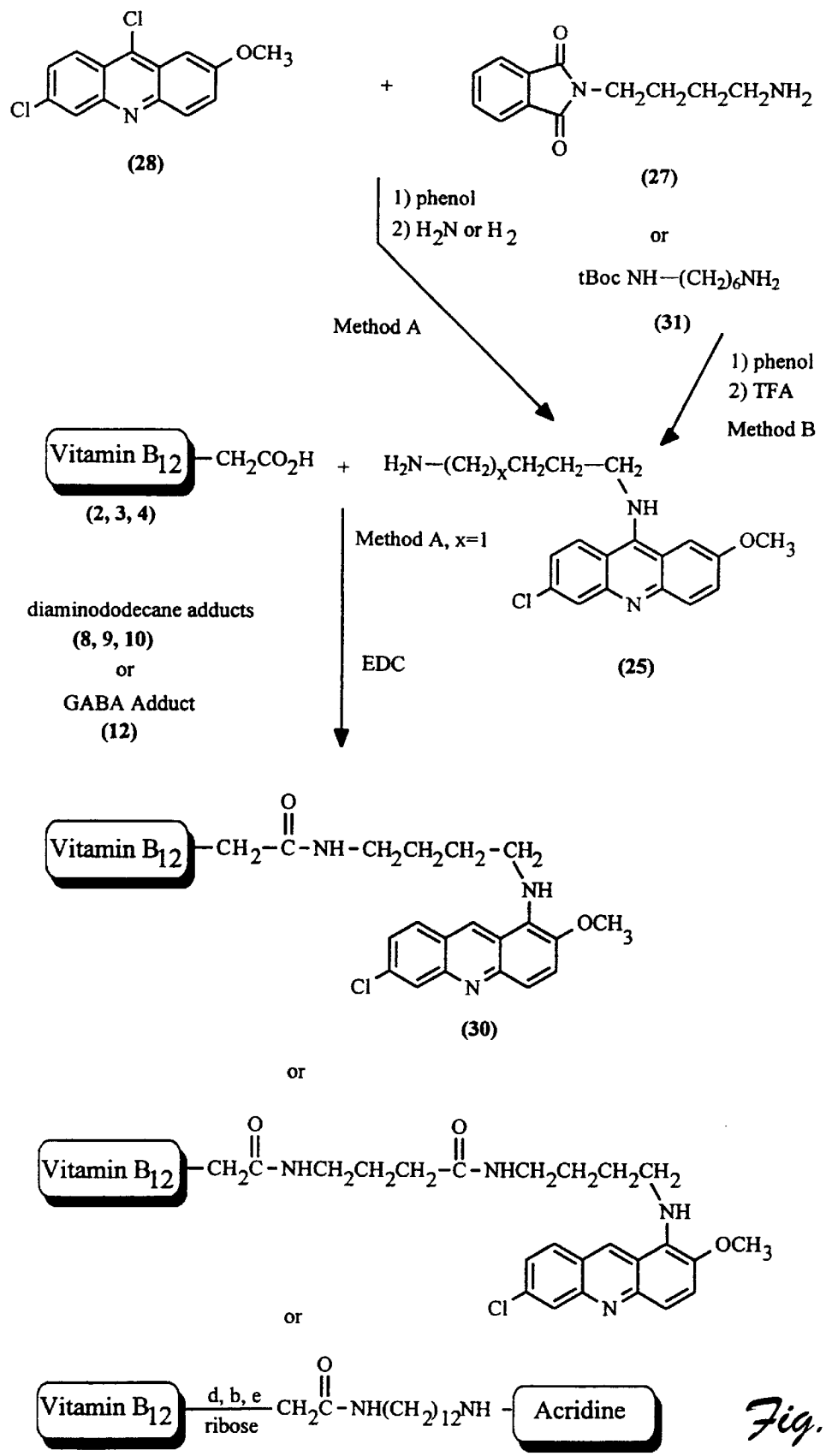
FIG. 14 is a schematic depicting a representative reaction scheme for coupling a vitamin $B_{12}$ carboxylate derivative or a vitamin $B_{12}$-GABA adduct to acridine.

Synthesis of a Cyanocobalamin/lysosomotropic Compound (Acridine) Receptor Modulating Agent This example demonstrates the coupling of the vitamin B$_{12}$ to acridine. Chloroquine, quinacrine and acridine are lysosomotropic dyes which are relatively non-toxic and concentrated as much as several hundred fold in lysosomes. Acridine derivatives may be covalently attached to a targeting moiety (such as cyanocobalamin) by the reaction scheme illustrated in FIG. 14, method A, or similarly as described in method B. Both reaction schemes produce a cyanocobalamin-acridine conjugate.

Method A: A diamine side chain is first synthesized in a manner analogous to the side chain of quinacrine. Specifically, mono-phthaloyl protected 1,4-diaminobutane (27) is reacted with 6,9-dichloro-2-methoxyacridine (28) in phenol (*J. Am. Chem. Soc.* 66:1921–1924, 1944). The reaction mixture is then poured into an excess of 2 N NaOH and extracted with ether. The ether extract is washed with 1 M $NaHCO_3$, then $H_2O$, and dried over $MgSO_4$. The crude product is recrystallized from $H_2O$-alcohol. The phthaloyl protecting group is removed using anhydrous hydrazine in MeOH (*Bioconjugate Chem.* 2:435–440, 1991) to yield the aminoacridine, (29). Aminoacridine (29) is then conjugated with vitamin $B_{12}$ monocarboxylic acid (2, 3, 4) to yield a cyanocobalamin-acridine conjugate (30).

Method B: Acridine derivative (31) (0.098 mmol, 0.045 g) was dissolved in 0.5 mL of trifluoroacetic acid. This solution was stirred at room temperature for 0.5 h. TFA was removed by aspirator vacuum. The residue was dissolved in 5 mL of acetonitrile and was neutralized by few drops of triethylamine. Acetonitrile was then removed by aspirator vacuum. The residue was dissolved in DMSO (10 mL) and cyanocobalamin carboxylic acid-diaminododecane-succinyl derivative (15, 16, 17) (0.098 mmol, 134 mg) was added followed by triethylamine ($_{12}$ μL). The reaction mixture was then stirred at room temperature for 24 h. (HPLC monitored), and evaporated to dryness. The residue was digested with 100 mL of acetone and the solvent was decanted yielding a cyanocobalamin-acridine conjugate (32). Yield: $_{12}$0 mg (62%). mp 182–188° C.

$^1$H NMR (MeOH-$d_4$, δ): 0.43 (s, 3H, C-20 $CH_3$); 1.17 (s, 4H, C-46 $CH_3$); 1.23 (d, 4H, $Pr_3$ $CH_3$); 1.29 (s, 24H); 1.36 (br s, 6H); 1.4 (s, 6H); 1.65 (m-2H); 1.87 (s, 4H); 2.05 (m, 2H); 2.25 (s, 6H, B10 & B11 $CH_3$); 2.35 (m, 3H); 2.4 (d, 5H); 2.44 (d, 2H); 2.55 (d, 10H; 2.64 (s, 5H); 2.8–2.9 (m, 8H); 3.1–3.15 (m, 6H); 3.3 (s, 6H); 3.4 (m, 1H); 3.65 (m, 2H); 3.75 (d, 1H); 3.9 (d, 1H); 3.98 (s, 2H); 4.0 (m, 2H); 4.1 (d, 1H); 4.16 (m, 1H); 4.3 (m, 1H); 4.48 (m, 1H); 4.6 (m, 2H); 6.0 (s, 1H, C-10); 6.3 (d, 1H, $R_1$); 6.5 (s, 1H, B4); 7.1 (s, 1H, B2); 7.2 (s, 1H, B7); 7.3 (t, 1H); 7.4 (dd, 1H); 7.6 (dd, 1H); 7.7 (2dd, 2H); 7.8 (d, 1H); 7.9 (d, 1H); 8.4 (d, 1H).

Example 12

Figure 12:
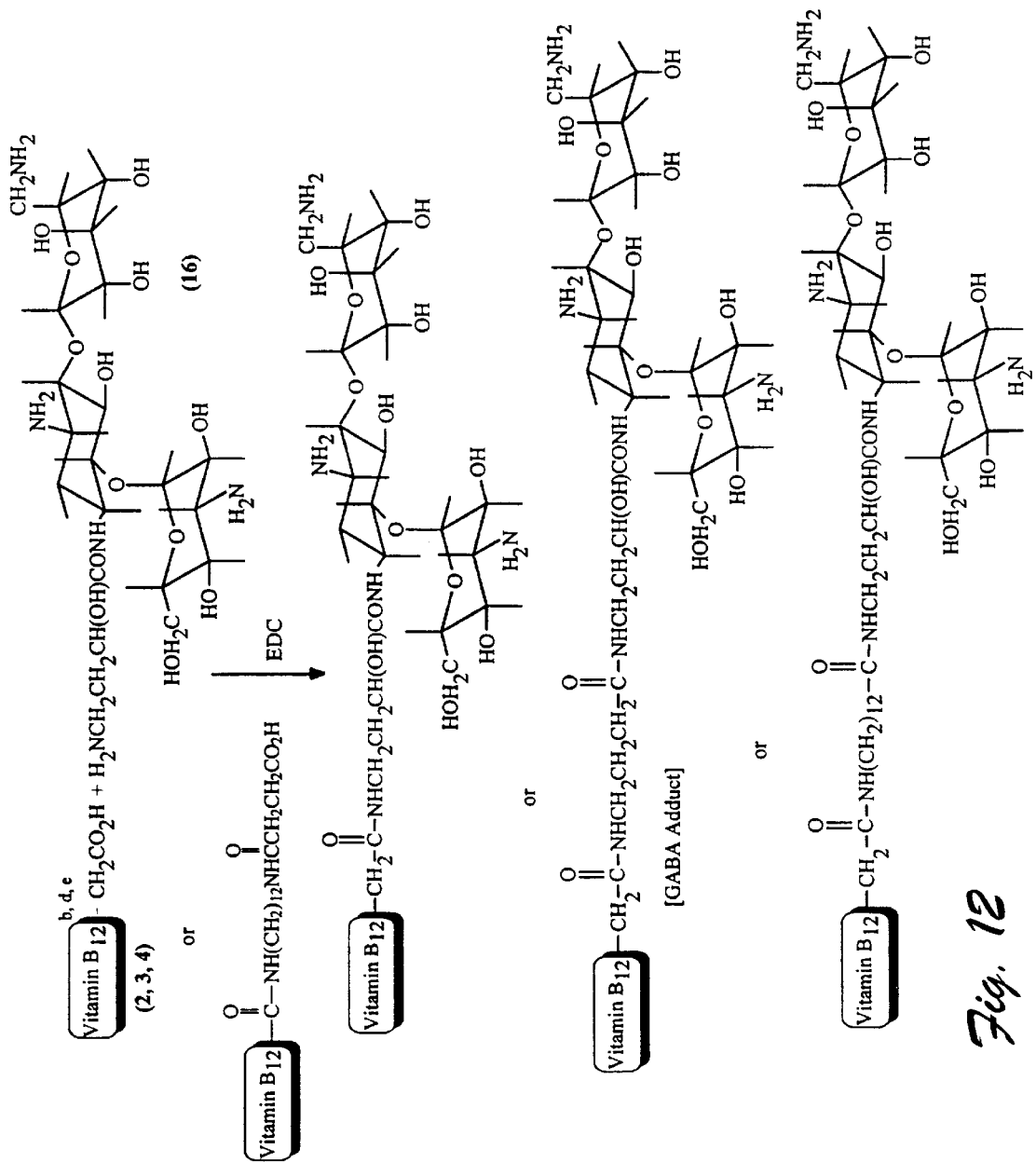
FIG. 12 is a schematic depicting a representative reaction scheme for coupling vitamin $B_{12}$ or a vitamin $B_{12}$-GABA adduct to amikacin.

Synthesis of a Cyanocobalamin/lysosomotropic Compound (Amikacin) Receptor Modulating Agent This example demonstrates conjugation of amikacin to a cyanocobalamin molecule to form a cyanocobalamin-amikacin conjugate. A reaction scheme for the conjugation is depicted in FIG. 12. As noted above, chemical moieties that are retained subcellularly within lysosomes are termed lysosomotropic. Aminoglycosides are lysosomotropic compounds, and thus may be used as rerouting moieties of this invention. The primary long chain amine on the hydroxyaminobutyric acid side chain of the aminoglycoside, amikacin (see FIG. 3), is preferentially reactive. Specifically, amikacin (33) (Sigma Chemical Co., St. Louis), is reacted with a vitamin $B_{12}$ monocarboxylate (2, 3, 4) in the presence of EDC. A cyanocobalamin-amikacin conjugate (34) is then separated and purified by reverse-phase LC chromatography under conditions noted above.

Example 13

Cyanocobalamin Monocarboxylic Acid Diaminododecane Conjugate Dimer: Isophthaloyl Dichloride Cross-linking This example demonstrates the production of a cyanocobalamin dimer suitable for use as a cross-inking receptor modulating agent. Cross-linking of receptors in some receptor systems is sufficient to cause a rerouting of cell surface receptors to lysosomes for degradation, rather than their normal pathway of receptor recycling.

To a solution of cyanocobalamin monocarboxylic acid diaminododecane conjugate (8, 9, 10) (0.192 mmol, 0.300 g) in DMF (30 mL), was added triethylamine (18 μL). Isophthaloyl dichloride (35) (0.096 mmol, 0.0195 g) was added over a period of 10–15 min. The reaction mixture was stirred at 55–60° C. for 48 h (HPLC monitored) and evaporated to dryness. The solid residue was dissolved in 20 mL of methanol: $H_2O$ (7:3) and applied to a reverse phase C-18 column (500 mm×25 mm, Alltech, 150 psi) which was developed with the same solvent. RAININ Rabbit-plus peristaltic pumping system was used with a DYNAMAX (model WV-1) UV visible absorbance detector; the elute was collected with an automatic fraction collector. The fractions containing the final product (HPLC monitored) were evaporated to dryness.

b-acid dimer (36): yield 96 mg (30%), mp 217–220° C. with decomposition, $^1$H NMR ($D_2O$, δ) 0.43 (s, 6H, C-20 $CH_3$); 1.18 (s, 8H); 1.3 (m, 36H); 1.37 (m, 12H); 1.46 (s, 10H); 1.6 (m, 8H); 1.9 (d, $_{12}$H); 2.05 (m, 10H); 2.2 (d, 16H, B10 & B11 $CH_3$); 2.35 (m, 8H); 2.6 (d, 18H); 2.8–3.0 (m, 16H); 3.15 (m, 6H); 3.3 (s, 8H); 3.37 (m, 14H); 3.6 (m, 4H); 3.76 (m, 2H); 3.9 (d, 2H); 4.07 (m, 2H); 4.$_{12}$ (m, 2H); 4.18 (m, 2H); 4–3 (m, 2H); 4.5 (m, 2H); 4.6 (s, 2H); 4.68 (m, 2H); 6.0 (s, 2H, 2C-10); 6.26 (d, 2H, 2R1); 6.6 (s, 2H, 2B4); 7.1 (s, 2H, 2B2); 7.25 (s, 2H, 2B7); 7.54 (t, 1H); 7.95 (d, 2H); 8.25 (s, 1H); MS (FAB$^+$): m/e 3208. IR (KBr): 3400, 3200, 2950, 2060, 1660, 1570, 1490, 1060 $cm^{-1}$; UV: λ360 (ε42 380).

e-acid dimer (37): yield 121 mg (38%), mp 220–222° C. with decomposition, $^1$H NMR ($D_2$, δ) 0.43 (s, 6H, C-20 $CH_3$); 1.17 (s, 8H); 1.22 (d, 13H); 1.29 (s, 45H); 1.36 (d, 22H); 1.44 (s, 10H); 1.6 (m, 8H); 1.87 (s, 8H); 2.04 (m, 10H); 2.25 (s, $_{12}$H, B10 & B11 $CH_3$); 2.36 (m, 8H); 2.55 (d, 20H); 2.8 (m, 8H); 3.15 (m, 8H); 3.29 (s, 10H); 3.36 (m, 14H); 3.6 (m, 4H); 3.73 (m, 2H); 3.9 (d, 2H); 4.07 (m, 2H); 4.$_{12}$ (m, 2H); 4.16 (m, 2H); 4.3 (m, 2H); 4.5 (m, 2H); 4.6 (s, 2H); 4.66 (m, 2H); 6.0 (s, 2H, 2C-10); 6.26 (d, 2H, 2R1); 6.6 (s, 2H, 2B4); 7.1 (s, 2H, 2B2); 7.25 (s, 2H, 2B7); 7.54 (t, 1H); 7.93 (d, 2H); 8.25 (s, 1H); MS (FAB$^+$): m/e 3208. IR (KBr): 3400, 3200, 2950, 2060, 1660, 1570, 1490, 1060 $cm^{-1}$. UV (MeOH): λ360 (ε33 854)

d-acid dimer (38): yield 96 mg (30%), mp 225–228° C. with decomposition, $^1$H NMR ($D_2$, δ) 0.43 (s, 6H, C-20 $CH_3$); 1.16 (s, 8H); 1.29 (m, 36H); 1.35 (d, $_{12}$H); 1.44 (s, 10H); 1.53 (m, 6H); 1.6 (m, 8H); 1.85 (s, 12H); 2.03 (m, 8H); 2.25 (d, $_{12}$H, B10 & B11 $CH_3$); 2.33 (m, 8H); 2.54 (d, 20H); 2.8 (m, 8H); 3.13 (m, 8H); 3.28 (s, $_{12}$H); 3.35 (m, 12H); 3.6 (m, 4H); 3.73 (m, 2H); 3.9 (d, 2H); 4.07 (m, 2H); 4.$_{12}$ (m, 2H); 4.16 (m, 2H); 4.3 (m, 2H); 4.5 (m, 2H); 4.64 (m, 2H); 4.7 (s, 2H); 6.0 (s, 2H, 2C-10); 6.26 (d, 2H, 2R1); 6.6 (s, 2H, 2B4); 7.1 (s, 2H, 2B2); 7.25 (s, 2H, 2B7); 7.54 (t, 1H); 7.93 (d, 2H); 8.25 (s, 1H); MS (FAB$^+$): m/e 3208. IR (K.Br): 3400, 3200, 2950, 2060, 1660, 1570, 1490, 1060 $cm^{-1}$ UV (MeOH): λ360 (ε31 747).

Example 14

Figure 15:
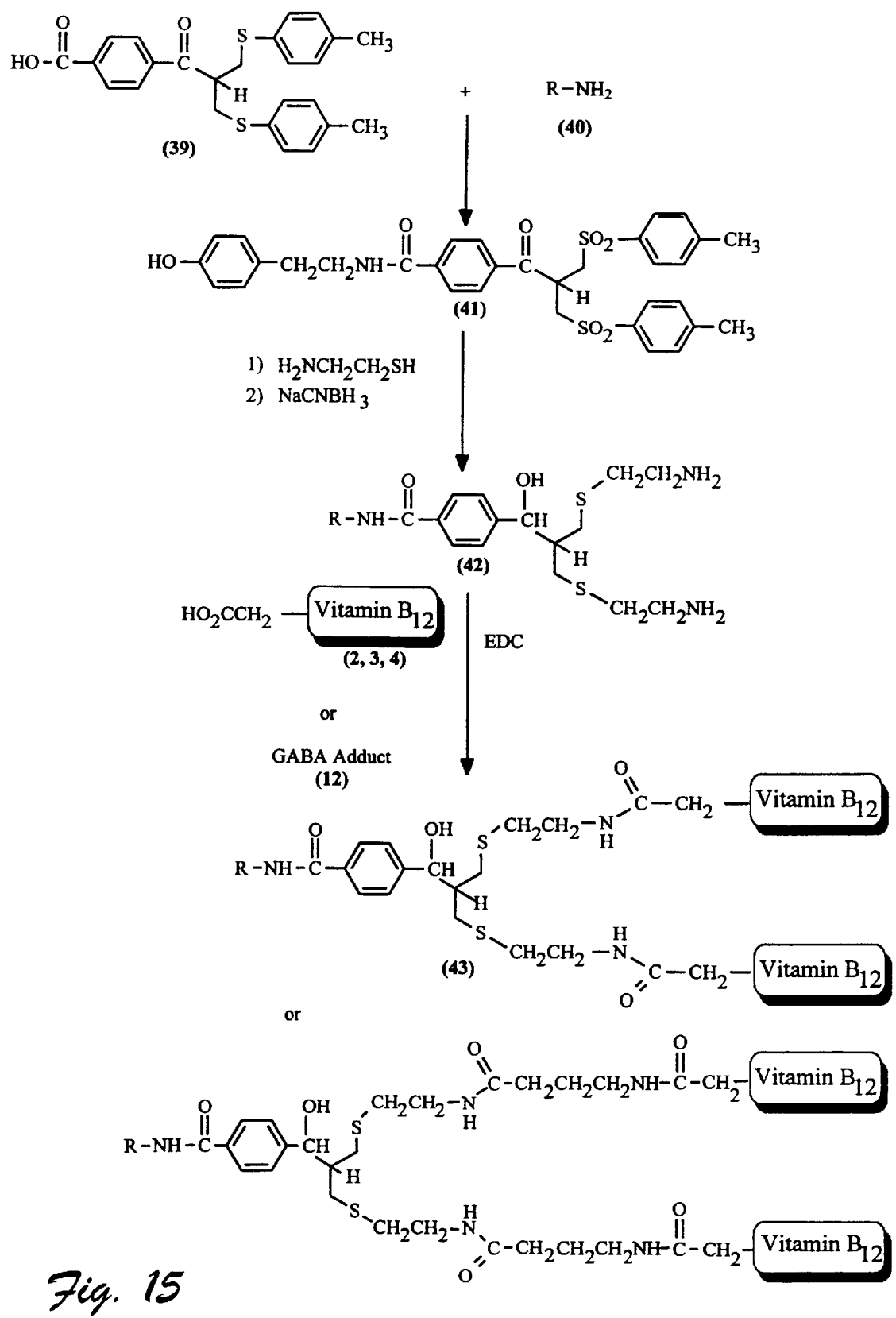
FIG. 15 is a schematic depicting a representative reaction scheme for the synthesis of a bivalent receptor modulating agent, a vitamin $B_{12}$ dimer, using a trifunctional linker. The trifunctional linker allows for coupling with additional compounds (e.g., R—$NH_2$) such as, by way of example, aminoglucosides (FIGS. 2–5), aminoacridines (FIG. 6), glycosylation inhibitors (FIG. 7), and biotin.
Figure 16:
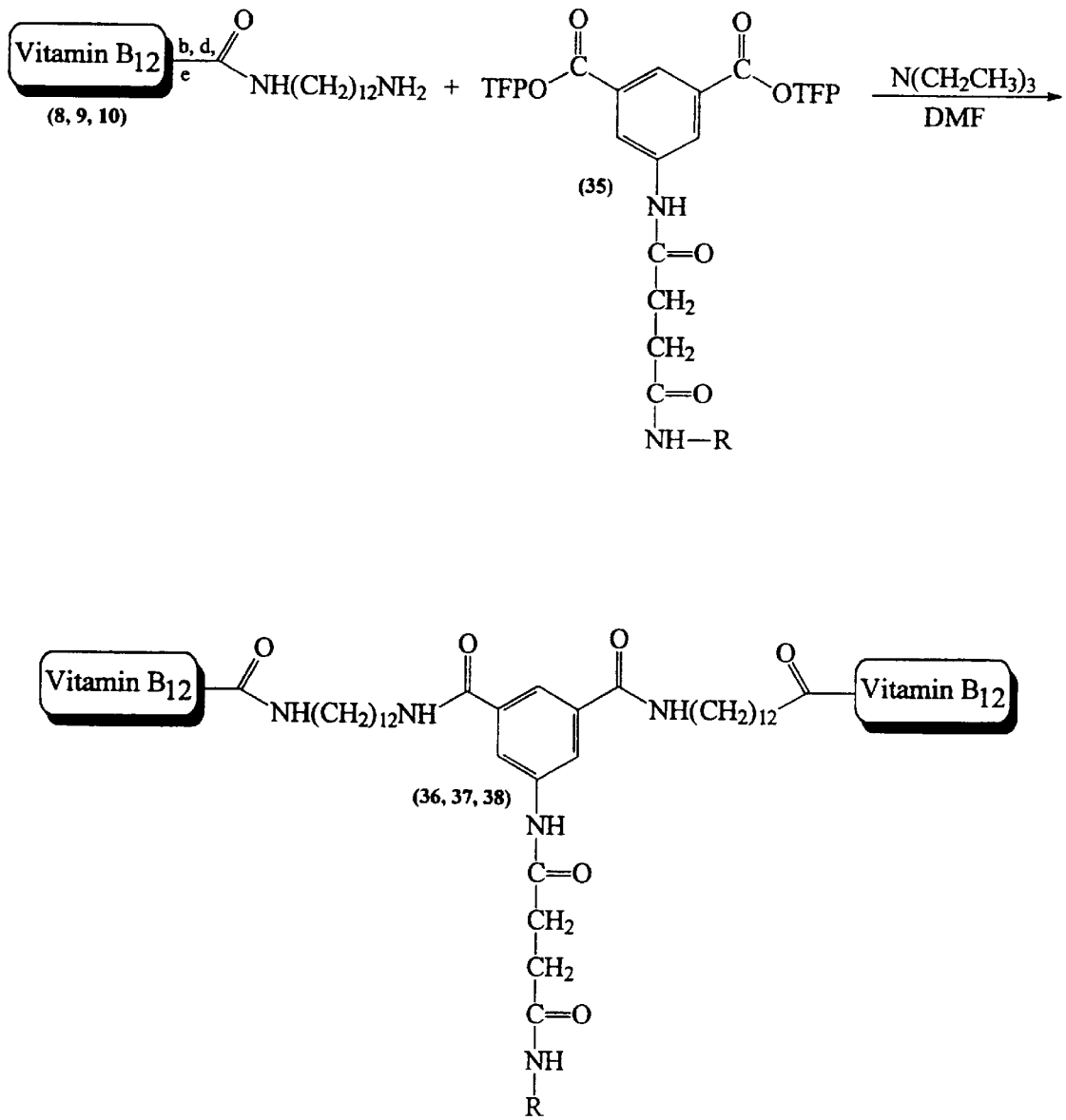
FIG. 16 is a schematic depicting a representative reaction scheme for the synthesis of a vitamin $B_{12}$ dimer using a homobifunctional or homotrifunctional cross-linking reagent.
Figure 17A:
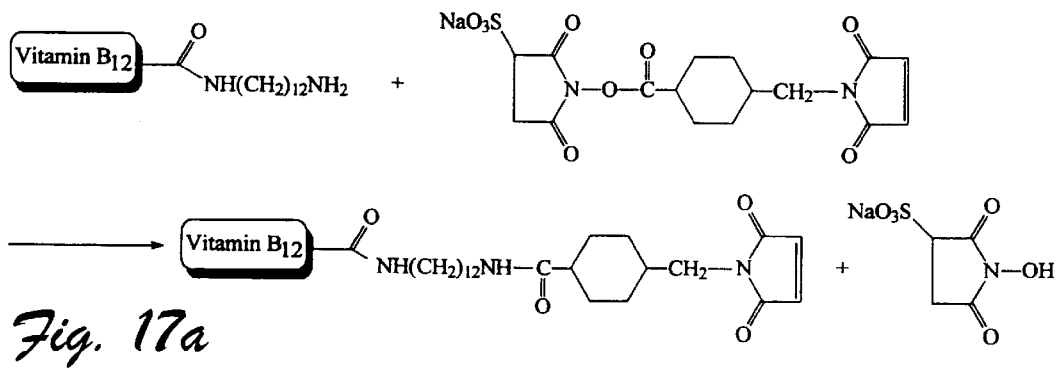
FIGS. 17A, 17B, and 17C are schematics depicting representative reaction schemes for the synthesis of a vitamin $B_{12}$ dimer using a heterobifunctional cross-linker.
Figure 17B:
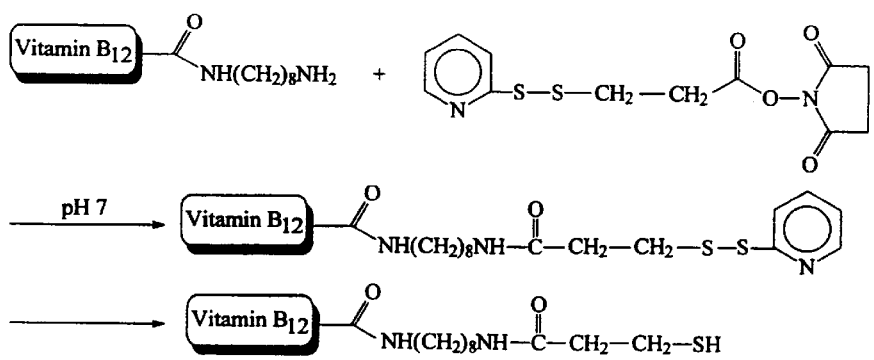
Figure 17C:
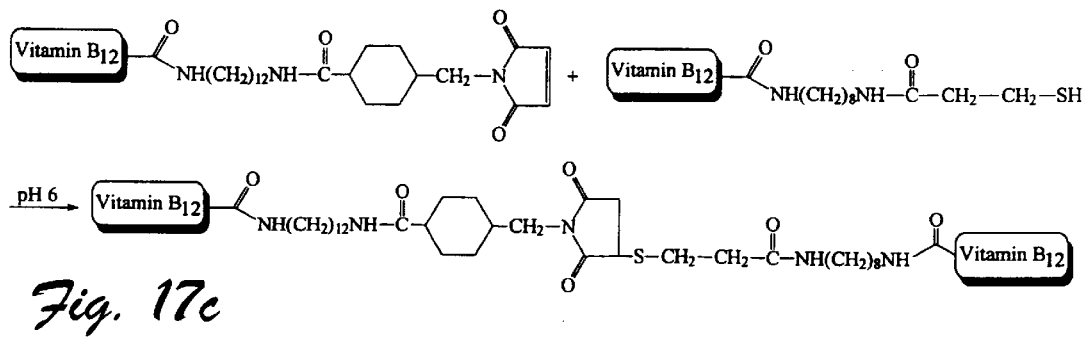
Figure 18:
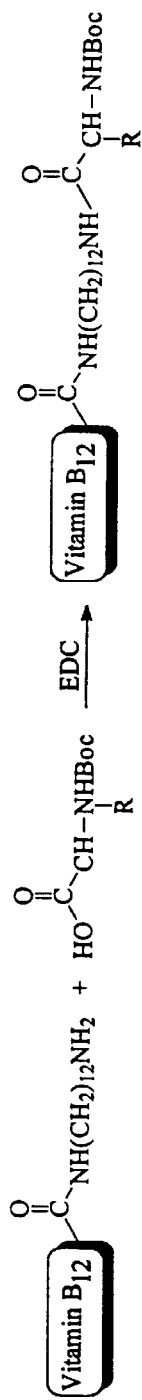
FIGS. 18–21 are schematics depicting representative reaction schemes for the synthesis of various receptor modulating agents generally comprised of a rerouting moiety, designated by the reactive group and R, selected from those represented in FIGS. 2–7, and a vitamin $B_{12}$ molecule or derivative thereof as a targeting moiety.
Figure 19:
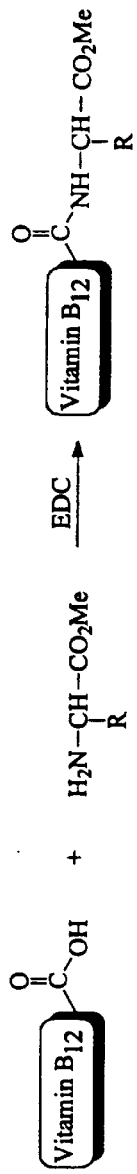
Figure 20:
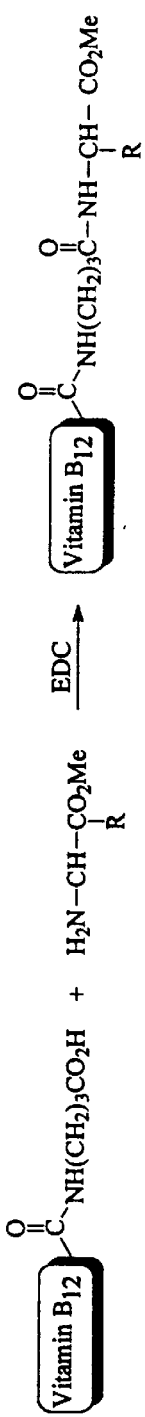
Figure 21:
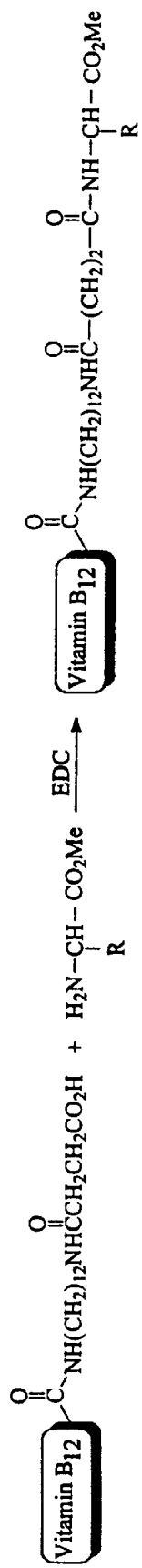

Cyanocobalamin Monocarboxylic Acid Diaminododecane Conjugate Dimer: ETAC Cross-linking This example serves to illustrate synthesis of a bivalent receptor modulating agent using a heterotrifunctional crosslinker. The reaction scheme for this synthesis is depicted in FIG. 15. The heterotrifunctional cross-linker is formed an ETAC reagent (*Bioconjugate Chem.* 1:36–50, 1990; *Bioconjugate Chem.* 1:51–59, 1990; *J. Am. Chem. Soc.* 101:3097–3110, 1979). Bivalency, in addition to enhancing affinity of binding, also imparts the ability to cross-ink neighboring receptors and trigger endocytosis. The bivalent "arms" of the agent may be lengthened with peptide or other linking molecules to enable simultaneous binding of both "arms". In the case of vitamin $B_{12}$ this may be assessed by gel filtration. If the linkers allow simultaneous interaction, there will be 2 moles of TcII for every mole of ETAC dimer present in a single peak of 80,000 m.w. (versus 40,000 m.w. of monomeric TcII). Simultaneous binding of 2 moles of TcII will then have the potential for bivalent binding to cell surface receptor. This can be tested by comparing the affinity of monomer and dimer binding to receptor. While the bivalent agent can be synthesized to include any rerouting moiety of this invention which enhances lysosomal targeting and retention, the compound tyramine, useful for radiolabeling is disclosed for the purpose of illustration.

Referring to FIG. 15, carboxy-ETAC (39) is prepared by the method of Liberatore et al. (*Bioconjugate Chem.* 1:1990). The carboxy-ETAC is converted to its acid chloride by reaction in thionyl chloride. Addition of amine (40) gives the amine-ETAC adduct (41). Reaction of amine-ETAC (1 mmol) in $CH_3CN$ with 1 M aqueous cysteamine (10 mmol) is conducted by stirring at room temperature for 24 h. This compound is reduced with $NaCNBH_3$ under acidic conditions. The crude amine-ETAC-cysteamine adduct (42) is purified by reverse-phase LC, using conditions noted above. A vitamin $B_{12}$ monocarboxylate (2, 3, 4) is conjugated with tyramine-ETAC-cysteamine compound by reaction with EDC in $H_2O$. The resultant vitamin $B_{12}$-ETAC-tyramine dimer (43) is purified by reverse phase LC, using conditions described above.

Example 15

Cyanocobalamin Monocarboxylic Acid Diaminododecane Conjugate Dimer: Isophthlate Cross-linking With Biotin Moiety This example illustrates the synthesis of a bivalent receptor modulating agent which is additionally coupled to a biotin moiety (44). Further modification can be obtained by coupling of this molecule with an avidin or streptavidin moiety.

Reaction Step A: Biotin (12.3 mmol, 3 g) was dissolved in warm (bath temperature 70° C.) DMF (60 mL) under argon atmosphere. It was then cool to ambient temperature and DCC (13.5 mmol, 2.79 g) was added, followed by tetrafluorophenol (24.6 mmol, 4.08 g). The reaction mixture was then cooled to 0° C. and stirred for 0.5 h. It was then brought back to ambient temperature and stirred for another 4–5 h. The reaction mixture was filtered and the filtrate was evaporated to dryness. The precipitate was washed with acetonitrile (50 mL) and was filtered to yield 5 g (98%) of white solid (45).

$^1H$ NMR (DMSO, δ): 1.4 (m, 2H); 1.7 (m, 2H); 2.5 (t, 2H); 2.8 (t, 2H); 3.1 (m, 1H); 4.1 (m, 1H); 4.3 (m, 1H); 6.4 (d, 2H); 7.9 (m, 1H).

Reaction Step B: 6-Aminocaproic acid (46) (7.5 mmol, 0.99 g) was dissolved in $H_2O$ (75 mL). Triethylamine (0.5 mL) was added followed by a solution of TFP ester of Biotin (5 mmol, 1.96 g) in warm acetonitrile (300 mL). The reaction was stirred overnight at room temperature. It was then filtered, washed with $H_2O$ (50 mL) and dried on high vacuum. Yield: 0.870 g (47%). The filtrate was evaporated to dryness. The residue was taken in boiling acetonitrile (75 mL) and was filtered, washed with hot acetonitrile. The solid (47) was dried on high vacuum to give 0.6 g, for a total yield of 1.47 g (79%).

$^1H$ NMR (DMSO-$d_6$, δ): 1.2–1.6 (m, 8H); 2.0 (t, 2H); 2.2 (t, 2H); 2.5 (dd, 2H); 2.8 (dd, 2H); 3.1 (m, 3H); 4.1 (m, 1H); 4.3 (m, 1H); 6.4 (d, 2H); 7.7 (m, 1H).

Reaction Step C: Biotin conjugated caproic acid (47) (2.68 mmol, 1 g) was dissolved in DMSO (50 mL). Triethylamine (0.4 mL) was added followed by TFP acetate (4.02 mmol, 1.05 g). The reaction mixture was then stirred at room temperature for 15–20 min (HPLC monitored). It was then evaporated to dryness. The residue was washed with ether and dichloromethane and dried on high vacuum (48). Yield: 1.24 g (89%).

$^1H$ NMR (DMSO-$d_6$, δ): 1.2 (t, 2H); 1.3–1.7 (m, 5H); 2.1 (t, 2H); 2.6 (dd, 2H); 2.8 (m, 4H); 3.1 (m, 4H); 4.2 (m, 1H); 4.4 (m, 1H); 6.4 (d, 2H); 7.8 (t, 1H); 8.0 (m, 1H).

Reaction Step D: TFP ester of Biotin-caproic acid (48) (0.67 mmol, 0.35 g) was dissolved in DMF (40 mL). Triethylamine (80 μL) was added followed by aminoisophthalic acid (1.005 mmol, 0.182 g). The reaction was stirred at room temp. for 8 days (HPLC monitored) while adding triethylamine (80 μL) every after 24 h. It was then evaporated to dryness. The residue was then applied to a column of silica and was initially eluted with acetonitrile (450 mL). It was then eluted with methanol, 20 mL of fractions were collected, at the fraction 2 the solvent was changed to DMF. The fractions containing the final product (HPLC monitored) were evaporated to dryness (49) to yield 230 mg (65%).

$^1H$ NMR (DMSO-$d_6$, δ): 1.3–1.7 (m, 8H); 2.1 (t, 2H); 2.3 (t, 2H); 2.6 (m, 2H); 2.8 (m, 2H); 3.1 (m, 3H); 4.1 (m, 1H); 4.3 (m, 1H); 6.4 (d, 2H); 7.8 (t, 1H); 8.1 (m, 1H); 8.46 (s, 2H)

Reaction Step E: Biotin-caproic acid-isophthalic acid (49) (0.376 mmol, 200 mg) was dissolved in DMF (30 mL) under argon atmosphere. TFP acetate (0.94 mmol, 241 mg) was added by double ended needle, followed by triethylamine (112 μL). The reaction was then stirred at room temp. for 24 h (HPLC monitored). It was then evaporated to dryness. The light brownish oil was taken in ether, solid was filtered and was washed with ether (50 mL) (50) to yield 250 mg (86%).

$^1H$ NMR (DMSO-$d_6$, δ): 1.3–1.7 (m, 8H); 2.1 (t, 2H); 2.3 (t, 2H); 2.6 (m, 2H); 2.8 (m, 2H); 3.1 (m, 3H); 4.2 (m, 1H); 4.4 (m, 1H); 6.4 (d, 2H); 7.8 (t, 1H); 8.1 (m, 2H); 8.57 (s, 1H); 8.9 (s, 2H).

Reaction Step F: In a solution of cyanocobalamin carboxylic acid-diaminododecane conjugate (8, 9, 10) (0.130 mmol, 0.2 g) in a mixture of DMF: $H_2O$ (3:1) (40 mL) triethylamine (12 μL) was added. DiTFP ester of biotin-caproic acid-isophthalic acid (50) (0.065 mmol, 0.050 g) was added over a period of 5–10 min. The reaction mixture was stirred at room temperature for 3 h (HPLC monitored). It was then evaporated to dryness. The residue was digested with 100 mL of acetone and the solvent was decanted to yield 230 mg (62%) (51). mp 195–198° C. with decomposition.

Example 16

Cyanocobalamin Monocarboxylic Acid Diaminododecane Conjugate Dimer: Isophthalate Cross-linking With Para-iodobenzoyl Moiety This is an example of a bivalent receptor modulating agent which is also conjugated to a para-iodobenzoyl moiety.

Reaction Step A: A 5 g (28 mmol) quantity of 5-aminoisophthalic acid (52) was dissolved in 30 mL 1N NaOH and placed in an ice/water bath. To the cold solution was added 7.5 g (28 mmol) 4-iodobenzoyl chloride (52) in 60 mL of acetonitrile, dropwise. The thick white precipitate was then stirred for 10 minutes before removing the ice/water bath and allowing the mixture to stir an additional 10 minutes. The reaction mixture was adjusted to pH 4 with acetic acid and the resulting solid collected. This solid was then dissolved in 30 mL 1N NaOH and washed with ether (2×50 mL). The resulting aqueous solution was filtered and acidified to pH 4 with acetic acid. The white precipitate was the collected and dried on high vacuum to yield 0.6 g (99+%) of (54). mp >300° C.; IR (Nujol, cm$^{-1}$) 3570(m), 3300(m), 1645, 1580(m), 1525(m), 760(m); $^1$H NMR (DMSO-d$_6$, δ), 8.51 (2H, d, J=0.7 Hz), 8.27 (1H, s), 7.94 (2H, d, J=4.2 Hz), 7.84 (2H, d, J=4.1 Hz).

Reaction Step B: A 5 g (12.2 mmol) quantity of 5-[N-iodobenzoyl)amino]-isophthalic acid (54) was suspended in 100 mL anhydrous ethyl acetate. To this was added $_{12}$.5 g (73 mmol) 2,3,5,6-tetrafluorophenol (55) followed by 5 g (24.2 mmol) 1,3-dicyclohexylcarbodiimide. This suspension was then stirred at room temperature for 3 days before filtering off the solid and washing with an additional 20 mL of ethyl acetate. The filtrate was then evaporated to dryness. The resulting sticky white solid was suspended in 50 mL acetonitrile and stirred for 30 minutes. Filtering yielded 3.75 g of white solid (43%) (56). mp 250–251° C.; IR (Nujol, cm-1) 3220(m), 3060(m), 1750, 1655, 1520, 1485, 1330, 1195, 1110, 1085, 955(m), 945(m); $^1$H NMR (DMSO-d$_6$, δ), 9.06 (2H, d, J=0.7 Hz), 8.57 (1H, t, J=1.4 Hz), 8.04 (2H, m), 7.94 (2H, d, J=4.2 Hz), 7.81 (2H, d, J=4.3 Hz).

Reaction Step C: To a solution of cyanocobalamin carboxylic acid-diaminododecane conjugate (56) (0.192 mmol, 0.3 g) in a mixture of DMF: H$_2$O (3:1) (40 mL) was added triethylamine (0.018 mL). To this solution, DiTFP ester of 5-[N(p-Iodobenzoyl)amino]-Isophthalic acid (57)(0.096 mmol, 0.068 g) was added over a period of 5–10 min. The reaction mixture was stirred at room temperature for 4–5 h (HPLC monitored). It was then evaporated to dryness. The solid residue was dissolved in 20 mL of methanol: H$_2$O (8:2) and applied to a reverse phase C-18 column (500 mm×25 mm, Alltech, 150 psi) which was developed with the same solvent. RAININ Rabbit-plus peristaltic pumping system was used with a DYNAMAX (model LW-1) UV visible absorbance detector; the elute was collected with an automatic fraction collector. The fractions containing the final product (BPLC monitored) were evaporated to dryness.

b-acid dimer (58): yield: 280 mg (76%), mp 230–233° C. with decomposition, $^1$H NMR (D$_2$O, δ) 0.43 (s, 6H, C-20 CH$_3$); 1.19 (s, 8H); 1.3 (m, 36H); 1.37 (d, 2H); 1.46 (s, 10H); 1.63 (m, 8H); 1.87 (s, 12H); 2.05 (m, 10H); 2.27 (d, 16H, B10 & B11 CH$_3$); 2.35 (m, 8H); 2.6 (d, 18H); 2.8 (s, 8H); 3.0 (s, 10H); 3.15 (m, 8H); 3.3 (d, 8H); 3.37 (m, 14H); 3.6 (m, 2H); 3.68 (d, 2H); 3.76 (m, 2H); 3.9 (d, 2H); 4.07 (m, 2H); 4.$_{12}$ (m, 2H); 4.18 (m, 2H); 4.3 (m, 2H); 4.5 (m, 2H); 4.64 (m, 4H); 6.0 (s, 2H, 2C-10); 6.26 (d, 2H, 2R$_1$); 6.6 (s, 2H, 2B4); 7.1 (s, 2H, 2B2); 7.25 (s, 2H, 2B7); 7.7 (d, 2H); 7.9 (d, 2H); 7.99 (d, 1H); 8.28 (s, 2H); MS (FAB$^+$): m/e 3453. IR (KBr): 3400, 3200, 2950, 2060, 1660, 1570, 1490, 1060 cm$^{-1}$. UV (MeOH): λ360.6 (ε48 871)

e-acid dimer (59): yield: 258 mg (70%), mp 285–290° C. with decomposition, $^1$H NMR (D$_2$O, δ) 0.43 (s, 6H, C-20 CH$_3$); 1.17 (s, 8H); 1.22 (d, 13H); 1.29 (s, 45H); 1.36 (d, 22H); 1.44 (s, 10H); 1.6 (m, 8H); 1.86 (s, 12H); 2.04 (m, 10H); 2.25 (s, $_{12}$H, B10 & B11 CH$_3$); 2.36 (m, 8H); 2.55 (d, 20H); 2.83 (m, 8H); 3.15 (m, 8H); 3.29 (s, 10H); 3.36 (m, 8H); 3.58 (m, 2H); 3.65 (m, 2H); 3.75 (m, 2H); 3.9 (d, 2H); 4.06 (m, 2H); 4.12 (m, 2H); 4.16 (m, 2H); 4.3 (m, 2H); 4.5 (m, 2H); 4.57 (s, 2H); 4.65 (m, 2H); 6.0 (s, 2H, 2C-10); 6.26 (d, 2H, 2R1); 6.5 (s, 2H, 2B4); 7.1 (s, 2H, 2B2); 7.25 (s, 2H, 2B7); 7.7 (d, 2H); 7.89 (d, 2H); 7.98 (s, 1H); 8.26 (s, 2H); MS (FAB$^+$): m/e 3453. IR (KBr): 3400, 3200, 2950, 2060, 1660, 1570, 1490, 1060 cm$^{-1}$; UV (MeOH): λ360 (ε41 481).

d-acid dimer (60): yield 265 mg (72%), mp 253–255° C. with decomposition, $^1$H NMR (D$_2$, δ) 0.43 (s, 6H, C-20 CH$_3$); 1.16 (s, 8H); 1.22 (d, 12H); 1.33 (m, 36H); 1.43 (s, 10H); 1.53 (m, 6H); 1.6 (m, 8H); 1.86 (s, 12H); 2.03 (m, 8H); 2.25 (d, $_{12}$H, B10 & B10 CH$_3$); 2.33 (m, 8H); 2.54 (d, 20H); 2.8 (s, 4H); 3.0 (s, 4H); 3.28 (s, 10H); 3.35 (m, 8H); 3.58 (m, 2H); 3.65 (m, 2H); 3.73 (m, 2H); 3.88 (d, 2H); 4.05 (m, 2H); 4.1 (m, 2H); 4.17 (m, 2H); 4.3 (m, 2H); 4.5 (m, 2H); 4.57 (s, 2H); 4.63 (m, 2H); 6.0 (s, 2H, 2C-10); 6.26 (d, 2H, 2R$_1$); 6.5 (s, 2H, 2B4); 7.1 (s, 2H, 2B2); 7.25 (s, 2H, 2B7); 7.7 (d, 2H); 7.89 (d, 2H); 7.98 (s, 1H); 8.26 (s, 2H); MS (FAB$^+$): m/e 3453. IR (KBr): 3400, 3200, 2950, 2060, 1660, 1570, 1490, 1060 cm$^{-1}$; UV (MeOH): λ360 (ε48 245).

Example 17

Cyanocobalamin Monocarboxylic Acid Diaminododecane Conjugate Dimer: Isophtahate Cross-linking With Para-(tri-butylstannyl)benzoyl Moiety This is an example of a bivalent receptor modulating agent coupled to a para-tri-N-butyl stannyl moiety.

Reaction Step A: A 2 g (2.8 mmol) quantity of the diTFP ester of 5-[N-(p-Iodobenzoyl)amino]-Isophthalic acid (57) (as prepared above) was dissolved in 20 mL dry toluene under argon. To this was added 2.8 mL (5.5 mmol) of bis(tributyltin) (61) followed by 40 mg (0.04 mmol) tetrakis (triphenylphosphine)palladium (62). The mixture was stirred at room temperature for 15 minutes before heating to 80° C. for 2 h. Since the mixture only darkened slightly over the 2 h period, an additional 40 mg of palladium catalyst was added. Within 1 hour the mixture had turned black. After cooling to room temperature, the toluene was removed by rotary evaporation. The resulting black oil (containing solids), was then taken into 20 mL ethyl acetate and dried onto 10 g silica gel (via rotoevaporation). This solid was then added to a 250 g (40×3.5 cm) silica gel column and eluted initially with hexanes containing 5% acetic acid. After 600 mL, the solvent was changed to 90/10 hexanes/ethyl acetate (containing 5% acetic acid). Fractions 14–16 were combined and dried to yield 1.5 g (62%) of white solid (62). mp 120–123° C.;

$^1$H NMR (CDCl$_3$, δ), 8.87 (2H, d, J=0.7 Hz), 8.76 (1H, t, J=1.6 Hz), 8.38 (1H s), 7.84 (2H d, J=4.1 Hz), 7.62 (2H, d, J=4.1 Hz), 7.07 (2H, m), 1.55 (6H, m), 1.36 (15H, m), 1.11 (6H, m), 0.89 (9H, t, J=7.3 Hz); MS (FAB$^+$) M+H patterns calculated 870 (75.1%), 871 (52.9%), 872 (100%), 873 (41.0%), 874 (21.4%), found 870 (82.1%), 871 (55.1%), 872 (100%), 873 (42.1%), 874 (25.2%).

IR (Nujol, cm$^{-1}$) 1750, 1645, 1520, 1480(m), 1185, 1100, 1085.

Reaction Step B: In a solution of cyanocobalamin carboxylic acid-diaminododecane conjugate (8, 9, 10) (0.065 mmol, 0.1 g) in a mixture of DMF: H$_2$O (3:1) (40 mL) triethylamine (0.006 mL) was added. DiTFP ester of 5-[N-(p-tributyltin benzoyl)amino]-Isophthalic acid (63)(0.0325 mmol, 0.028 g) was added over a period of 5–10 min. The reaction mixture was stirred at room temperature for 12–14 h (HPLC monitored). It was then evaporated to dryness. The residue was digested with 100 mL of acetone and the solvent was decanted.

b-acid dimer (64): yield: 90 mg (70%), mp 208–212° C. with decomposition, $^1$H NMR(D$_2$O, δ) 0.43 (s, 6H, C-20 CH$_3$); 0.88 (t, 9H); 1.15 (t, 12H); 1.19 (s, 8H); 1.3 (m, 36H); 1.37 (d, 12H); 1.46 (s, 10H); 1.6 (m, 8H); 1.9 (s, 12H); 2.05 (m, 10H; 2.28 (d, 16H, B10 & B11 CH$_3$); 2.35 (m, 8H); 2.6 (d, 18H); 2.8–2.9 (m, 16H); 3.15 (m, 8H); 3.3 (s, 8H); 3.37 (m, 14H); 3.6 (m, 4H); 3.76 (in 2H); 3.9 (d, 2H); 4.07 (in 2H); 4.12 (mn 2H); 4.18 (m, 2H); 4.3 (mn 2H); 4.5 (m, 2H); 4.68 (m, 2H); 6.0 (s, 2H, 2C-10); 6.26 (d, 2H, 2R$_1$); 6.6 (s, 2H, 2B4); 7.1 (s, 2H, 2B2); 7.25 (d, 2H, 2B7); 7.6 (d, 2H); 7.9 (d, 2H); 7.99 (br s, 1H); 8.28 (br s, 2H); IR (KBr): 3400, 3200, 2950, 2060, 1660, 1570, 1490, 1060 cm$^{-1}$.

e-acid dimer (65): yield: 93 mg (72%), mp >300° C., $^1$H NMR (D$_2$O, δ) 0.43 (s, 6H, C-20 CH$_3$); 0.88 (t, 9H); 1.12 (t, 12H); 1.17 (d, 8H); 1.22 (d, 13H); 1.29 (s, 45H; 1.36 (d, 22H); 1.44 (s, 10H); 1.6 (m, 8H); 1.87 (d, 12H); 2.04 (m, 10H); 2.25 (s, 12H, B10 & B11 CH$_3$); 2.36 (m, 8H); 2.55 (d, 20H); 2.8 (m, 8H); 3.15 (m, 8H); 3.29 (s, 10H); 3.36 (m, 14H); 3.6 (m, 4H); 3.73 (m, 2H); 3.9 (d, 2H); 4.07 (m, 2H); 4.12 (m, 2H); 4.16 (m, 2H); 4.3 (m, 2H); 4.5 (m, 2H); 4.66 (m, 2H); 6.0 (s, 2H, 2C-10); 6.26 (d, 2H, 2R1); 6.6 (s, 2H, 2B4); 7.1 (s, 2H, 2B2); 7.25 (s, 2H, 2B7); 7.6 (d, 2H); 7.9 (d, 2H); 7.98 (br s, 1H); 8.28 (br s, 2H); IR (KBr): 3400, 3200, 2950, 2060, 1660, 1570, 1490, 1060 cm$^{-1}$.

d-acid dimer (66): yield: 100 mg (78%), mp 202–205° C. with decomposition, 1H NMR (D$_2$O, δ) 0.43 (s, 6H, C-20 CH$_3$); 0.88 (t, 9H); 1.12 (t, 12H); 1.15 (s, 8H); 1.29 (m, 36H); 1.35 (d, 12H); 1.44 (s, 10H); 1.53 (m, 6H); 1.6 (m, 8H); 1.86 (d, 12H); 2.03 (m, 8H; 2.25 (d, 12H, B10 & B11 CH$_3$); 2.33 (m, 8H); 2.54 (d, 20H); 2.8 (m, 8H); 3.13 (m, 8H); 3.28 (s, 10H); 3.35 (m, 10H); 3.6 (m, 4H); 3.73 (m, 2H); 3.9 (d, 2H); 4.05 (m, 2H); 4.1 (m, 2H); 4.17 (m, 2H); 4.3 (m, 2H); 4.5 (m, 2H); 4.6 (m, 2H); 6.0 (s, 2H 2C-10); 6.26 (d, 2H, 2H); 6.6 (s, 2H, 2B4); 7.1 (s, 2H, 2B2); 7.25 (s, 2H, 2B7); 7.6 (d, 2H); 7.9 (d, 2H); 7.98 (br s, 1H); 8.28 (br s, 2H); IR (KBr): 3400, 3200, 2950, 2060, 1660, 1570, 1490, 1060 cm$^{-1}$.

Example 18

Evaluation of the Ability of Vitamin B$_{12}$ Receptor Modulating Agents to Bind to TcII This example serves to demonstrate a competitive binding assay suitable for evaluating the ability of vitamin B$_{12}$ receptor modulating agents to bind TcII. Binding of the vitamin B$_{12}$ derivatives to recombinant transcobalamin II was conducted in picomolar concentrations and the percent bound ascertained.

In this competitive binding assay, various B$_{12}$ derivatives, including vitamin B$_{12}$ receptor modulating agents, were evaluated for their ability to bind to TcII relative to radiolabeled B$_{12}$. Varying concentrations of each derivative were incubated with immobilized TcII in the presence of a constant amount of radiolabeled B$_{12}$ After incubation for 20 minutes at 37° C., the free radiolabeled B$_{12}$ was separated from the TcII bound tracer by removal of the supernatant. The radioactivity of the supernatant solution was then measured to determine the amount of free radiolabeled B$_{12}$ present at the end of each competition. By measuring the amount of free radiolabeled B$_{12}$ for each competition, the ability of each derivative to inhibit radiolabeled B$_{12}$ binding was determined. A binding curve was then be constructed for each B$_{12}$ derivative where the amount of radiolabeled B$_{12}$ bound (% radiolabel bound) was correlated with the concentration of derivative present in the original mixture. The more effective the derivative is in binding to TcII, the lower the percent bound radiolabeled vitamin B$_{12}$.

Figure 22:
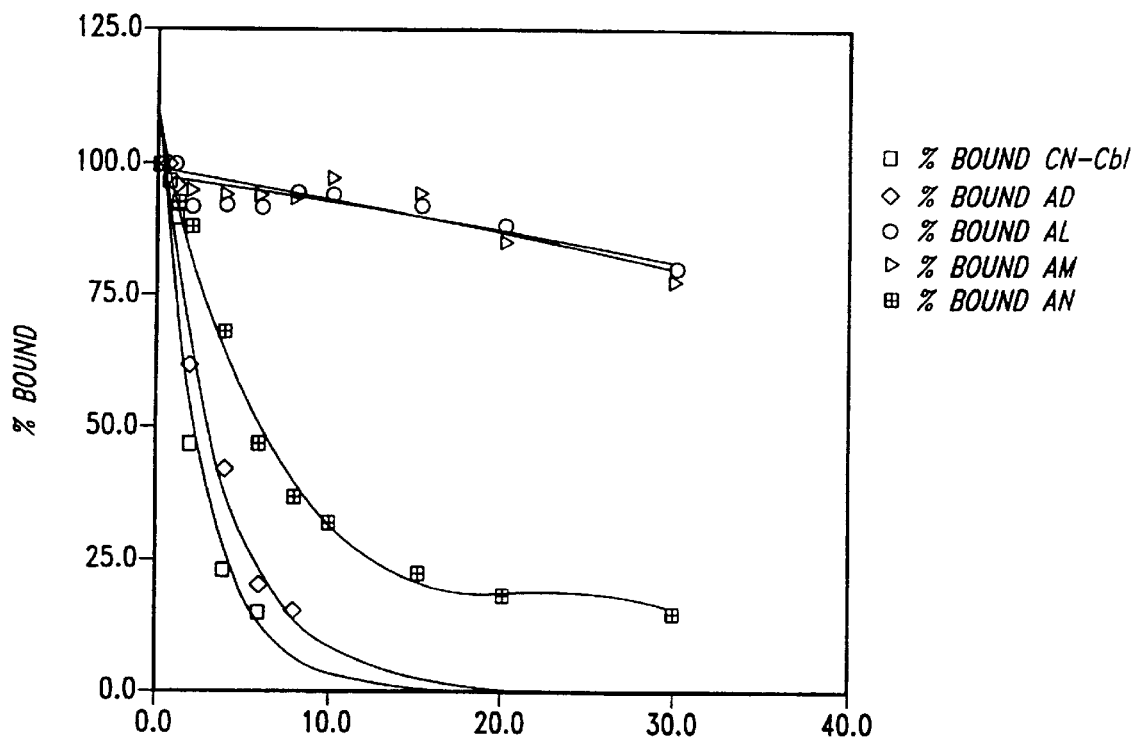
FIG. 22 is a graph illustrating the binding curve of Transcobalamin II to the cyanocobalamin monocarboxylic acids produced in Example 1. AD=Cyanocobalamin (1); AL=Cyanocobalamin b-monocarboxylic acid (2); AM=Cyanocobalamin e-monocarboxylic acid (3); and AN=Cyanocobalamin d-monocarboxylic acid (4).

FIG. 22 illustrates the binding curve of Transcobalamin II to the cyanocobalamin monocarboxylic acids produced in Example 1. AD=Cyanocobalamin (1); AL=Cyanocobalamin b-monocarboxylic acid (2); AM=Cyanocobalamin e-monocarboxylic acid (3); and AN=Cyanocobalamin d-monocarboxylic acid (4). The d-carboxylate (3) appears to bind nearly as well as cyanocobalamin. Two samples of vitamin B$_{12}$ were used, one as a known standard and the other as an unknown.

Figure 23:
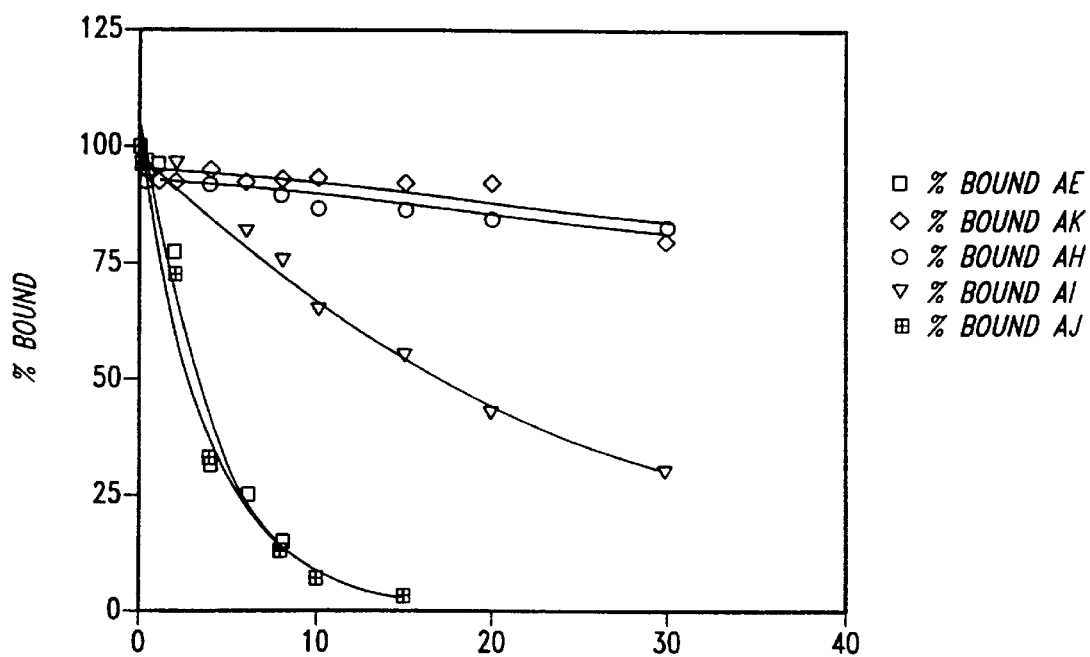
FIG. 23 is a graph illustrating the binding curve of Transcobalamin II to the cyanocobalamin diaminododecane adducts produced in Example 3 and 4. AH=Cyanocobalamin b-monocarboxylic acid conjugate diaminododecane (7); AI=Cyanocobalamin e-monocarboxylic acid conjugate diaminododecane (8); AJ=Cyanocobalamin d-monocarboxylic acid conjugate diaminododecane (9); AK=Cobalamin e-monocarboxylic acid conjugate diaminododecane, and AE=Cyanocobalamin ribose-succinate (11).

FIG. 23 illustrates the binding curve of Transcobalamin II to the cyanocobalamin diaminododecane adducts (8, 9, 10) and succinate adduct (13) produced in Example 3 and 4 above. AH=Cyanocobalamin b-monocarboxylic acid conj Diaminododecane (7); AI=Cyanocobalamin e-monocarboxylic acid conj Diaminododecane (8); AJ=Cyanocobalamin d-monocarboxylic acid conj Diaminododecane (9); AK=Cobalamin e-monocarboxylic acid conj Diaminododecane, and AE=Cyanocobalamin Ribose-Succinate (11). The b-conjugate (17) has the least binding, whereas the e-conjugate (18) has intermediate binding, and the d-conjugate (19) binds quite well. The biotin conjugate attached to the ribose site (13) appears to bind very well, as does its precursor amino derivative (12). The additional compound studied is of unknown structure, but may have the amine group coordinated with the cobalt atom as the mass spectrum indicates that it has the appropriate mass for (7) minus HCN. It is clear that this unknown compound is not likely to bind TcII.

Figure 24:
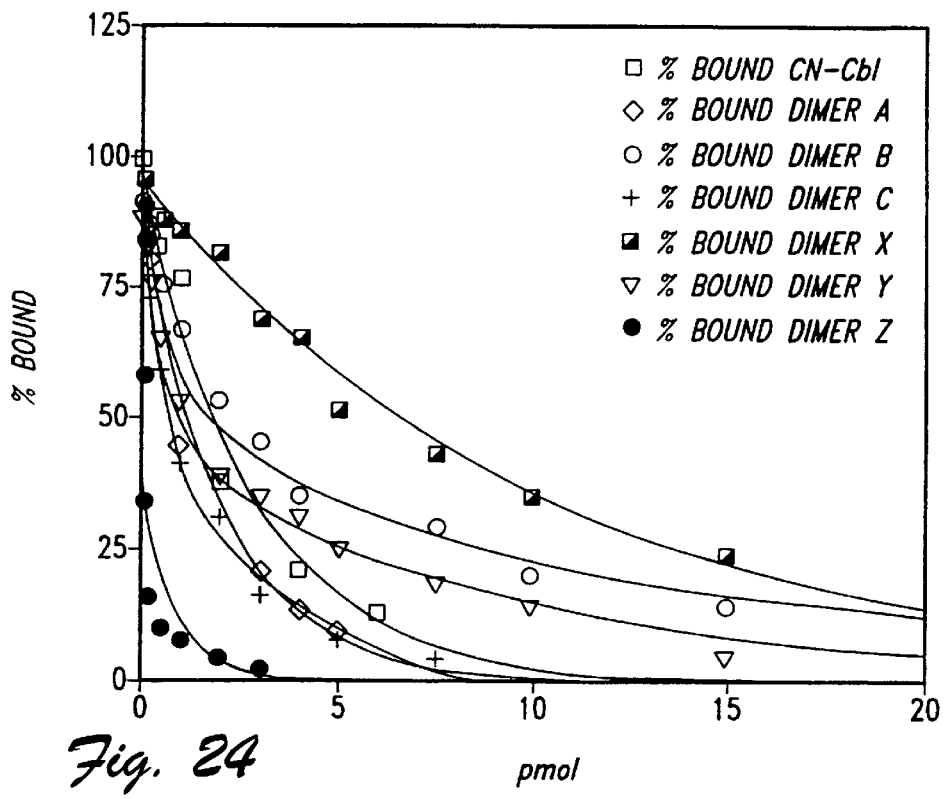
FIG. 24 is a graph illustrating the binding curve of Transcobalamin II to a series of vitamin $B_{12}$ dimers. Dimer X=b-acid dimer with isophthaloyl dichloride (36); Dimer Y=e-acid dimer with isophthaloyl dichloride (37); dimer Z=d-acid dimer with isophthaloyl dichloride (38); Dimer A=b-acid Dimer with p-iodo benzoyl isophthaloyl dichloride (58); Dimer B=e-acid Dimer with p-iodo benzoyl isophthaloyl dichloride (59); and Dimer C=d-acid Dimer with p-iodo benzoyl isophthaloyl dichloride (60). These dimers were prepared as set forth in the Examples below. (see Examples 13 and 16.)

FIG. 24 illustrates the binding curve of Transcobalamin II to a series of vitamin B$_{12}$ dimers. Dimer X=b-acid dimer with Isophthaloyl dichloride (36); Dimer Y=e-acid dimer with Isophthaloyl dichloride (37); dimer Z=d-acid dimer with Isophthaloyl dichloride (38); Dimer A=b-acid Dimer with p-Iodo benzoyl Isophthaloyl dichloride (58); Dimer B=e-acid Dimer with p-Iodo benzoyl Isophthaloyl dichloride (59); and Dimer C=d-acid Dimer with p-Iodo benzoyl Isophthaloyl dichloride (60).

Figure 25:
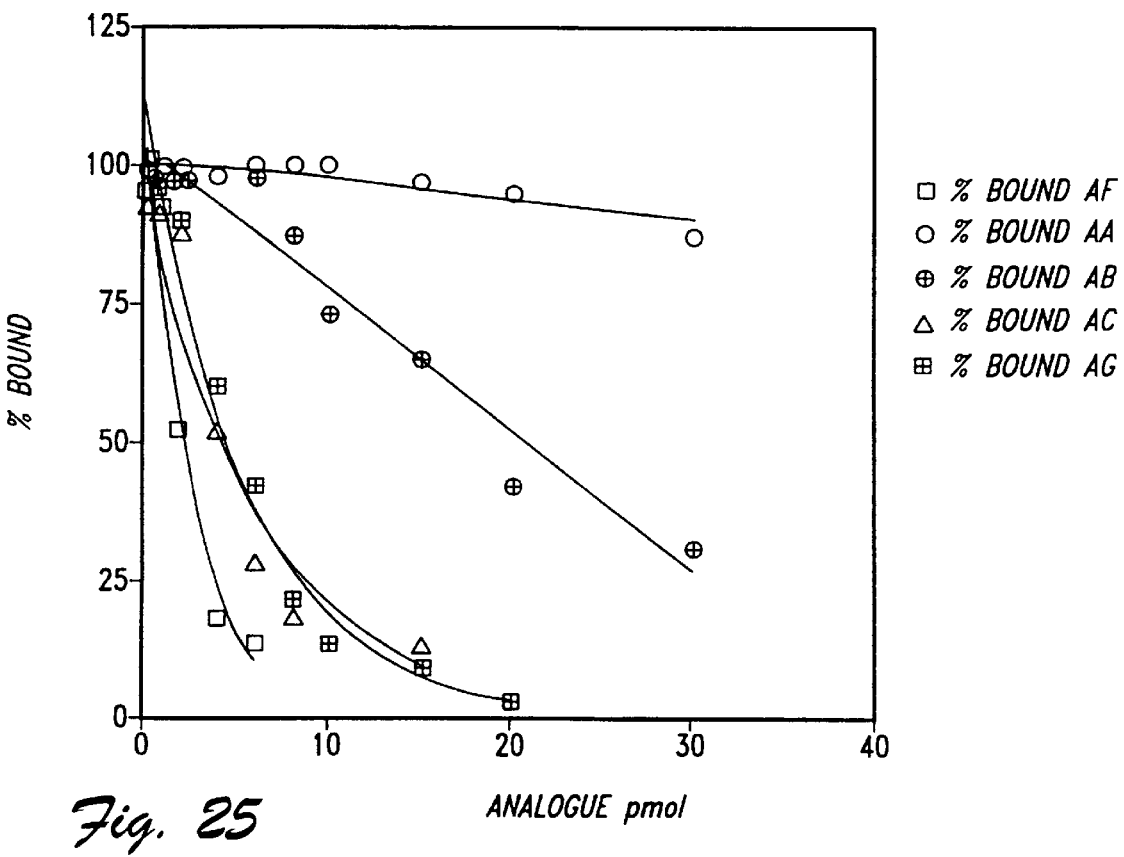
FIG. 25 is a graph illustrating the binding curve of Transcobalamin II to a series of biotinylated vitamin $B_{12}$ molecules. AA Cyanocobalamin b-monocarboxylic acid conjugate diaminododecane and biotin (17); AB=Cyanocobalamin e-monocarboxylic acid conjugate diaminododecane and biotin (18); AC=Cyanocobalamin d-monocarboxylic acid conjugate diaminododecane and biotin (19); AF=Cyanocobalamin ribose-succinate conjugate diaminododecane (13); and AG=Cyanocobalamin ribose-succinate conjugate diaminododecane and biotin (20). These biotinylated molecules were prepared as set forth in Examples below. (see Example 8.)

FIG. 25 illustrates the binding curve of Transcobalamin II to a series of biotinylated vitamin B$_{12}$ molecules. AA=Cyanocobalamin b-monocarboxylic acid conj Diaminododecane and Biotin (17); AB=Cyanocobalamin e-monocarboxylic acid conj Diaminododecane and Biotin (18); AC=Cyanocobalamin d-monocarboxylic acid conj Diaminododecane and Biotin (19); AF=Cyanocobalamin Ribose-Succinate conj Diaminododecane (13); and AG=Cyanocobalamin Ribose-Succinate conj. Diaminododecane and Biotin (20).

Example 19

Assay For Biological Active of Vitamin B$_{12}$ Receptor Modulating Agents

This example serves to demonstrate the use of an assay to ascertain biological activity of the receptor modulating agents of the present invention.

Receptor down-modulation involves a comparison of treatment of a target cell line such as K562, each sample is treated with vitamin B$_{12}$ or a vitamin B$_{12}$ receptor modulating agent at 4° C. for 24 hours. Following this period, cells of each sample are separated from a vitamin B$_{12}$ or a vitamin B$_{12}$ receptor modulating agent by centrifugation. The cells are then washed and resuspended in phosphate buffered saline containing 2 mM EDTA for a brief period of time not to exceed 15 minutes at 4° C. Then, the cells are washed again and returned to a tissue culture medium at 4° C. The tissue culture medium containing TcII and a radiolabeled TcII/$B_{12}$ complex. The time course of TcII/$B_{12}$ binding to the cell receptor is determined by measuring the percent radiolabel bound to the cell at 0, 15, 30, 60, 120, and 240 minutes. Those samples exposed to the vitamin $B_{12}$ receptor modulating agents of the present invention show significantly reduced TcII/$B_{12}$ complex binding compared to cells cultured in vitamin $B_{12}$. Trypsin treated cells reveal any nonspecific binding or uptake of the labeled vitamin $B_{12}$ on or within the cell.

Example 20

Method For Assessing Biological Activity of a Receptor Modulating Agent

This example serves to demonstrate a method suitable for assessing the biological activity of a receptor modulating agent of the present invention.

0.233 $10^6$ cells/ml K562 cells were cultured in RPMI medium modified by addition of 10 μM MeTHF, 2.7 nM vitamin $B_{12}$ and 1% human serum. No folate was added. 10 μM d-diamimododecane adduct (7) was added and cultured over 9 days at 37° C. 10 μM vitamin $B_{12}$ cultured under identical conditions as (7) was utilized as a control. The cultures were then independently assessed for proliferation and cell death by Trypan blue exclusion. The results are described in Table 10, below, in terms of the percent cell death.

TABLE 10

|  | Control | d-diaminododecane adduct (7) |
|---|---|---|
| Proliferation | 98% | 9% |
| Cell Death | 8% | 85% |

The receptor modulating agent, in this case d-diaminododecane adduct (7), clearly demonstrates the marked biological activity of the receptor modulating agent.

Example 21

Synthesis of an Anti-inflammatory Receptor Modulating Agent

The synthetic peptide f-met-leu-phe is equivalent to a bacterial cell wall constituent (*Biochem. Soc. Trans.* 19:1127–9, 1991; *Agents Actions Suppl.* 35:3–8, 1991; *Agents Actions Suppl.* 35:11–6, 1991; *J Immunol.* 146:975–80, 1991). This peptide is recognized by receptors on PMN which can respond by chemotaxis to sites of local inflammation along a gradient of the peptide. During inflammation, receptor expression can be dramatically increased by mobilizing receptor from intracellular pools. Non-specific methods used to abrogate this up-regulation also inhibit chemotaxis and presumably the anti-inflammatory reaction associated with local inflammation (*J. Immunol.* 145:2633–8, 1990). The synthesis of a receptor modulation agent useful as an inhibitor of early inflammation is described below.

The peptide f-met-leu-phe-(gly)$_3$4eu-O-Me is synthesized using tea-bag methodology or solid phase peptide synthesis procedures described by Merrifield et al. (*Biochemistry* 21:5020–31, 1982) and Houghten (*Proc. Nat'l. Acad. Sci. (USA)* 82:5131–35, 1985), or using a commercially available automated synthesizer, such as the Applied Biosystems 430 A peptide synthesizer. The peptide-amide is deprotected in 45% trifluoroacetic acid-51% methylene chloride-2% ethanedithiol-2% anisole for 20 minutes, and cleaved from the 4-methylbenzhydrylamine resin using the Tam-Merrifield low-high HF procedure (J. P. Tam et al., *J. Am. Chem. Soc.* 105:6442–55, 1983). The peptide is then extracted from the resin using 0.1 M ammonium acetate buffer, pH 8, and is lyophilized. The crude peptide is purified using reverse phase HPLC on a Vydac C-4 analytical column (The Separations Group, Hesperia, Calif.), and a linear gradient of 0.5–1.0%/min. from 100% acetonitrile+0.1%v/v trifluoroacetate to 100% acetonitrile+0.1% trifluoroacetate. The BPLC-purified peptide is analyzed by amino acid analysis (R L. Heinriksen and S. C. Meredith, *Anal. Biochem.* 160:65–74, 1984) after gas phase hydrolysis (N. M. Meltzer et al., *Anal. Biochem.* 160:356–61, 1987). The sequence of the purified peptide may be confirmed by Edman degradation on a commercially available sequencer (R. M. Hewick et al., *J. Biol. Chem.* 15:7990–8005, 1981). The peptide amide is converted to an O-methyl ester (i.e., f-met-leu-phe-(gly)$_3$-leu-O-Me) by treatment with dimethylformamide (5 g/60 mL with 1.3 equivalents of NaHCO$_3$ in excess methyl iodide (4 equivalents). The mixture is stirred under argon gas at room temperature for 40 hours. If required, the peptide is extracted to dryness with 150 mL of ethyl acetate. The receptor for modulating agent is used to treat PMN, activated with GM-CSF (to increase expression of fMLP receptors). Loss of binding of biotinylated fMLP is compared on fMLP versus f-MLP receptor modulating agent treated cells.

Example 22

Synthesis of a Fusion Protein Receptor Modulating Agent

An EGF receptor modulating agent containing a genetically engineered fusion protein is hereby described. Briefly, the C-terminus of a DNA sequence encoding EGF, or its receptor binding domain, is ligated by conventional procedures (e.g., using T$_4$DNA ligase) to a DNA sequence corresponding to a GGG spacer. The C-terminus of the EGF-GGG DNA sequence is then fused to the N-terminus of a DNA sequence encoding the conditional, membrane binding peptide KGEAALA(EALA)$_4$-EALEALAA. Alternately, peptide-spacer DNA sequences may be synthesized in vitro using standard oligonucleotide synthesis procedures (see, e.g., U.S. Pat. Nos. 4,500,707 and 4,668,777). The recombinant EGF peptide DNA sequence is cloned in an *E. coli* expression vector using conventional procedures. *E. coli* strain HB101 is transformed with the fused recombinant DNA sequence and cultured to produce the EGF peptide. The fusion protein is purified form the transformed *E. coli* culture by standard methods, including anti-EGF affinity chromatography. The fusion protein may be eluted from the affinity matrix using standard techniques, such as high salt, chaotropic agents, or high or low pH. Loss of EGF receptor is measured by flow cytometry and mouse monoclonal antibody to EGF receptor.

Example 23

Synthesis of a Vitamin $B_{12}$ Derivative Having a Water-solubilizing Liner The preparation of a vitamin $B_{12}$ derivative having a water-solubilizing linker is described. Briefly, the example describes a procedure for the reaction of a cyanocobalamin monoocarboxylic acid with 4,7,10-trioxa-1,13-tridecane diamine. The results for the b- and e-monoacids of cyanocobalamin are described. The reaction product for the e-isomer is shown below.

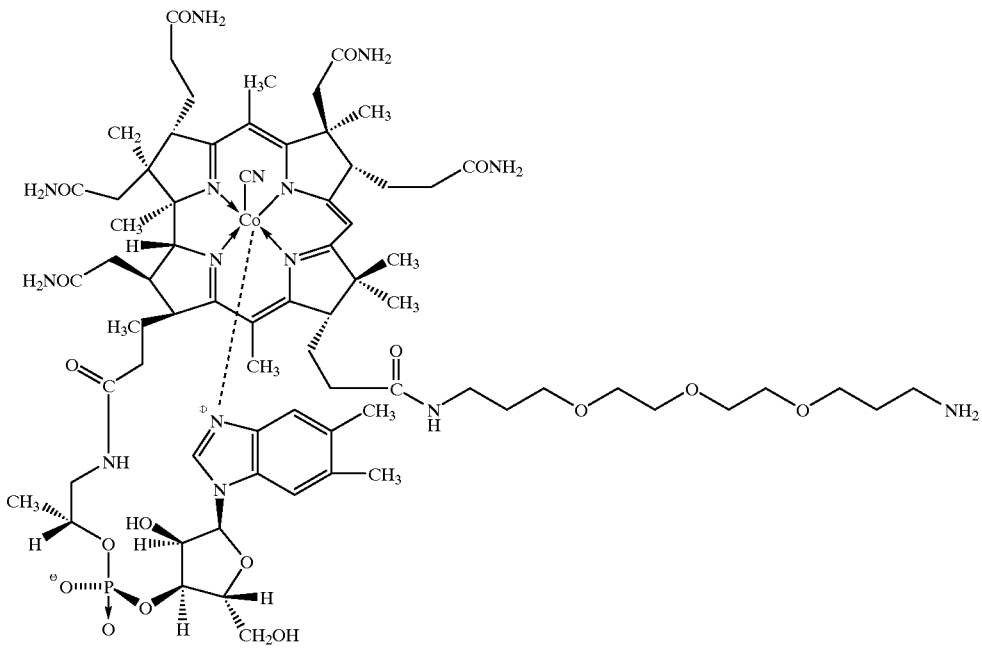

Cyanocobalamin monocarboxylic acid (1.472 mmol, 2 g) and N-hydroxysuccinimide (680 mg) were dissolved in water (100 mL) and 1.456 g of sodium cyanide was added. 4,7,10-Trioxa-1,13-Tridecanediamine (36 mmol, 16 g) was then added and the pH was adjusted to 6 with 1 N HCl. N-ethyl-N'-dimethylamino-propyl-carbodiimide-hydrochloride (EDC) (1.136 g) was added and the pH of the solution was readjusted to 5.5. The reaction mixture was then stirred overnight in the dark at room temperature. In 5 intervals of 6 to 14 h 680 mg of N-hydroxysuccinimide and 1.136 g of EDC were added to the solution, readjusting the pH value to 5.5 each time. After a total reaction time of 4 days (HPLC monitored) the solution was evaporated to dryness, the residue was digested with 100 mL of acetone and the solvent was decanted. The solid residue was dissolved in 50 mL of H$_2$O and applied to an Amberlite XAD-2 (200 g; 4 cm×60 cm) column. The column was eluted with 1 L water, then the desired product was eluted with 500 mL methanol. The methanol fractions were evaporated to dryness, and the residue was dissolved in 25 mL of water and was applied to a Dowex Cl$^-$ column (100 g, 2.5 cm×60 cm, acetate form, 200–400 mesh). The final product was eluted using 250 mL water, thereby leaving non-converted acid bound to the column, which was later eluted with 0.04 mol/L sodium acetate buffer pH 4.7. The fractions containing the final product were evaporated to dryness, then digested with acetone and filtered. The solid obtained was recrystallized from aqueous acetone.

b-isomer: yield: 2 g (87%), mp: 213–217_C with decomposition. $^1$H NMR (MeOH-d$_4$, δ): 0.44 (s, 3H); 1.17 (d, 5H), 1.25 (d, 4H); 1.36 (d, 7H), 1.45 (s, 4H); 1.74 (m, 10H); 1.88 (s, 11H); 2.27 (d, 8H); 2.34 (m, 11H); 2.56 (m, 11H); 3.17 (t, 3H); 3.2 (m, 9H); 3.3 (m, 6H); 3.4 (m, 4H); 3.5 (s, 7H); 3.58 (s, 8H); 3.6 (m, 11H); 3.7 (m, 1H); 3.88 (m, 1H), 4.07 (m, 1H); 4.1 (m, 1H); 4.17 (m, 1H), 4.3 (m, 1H), 4.5 (m, 1H); 4.6 (m, 1H); 6.04 (d, 1H), 6.27(s, 1H); 6.52 (s, 1H); 7.13 (d, 1H); 7.25 (s, 1H); MS (FAB$^+$): m/e 1558 (M$^+$). IR (KBr): 3400, 3200, 2950, 2060, 1660, 1570, 1490, 1060 cm$^{-1}$. UV (H$_2$O): λ361 (ε17470).

e-isomer: yield: 1.5 g (65%), mp: 112–116_C with decomposition. $^1$H NMR (MeOH-d$_4$, δ): 0.44 (s, 3H); 1.18 (s, 3H); 1.25 (d, 5H); 1.37 (d, 8H); 1.45 (s, 4H); 1.74 (m, 10H); 1.88 (s, 11H); 2.28 (d, 7H); 2.3 (m, 15H); 2.56 (d, 11H); 3.17 (t, 3H); 3.2 (t, 4H); 3.3 (m, 1H); 3.4 (m, 4H); 3.5 (s, 7H); 3.58 (d, 3H); 3.6 (m, 5H); 3.7 (m, 1H); 4.0 (m, 1H); 4.1 (d, 1H); 4.19 (m, 1H); 4.3 (m, 1H), 4.5 (d, 1H); 4.6 (m, 1H); 6.05 (d, 1H); 6.27 (s, 1H); 6.57 (s, 1H); 7.1 (d, 1H); 7.25 (s, 1H). MS (FAB$^+$): m/e 1558 (M$^+$). IR (KBr): 3400, 3200, 2950, 2060, 1660, 1570, 1490, 1060 cm$^{-1}$. UV (H$_2$O): λ361 (ε12818).

Example 24

Synthesis of a Vitamin B$_{12}$/biotin Conjugate Having a Water-solubilizing Linker The preparation of a vitamin B$_{12}$/biotin conjugate having a water soluble linker is described. Briefly, the vitamin B$_{12}$ derivative having a water-solubilizing linker prepared as described in Example 23 is treated with an NHS-ester of biotin. The results for the b-and e-isomers of cobalamin are described. The reaction product for the e-isomer is shown below.

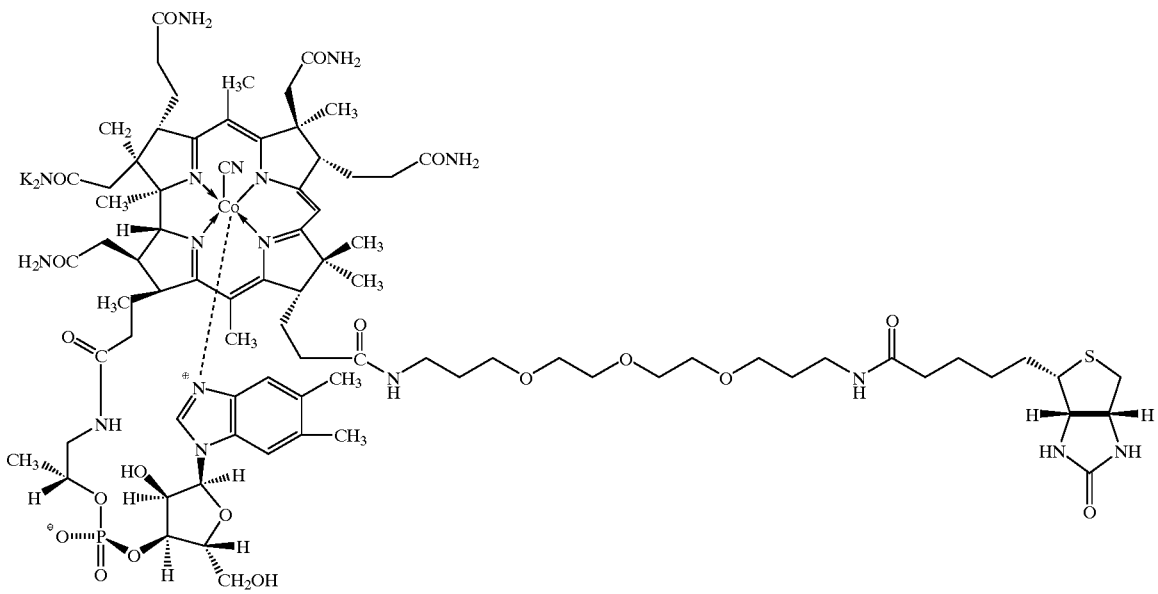

In a solution of cyanocobalamin monocarboxylic acid trioxadiamine conjugate (0.193 mmol, 300 mg) in DMF (10 mL), triethylamine (0.193 mmol, 0.027 mL) was added. N-hydroxysuccinimidobiotin (0.232 mmol 79 mg) was then added and the reaction was stirred overnight. It was then evaporated to dryness. The residue was dissolved in 10 mL of methanol-water (1:1 v/v) and the solution was applied to a reverse phase column (500 mm×25 mm, Alltech, 150 psi) (octadecyl) which was developed with the same solvent. RAININ Rabbit-plus peristaltic pumping system was used with a DYNAMAX (model UV-1) UV visible absorbance detector; the elute was collected with an automatic fraction collector. The fractions containing the final product (HPLC monitored) were evaporated to dryness.

b-isomer (9): yield: 160 (53%) mp: 195–197_C with decomposition. $^1$H NMR (MeOH-d$_4$, δ): 0.44 (s, 3H); 1.17 (s, 3H), 1.23 (s, 4H), 1.35 (s, 6H); 1.43 (s, 4H), 1.6 (m, 4H); 1.73 (s, 8H3; 1.86 (s, 4H); 2.05 (m, 4H), 2.17 (s, 2H); 2.26 (s, 7H); 2.35 (s, 3H); 2.55 (m, 10H); 2.88 (m, 4H); 3.2 (m, 6H); 3.5 (s, 6H); 3.57 (s, 3H); 3.6 (s, 5H); 3.75 (d, 1H); 3.87 (d, 1H), 4.0 (s, 1H); 4.1 (d, 1H); 4.16 (s, 1H) 4.28 (s, 2H), 4.49 (m, 2H); 4.66 (m, 1H); 6.03 (s, 1H); 6.26 (s, 1H); 6.55 (s, 1H); 7.11 (s, 1H); 7.24 (s, 1H). MS (FAB$^+$): m/e 1784 (M$^+$). IR (KBr): 3400, 3200, 2950, 2060, 1660, 1570, 1490, 1060 cm$^{-1}$. UV (H$_2$O): λ361 (ε22770).

e-isomer (10): yield: 80 mg (32%), mp: 224–227_C with decomposition. $^1$H NMR (MeOH-d$_4$, δ): 0.44 (s, 3H); 1.17 (s, 3H); 1.23 (d, 4H); 1.35 (d, 6H); 1.44 (s, 4H); 1.74 (m, 5H); 1.87 (s, 4H); 2.06 (m, 4H); 2.18 (m, 3.H); 2.26 (d, 7H), 2.35 (s, 3H); 2.55 (d, 9H); 2.9 (m, 4H); 3.24–3.3 (m, 4H), 3.5 (s, 6H); 3.57 (s, 3H); 3.6 (s, 5H); 3.75 (dd, 1H); 3.87 (dd, 1H), 4.0 (m, 1H), 4.1 (d, 1H); 4.17 (t, 1H); 4.28 (m, 2H); 4.47 (m, 1H), 4.5 (m 1H); 4.66 (m, 1H); 6.04 (s, 1H); 6.27 (d, 1H); 6.56 (s, 1H); 7.11 (s, 1H); 7.24 (s, 1H). MS (FAB$^+$): m/e 1784 (M$^+$). IR (KBr): 3400, 3200, 2950, 2060, 1660, 1570, 1490, 1060 cm$^{-1}$. UV (H$_2$O): λ361 (ε22021).

Example 25

Synthesis of a Vitamin B$_{12}$ Dimer Having a Water-solubilizing Linker

The preparation of two vitamin B$_{12}$ dimers having water-solubilizing linkers is described. Briefly, the dimers are prepared by coupling the vitamin B$_{12}$ derivative of Example 23 with either a bifunctional crosslinker or a trifunctional crosslinker.

A. Isophthaloyl crosslinked dimer. The preparation and results for crosslinking using isophthaloyl dichloride and the b-isomer of cyanocobalamin monocarboxylic acid trioxadiamine conjugate are presented. The reaction product for the e-isoma is shown below.

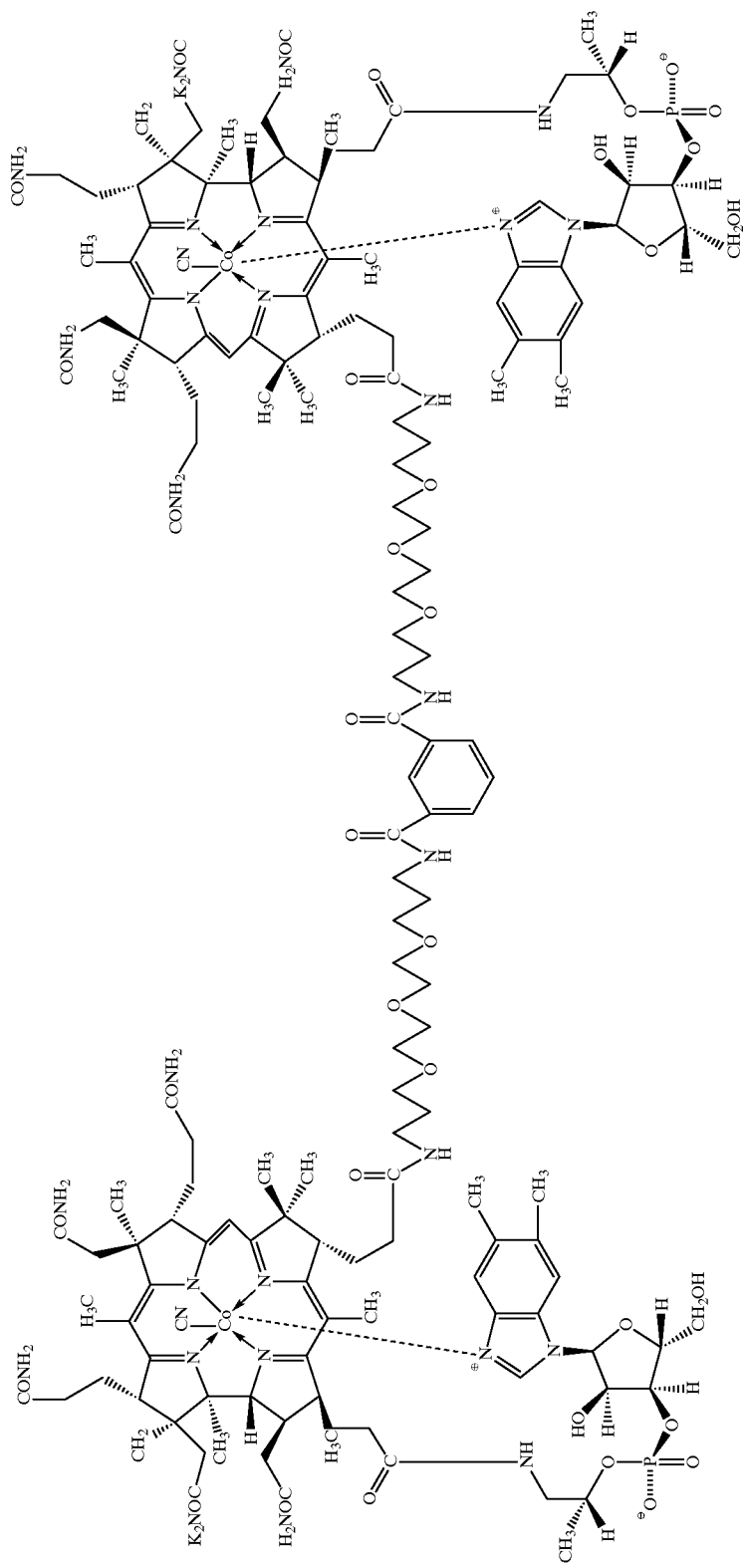

In a solution of cyanocobalamin monocarboxylic acid trioxadiamine conjugate (0.193 mmol, 0.300 g) in DMF (20 mL), triethylamine (0.030 mL) was added. Isophthaloyl dichloride (0.096 mmol, 0.0195 g) was added over a period of 10–15 min. The reaction mixture was stirred at room temperature for 4–5 days (HPLC monitored), and triethylamine (0.030 mL) was added every after 24 hours. After evaporating to dryness, the solid was dissolved in 20 mL of methanol: $H_2O$ (1:1) and applied to a reverse phase column (500 mm×25 mm, Alltech, 150 psi) (octadecyl) which was developed with the same solvent. A RAININ Rabbit-plus peristaltic pumping system was used with a DYNAMAX (model UV-1) UV visible absorbance detector; the elute was collected with an automatic fraction collector. The fractions containing the final product (HPLC monitored) were evaporated to dryness.

b-isomer (11): yield: 100 mg, mg: 195–198° C. with decomposition. $^1$H NMR (MeOH, δ): 0.44 (s, 6H); 1.18 (s, 6H); 1.25 (d, 7H); 1.31 (t, 20H); 1.36 (s, 14H); 1.45 (s, 8H); 1.74 (m, 20H); 1.88 (d, 15H); 2.27 (s, 11H); 2.37 (m, 22H); 2.56 (d, 20H); 2.85 (s, 5H); 2.99 (s, 2H); 3.2 (m, 18H); 3.3 (m, 12H); 3.4 (m, 10H); 3.5 (s, 14H); 3.58 (s, 18H); 3.6 (s, 30H); 3.9 (d, 4H); 4.0 (d, 2H); 4.1 (d, 2H); 4.18 (d, 2H); 4.3 (m, 2H), 4.5 (m, 2H), 4.7 (m, 2H), 6.0 (s, 2H); 6.28 (s, 2H), 6.56 (s, 2H), 7.1 (s, 2H); 7.25 (s, 2H); 7.56 (m, 1H); 7.8 (d, 2H); 8.3 (s, 1H). IR (KBr): 3400, 3200, 2950, 2060, 1660, 1570, 1490, 1060 cm$^{-1}$. UV ($H_2O$): λ361 (ε33865).

B. Trifunctional crosslinked dimer. The preparation and results for crosslinking using a trifunctional crosslink and the b- and e-isomers of the cobalamin derivative are presented. The reaction for the e-isomer is shown below.

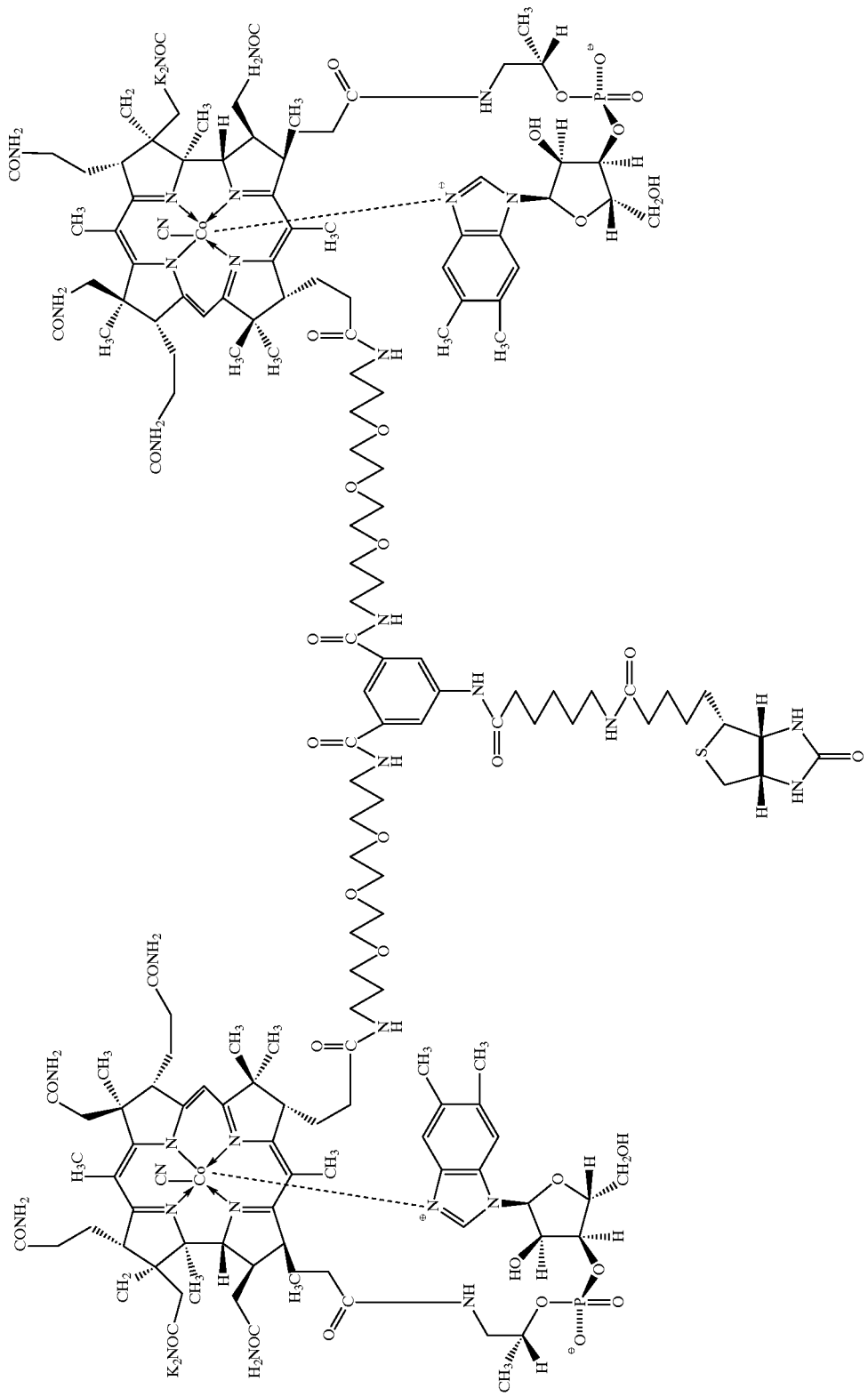

In a solution of cyanocobalamin carboxylic acid-trioxadiamine conjugate (0.193 mmol, 0.3 g) in DMF (15 mL), triethylamine (0.030 mL) was added. DiTFP ester of Biotin-caproic acid-Isophthalic acid (0.0965 mmol, 0.079 ) was added over a period of 5–10 min. The reaction mixture was stirred at room temperature for 3–4 days (HPLC monitored), adding triethylamine (0.030 mL) every after 24 hours. It was then evaporated to dryness. The solid was dissolved in 20 mL of methanol: $H_2O$ (1:1) and applied to a reverse phase column (500 mm×25 mm, Alltech, 150 psi) (octadecyl) which was developed with the same solvent. A RAININ Rabbit-plus peristaltic pumping system was used with a DYNAMAX (model UV-l) UV visible absorbance detector; the elute was collected with an automatic fraction collector. The fractions containing the final product (HPLC monitored) were evaporated to dryness.

b-isomer (12): yield: mp: 192–195_C with decomposition. IR (KBr): 3400, 3200, 2950, 2060, 1660, 1570, 1490, 1060 $cm^{-1}$.

e-isomer (13): IR (KBr): 3400, 3200, 2950, 2060, 1660, 1570, 1490, 1060 $cm^{-1}$.

Example 26

Synthesis of a Vitamin $B_{12}$ 5'-O-Ribose Ether Derivative

The preparation of a cyanocobalamine methyl acetate derivative having a 5-O-ribose ether linkage is described. Briefly, alkylation of cyanocobalamin with methyl bromoacetate provides the ether having the structure shown below.

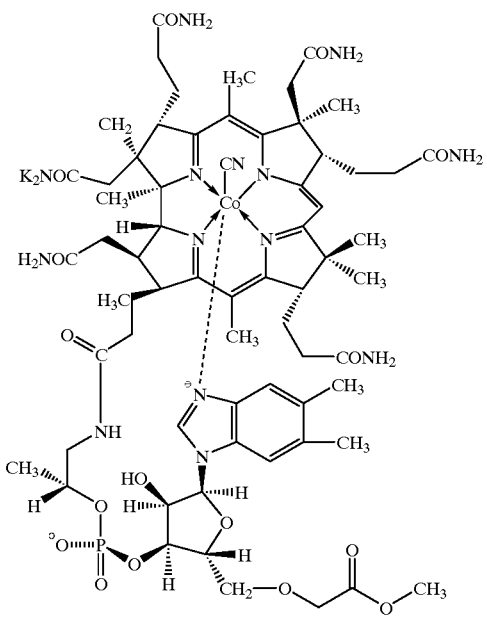

Preparation of Cyanocobalamin-methylacetate derivative: Cyanocobalamin (0.15 mmol, 200 mg) was dissolved in 40 mL of DMSO containing 10 g (65 mmol) of methyl bromoacetate and 6.4 mL of pyridine. After 14–16 h at 50–55° C., 500 mL of water was added and the pH of the reaction mixture was adjusted to 6 with 10% KOH. KCN was then added at a final concentration of 0.01 M and the pH of the solution was readjusted to 6 with 3 N HCl. After 1 h the cyanocobalamin components were desalted by phenol extraction and applied to a 100 g of Dowex Cl⁻ (2.5 cm×60 cm) column (acetate form 200–400 mesh). Cyanocobalamin was eluted 10 with water. Methylacetate derivative was eluted with NaOAc (0.04 M, pH 4.67).

From the foregoing, it will be appreciated that, although specific embodiments of this invention have been described herein for purposes of illustration, various modifications may be made without deviating from the spirit and scope of the invention. Accordingly, the invention is not limited except by the appended claims.

While the preferred embodiment of the invention has been illustrated and described it will be appreciated that various changes can be made therein without departing from the spirit and scope of the invention.

What is claimed is:

1. A vitamin $B_{12}$ derivative comprising vitamin $B_{12}$ covalently coupled to biotin by a water-soluble linker.

2. The vitamin $B_{12}$ derivative of claim 1 wherein the water-soluble linker comprises a hydrophilic moiety selected from the group consisting of polyhydroxy, polyamino, and polyether moieties.

3. The vitamin $B_{12}$ derivative of claim 2 wherein the hydrophilic moiety is a polyhydroxy moiety selected from the group consisting of glycol, glycerol, and polysaccharide moieties.

4. The vitamin $B_{12}$ derivative of claim 2 wherein the hydrophilic moiety is a polyether moiety selected from the group consisting of polyethylene, ethoxy ethanol, and ethoxy ethoxy ethanol moieties.

5. The vitamin $B_{12}$ derivative of claim 1 wherein the water-soluble linker is a polyether linker.

6. The vitamin $B_{12}$ derivative of claim 5 wherein the polyether linker is selected from the group consisting of a 4,7,10-trioxa-1,13-tridecanediamine linker and a 3,6-dioxa-1,8-octadiamine linker.

7. The vitamin $B_{12}$ derivative of claim 1 wherein the water-soluble linker is coupled to a vitamin $B_{12}$ coupling site selected from the group consisting of coupling sites a–g, coupling site h, and coupling site i, shown in the structure:

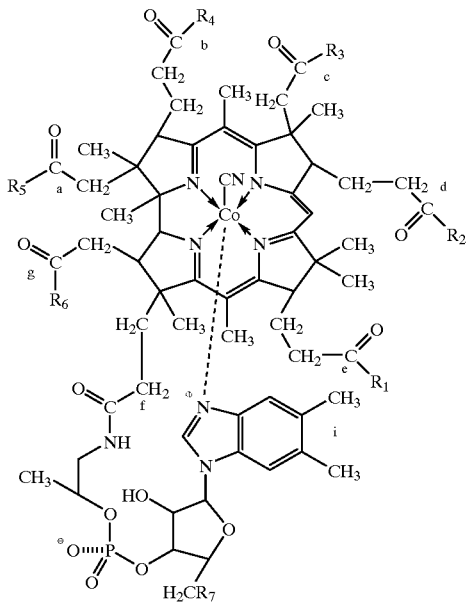

8. The vitamin $B_{12}$ derivative of claim 1 wherein the water-soluble linker is coupled to a vitamin $B_{12}$ ribose coupling site by an ether linkage.

9. The vitamin $B_{12}$ derivative of claim 8 wherein the $B_{12}$ ribose coupling site is a 5'-OH group.

10. The vitamin $B_{12}$ derivative of claim 8 wherein the ether linkage is selected from the group consisting of an alkyl ether linkage, an aryl ether linkage, a benzyl ether linkage, and a silyl ether linkage.

11. A complex comprising the vitamin $B_{12}$ derivative of claim 1 bound to a transcobalamin II.

12. A composition, comprising the vitamin $B_{12}$ derivative of claim 1 and a pharmaceutically acceptable carrier or diluent.

13. A complex comprising the vitamin $B_{12}$ derivative of claim 1 bound to an avidin.

14. The complex of claim 13 wherein the complex comprises two vitamin $B_{12}$ derivatives.

15. The complex of claim 13 wherein the complex comprises four vitamin $B_{12}$ derivatives.

16. The complex of claim 13 wherein the avidin is streptavidin.

* * * * *

UNITED STATES PATENT AND TRADEMARK OFFICE
CERTIFICATE OF CORRECTION

PATENT NO. : 6,083,926
DATED : July 4, 2000
INVENTOR(S) : Morgan, Jr. et al.

It is certified that error appears in the above-identified patent and that said Letters Patent is hereby corrected as shown below:

Title page,
The following should be added to Section [56]:
-- OTHER PUBLICATIONS Akin, Cem, et al., "Modulation of Transferrin Receptor Expression by Insulin and Granulocyte-Macrophage Colony Stimulating Factor in AML-193 Leukemic Cells," *Cancer Letters*, Vol. 69, 1993, pp. 51-57.

Anderson, Richard G.W., et al., "Potocytosis: Sequestration and Transport of Small Molecules by Caveolae," *Science*, Vol. 255, 24 January 1992, pp. 410-411.

Ashworth, Rachel, et al., "Visualization of the Thyrotropin-Releasing Hormone Receptor and its Ligand During Endocytosis and Recycling," *Proceedings of the National Academy of Science USA*, Vol. 92, January 1995, pp. 512-516.

Carpentier, Jean-Louis, et al., "Potassium Depletion and Hypertonic Medium Reduce 'Non-Coated' and Clathrin-Coated Pit Formation, as Well as Endocytosis Through These Two Gates," *Journal of Cellular Physiology*, Vol. 138, 1989, pp. 519-526.

Cavallaro, Ugo, et al., "Targeting Plant toxins to the Urokinase and $\alpha_2$-Macroglobulin Receptors," *Seminars in Cancer Biology*, Vol. 6, 1995, pp. 269-278.

Ciechanover, Aaron, "The Ubiquitin-Proteasome Proteolytic Pathway," *Cell*, Vol. 79, October 7, 1994, pp. 13-21.

Gratzer, W.B., et al., "The Red Blood Cell and Malaria Parasite Invasion," *Seminars in Hematology*, Vol. 30, No. 3, July 1993, pp. 232-247.

Jabbar, M. Abdul, et al., "Intracellular Interaction of Human Immunodeficiency Virus Type 1 (ARV-2) Envelope Glycoprotein gp160 with CD4 Blocks the Movement and Maturation of CD4 to the Plasma Membrane," *Journal of Virology*, Vol. 64, No. 12, December 1990, pp. 6297-6304.

Joly, Marguerite, et al., "Disruption of PDGF Receptor Trafficking by Mutation of its PI-3 Kinase Binding Sites," *Science*, Vol. 263, 4 February 1994, pp. 684-687. --

UNITED STATES PATENT AND TRADEMARK OFFICE
CERTIFICATE OF CORRECTION

PATENT NO. : 6,083,926
DATED : July 4, 2000
INVENTOR(S) : Morgan, Jr. et al.

It is certified that error appears in the above-identified patent and that said Letters Patent is hereby corrected as shown below:

The following should be added to Section [56]:
-- OTHER PUBLICATIONS

Kreiner, Thane, et al., "Membrane Traffic Between Secretory Compartments is Differentially Affected During Mitosis," *Cell Regulation*, Vol. 1, April 1990, pp. 415-424.

Malorni, Walter, et al., "Menadione-Induced Oxidative Stress Leads to a Rapid Down-Modulation of Transferrin Receptor Recycling," *Journal of Cell Science*, Vol. 106, 1993, pp. 309-318.

Mayor, Satyajit, et al., "Sequestration of GPI-Anchored Proteins in Caveolae Triggered by Cross-Linking," *Science*, Vol. 264, 24 June 1994, pp. 1948-1951.

Mayor, Satyajit, et al., "Sorting of Membrane Components from Endosomes and Subsequent Recycling to the Cell Surface Occurs by a Bulk Flow Process," *The Journal of Cell Biology*, Vol. 121, No. 6, June 1993, pp. 1257-1269.

McLean, Gary R., et al., "Cobalamin Analogues Modulate the Growth of Leukemia Cells *in Vitro*," *Cancer Research*, September 15, 1997, pp. 4015-4022.

Parton, Robert G., et al., "Regulated Internalization of Caveolae," *The Journal of Cell Biology*, Vol. 127, No. 5, December 1994, pp. 1199-1215.

Pathare, Pradip M., et al., "Synthesis of Cobalamin Dimers Using Isophthalate Cross-Linking of Corrin Ring Carboxylates and Evaluation of Their Binding to Transcobalamin II, *"Bioconjugate Chem.*, Vol. 8, No. 2, 1997, pp. 161-172.

Pignatello, Joseph J., et al., "Self-Association of Organocobalamins in Aqueous Solution," *Journal of the Chemical Society Dalton Trans.*, 1985, pp. 1381-1386.

Robertson, Barbara J., et al., "Role of Vesicular Traffic in the Transport of Surface Transferrin Receptor to the Golgi Complex in Cultured Human Cells," *Archives of Biochemistry and Biophysics*, Vol. 292, No. 1, January 1992, pp. 190-198. --

UNITED STATES PATENT AND TRADEMARK OFFICE
CERTIFICATE OF CORRECTION

PATENT NO. : 6,083,926
DATED : July 4, 2000
INVENTOR(S) : Morgan, Jr. et al.

It is certified that error appears in the above-identified patent and that said Letters Patent is hereby corrected as shown below:

The following should be added to Section [56]:
-- OTHER PUBLICATIONS

Ross, John F., et al., "Differential Regulation of Folate Receptor Isoforms in Normal and Malignant Tissues In Vivo and in Established Cell Lines," *Cancer*, Vol. 73, No. 9, May 1, 1994, pp. 2432-2443.

Schnitzer, Jan E., et al., "Filipin-Sensitive Caveolae-Mediated Transport in Endothelium: Reduced Transcytosis, Scavenger Endocytosis, and Capillary Permeability of Select Macromolecules," *The Journal of Cell Biology*, Vol. 127, No. 5, December 1994, pp. 1217-1232.

Sigal, Nolan H., et al., "Cyclosporin A, FK-506, and Rapamycin: Pharmacologic Probes of Lymphocyte Signal Transduction," *Annual Review Immunology*, Vol. 10, 1992, pp. 519-560.

Smart, Eric J., et al., "Caveolin Moves from Caveolae to the Golgi Apparatus in Response to Cholesterol Oxidation," *The Journal of Cell Biology*, Vol. 127, No. 5, December 1994, pp. 1185-1197.

Sorkin, Alexander, et al., "Endocytosis of Growth Factor Receptors," *BioEssays*, Vol. 15, No. 6, June 1993, pp. 375-382.

Sorkin, Alexander, et al., "Interaction of Activated EGF Receptors with Coated Pit Adaptins," *Science*, Vol. 261, 30 July 1993, pp. 612-615.

Thiele, Dwain L., et al., "The Role of Leucyl-Leucine Methyl Ester-Sensitive Cytotoxic Cells in Skin Allograft Rejection," *Transplantation*, Vol. 53, No. 6, June 1992, pp. 1334-1340.

Toraya, Tetsuo, et al., "Preparation, Properties and Biological Activities of Succinyl Derivatives of Vitamin $B_{12}$," *Bioinorganic Chemistry*, Vol. 4, 1975, pp. 245-255.

Trowbridge, I.S., et al., "Signal-Dependent Membrane Protein Trafficking in the Endocytic Pathway," *Annual Review Cell Biology*, Vol. 9, 1993, pp. 129-161. --

UNITED STATES PATENT AND TRADEMARK OFFICE
CERTIFICATE OF CORRECTION

PATENT NO.   : 6,083,926
DATED        : July 4, 2000
INVENTOR(S)  : Morgan, Jr. et al.

It is certified that error appears in the above-identified patent and that said Letters Patent is hereby corrected as shown below:

The following should be added to Section [56]:
-- OTHER PUBLICATIONS

Wang, Ji Ming, et al., "Studies of Binding and Internalization of Human Recombinant Monocyte Chemotactic and Activating Factor (MCAF) by Monocytic Cells," *Cytokine*, Vol. 5, No. 3 (May), 1993, pp. 264-275.

White, Suhaila, et al., "Combinations of Anti-Transferrin Receptor Monoclonal Antibodies Inhibit Human Tumor Cell Growth *in Vitro* and *in Vivo:* Evidence for Synergistic Antiproliferative Effects," *Cancer Research*, Vol. 50, October 1, 1990, pp. 6295-6301.

Ying, Y.-S., et al., "Each Caveola Contains Multiple Glycosyl-Phosphatidylinositol-Anchored Membrane Proteins," *Cold Spring Harbor Symposia on Quantitative Biology*, Vol. 57, 1992, pp. 593-604.

Krautler, Bernhard, et al., "Oligomethylene-Bridged Vitamin $B_{12}$ Dimers," *Angewandt Chemie International Edition English*, Vol. 34, No. 1, *1995*.

Pathare, Pradip M., et al., "Synthesis of Vitamin-$B_{12}$-Biotin Conjugates Which Vary in Position of Coupling," *Abstracts of Papers of the American Chemical Society*, National Meeting, Anaheim, CA, April 2-6. 1995.

UNITED STATES PATENT AND TRADEMARK OFFICE
CERTIFICATE OF CORRECTION

PATENT NO. : 6,083,926
DATED : July 4, 2000
INVENTOR(S) : Morgan, Jr. et al.

It is certified that error appears in the above-identified patent and that said Letters Patent is hereby corrected as shown below:

Takahashi, Kiyoshi, et al., "Receptor Binding and Internalization of Immobilized Transcobalamin II 11 by Mouse Leukaemia Cells," *Nature,* Vol. 288, No. 18, 25 December 1980, pp. 713-715.--

Signed and Sealed this

Second Day of October, 2001

Attest:

*Nicholas P. Godici*

*Attesting Officer*

NICHOLAS P. GODICI
*Acting Director of the United States Patent and Trademark Office*